United States Patent
Ezerzer et al.

(10) Patent No.: US 12,072,338 B2
(45) Date of Patent: Aug. 27, 2024

(54) PHARMACEUTICAL PEPTIDES FOR THE TREATMENT OF INFLAMMATORY DISEASES

(75) Inventors: Chai Ezerzer, Ness-Ziona (IL); Nicholas Harris, Rehovot (IL)

(73) Assignee: PROTAGONISTS LTD., Ness-Ziona (IL)

(*) Notice: Subject to any disclaimer, the term of this patent is extended or adjusted under 35 U.S.C. 154(b) by 1174 days.

(21) Appl. No.: 12/576,750

(22) Filed: Oct. 9, 2009

(65) Prior Publication Data
US 2010/0227824 A1 Sep. 9, 2010

Related U.S. Application Data

(63) Continuation-in-part of application No. 12/225,122, filed as application No. PCT/IL2007/000350 on Mar. 18, 2007.

(60) Provisional application No. 61/195,691, filed on Oct. 10, 2008.

(51) Int. Cl.
*A61K 38/08* (2019.01)
*G01N 33/68* (2006.01)
*A61K 38/00* (2006.01)

(52) U.S. Cl.
CPC .......... *G01N 33/6863* (2013.01); *A61K 38/00* (2013.01); *G01N 2333/7158* (2013.01); *G01N 2333/726* (2013.01); *G01N 2800/102* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 6,171,590 B1 * | 1/2001 | Howard et al. | 424/185.1 |
| 8,703,911 B2 * | 4/2014 | Ezerzer | C07K 14/7158 530/328 |
| 9,416,158 B2 * | 8/2016 | Ezerzer | C07K 14/7158 |
| 9,931,376 B2 * | 4/2018 | Ezerzer | C07K 14/7158 |

FOREIGN PATENT DOCUMENTS

WO WO 2007105224 * 9/2007

OTHER PUBLICATIONS

CXCR3 sequence (retrieved from http://www.uniprot.org/uniprot/P49682.txt on Sep. 28, 2012, 7 pages).*
Baggiolini et al. ('Human chemokines: an update' Annu. Rev. Immunol. v15 1997 pp. 675-705) (Year: 1997).*
Chen et al. ('Chemokines and chemokine receptors as novel therapeutic targets in rheumatoid arthritis (RA): inhibitory effects of traditional Chinese medicinal components' Cellular and Molecular Immunology v1(5) Oct. 2004 pp. 336-342) (Year: 2004).*
CXCR3 (Cytokines & Cells Encyclopedia—COPE), downloaded http://www.copewithcytokines.de/cope.cgi?key=CXCR3, Oct. 28, 2015.
Laura Lasagni et al., An Alternatively Spliced Variant of CXCR3 Mediates the Inhibition of Endothelial Cell Growth Induced by IP-10, Mig, and I-TAC, and Acts as Functional Receptor for Platelet Factor 4, J. Exp. Med., vol. 197, No. 11, Jun. 2, 2003, pp. 1537-1549.
Marcel Loetscher et al., Chemokine Receptor SPecific for IP10 and Mig: Structure, Function, and Expression in Activated T-Lymphocytes, Sep. 1996, J. Exp. Med., vol. 184, pp. 963-969.
Chai Ezerzer et al., "A Network Approach to Controlling Pathogenic Inflammation", Systems Biomedicine 1:1, 1-12, Oct./Nov. Dec. 2012.

* cited by examiner

*Primary Examiner* — Ronald T Niebauer
(74) *Attorney, Agent, or Firm* — Pillsbury Winthrop Shaw Pittman, LLP

(57) ABSTRACT

The invention provides pharmaceutical compositions comprising at least a portion of a chemokine receptor or a G-protein coupled receptor. The pharmaceutical composition of the invention may be used for altering immune system functioning, for example, to treat an immune system disorder, such as an autoimmune disease, multiple sclerosis, transplant rejection, psoriasis, rheumatoid arthritis and asthma. The invention also provides peptides that may be used individually, in combination with, or in combination with other therapeutic agents such as steroid, non-steroid anti-inflammatory drug, immune modulator or immune suppressor.

7 Claims, 23 Drawing Sheets
Specification includes a Sequence Listing.

CKs

1. GRO-α
2. GRO-β
3. NAP-2
4. IL-8-72
5. IL-8-77
6. Mig
7. IP-10
8. I-TAC
9. I-309
10. MCP-1
11. MCP-2
12. MCP-4
13. MIP1-α
14. MIP1-β
15. RANTES
16. Eotaxin
17. Eotaxin2
18. Eotaxin3
19. TARC
20. MDC-69
21. SDF1-α
22. SDF1-β
23. BCA-1
24. MIP3-α
25. MIP3-β
26. Exodus-2
27. TECK
28. C-TAC
29. Fractalkine
30. Lymphotactin
31. PF-4

FIG. 1

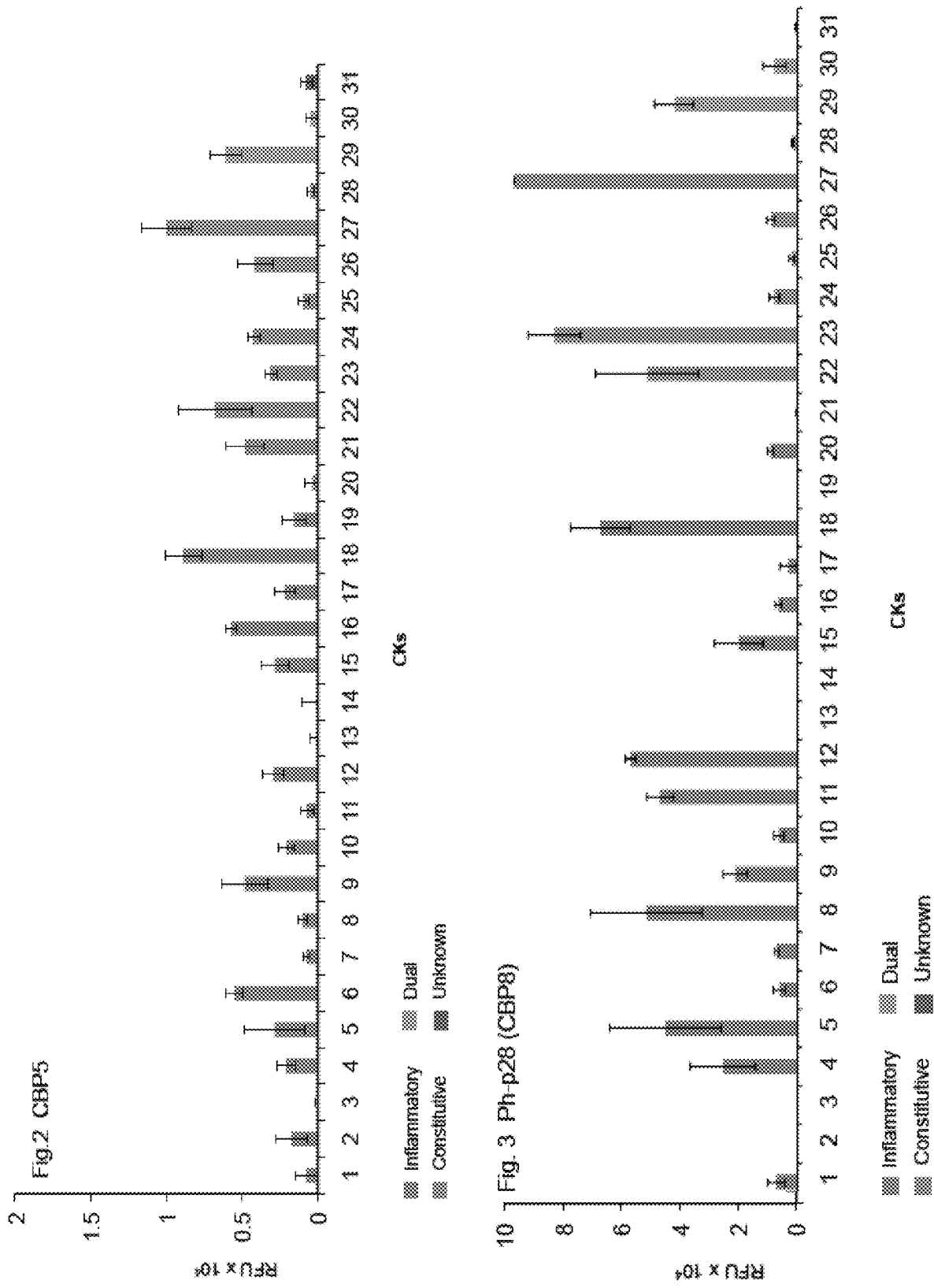

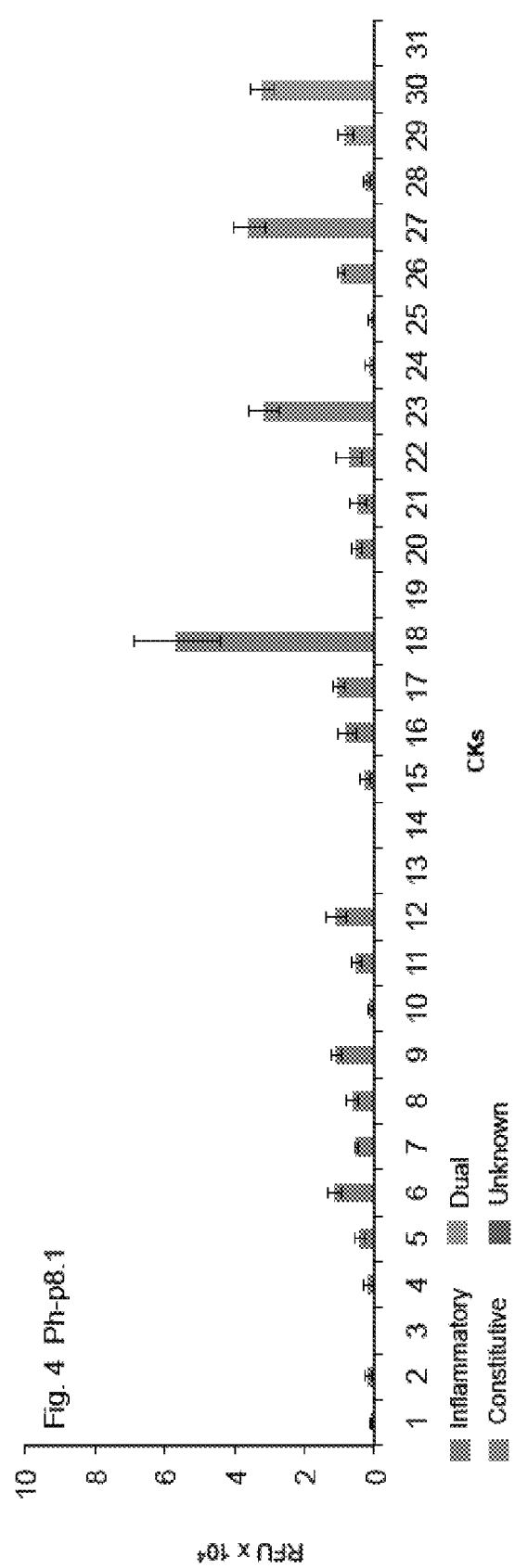
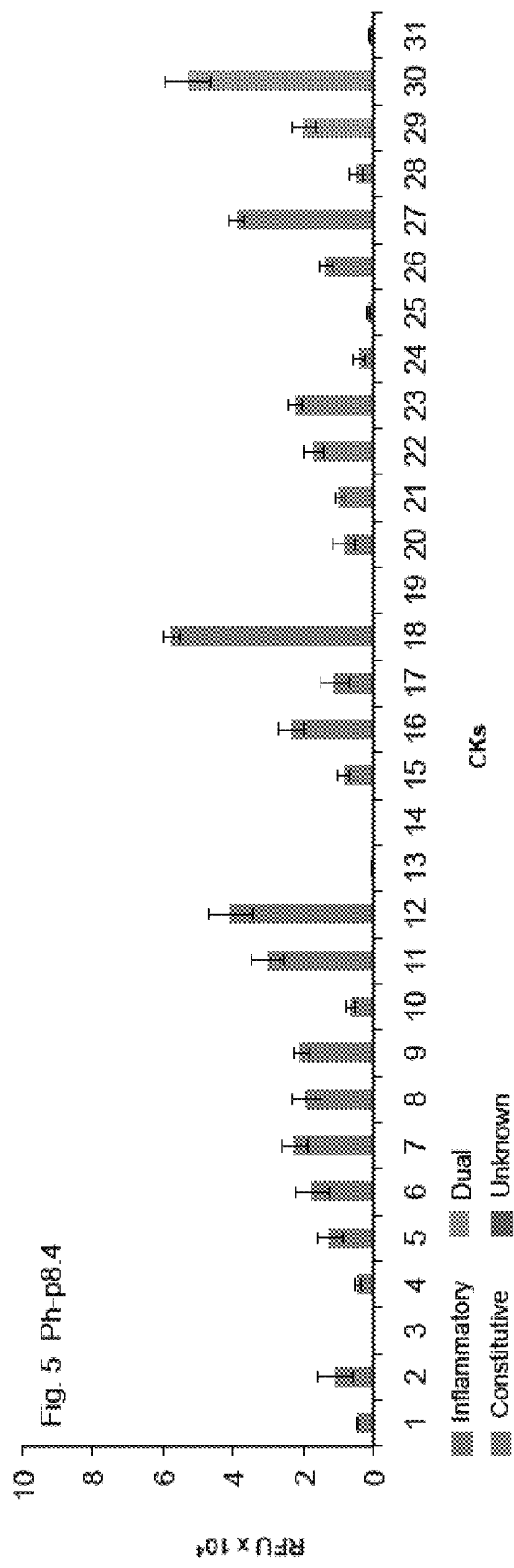

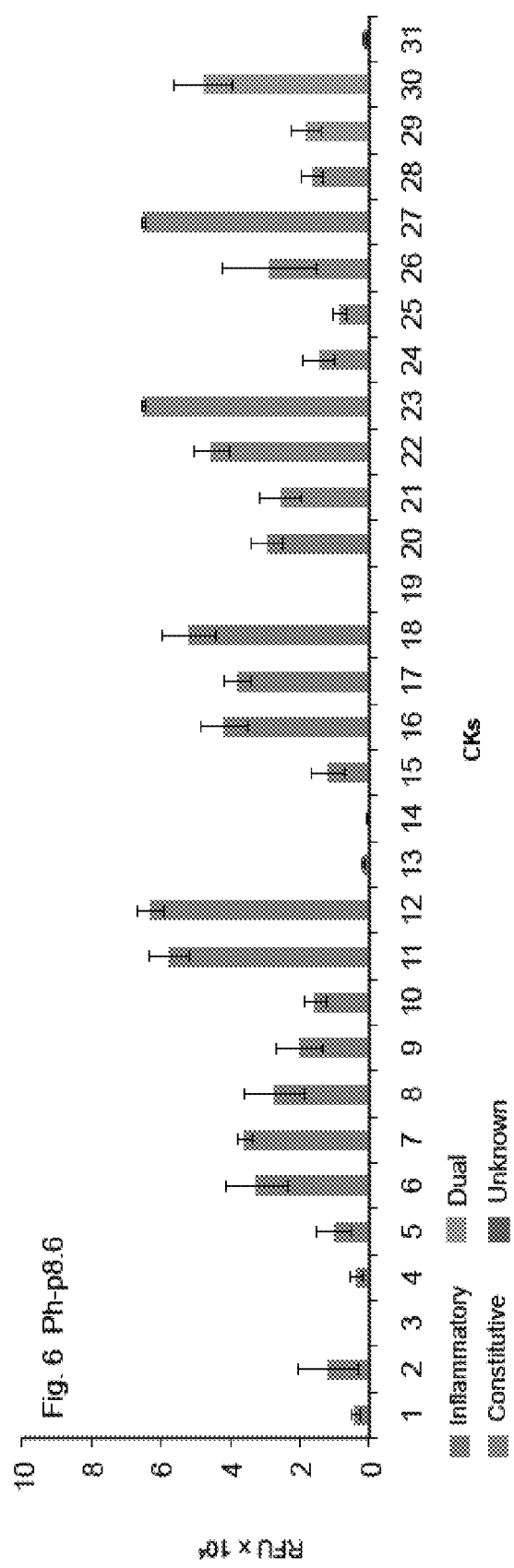
Fig. 6 Ph-p8.6
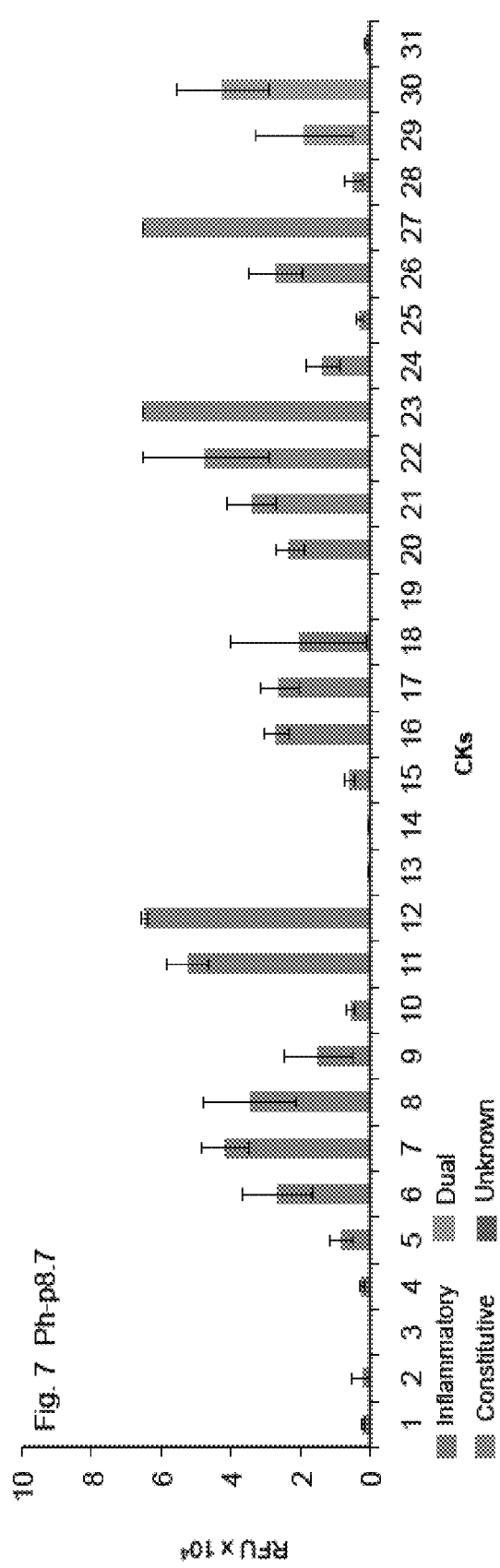
Fig. 7 Ph-p8.7

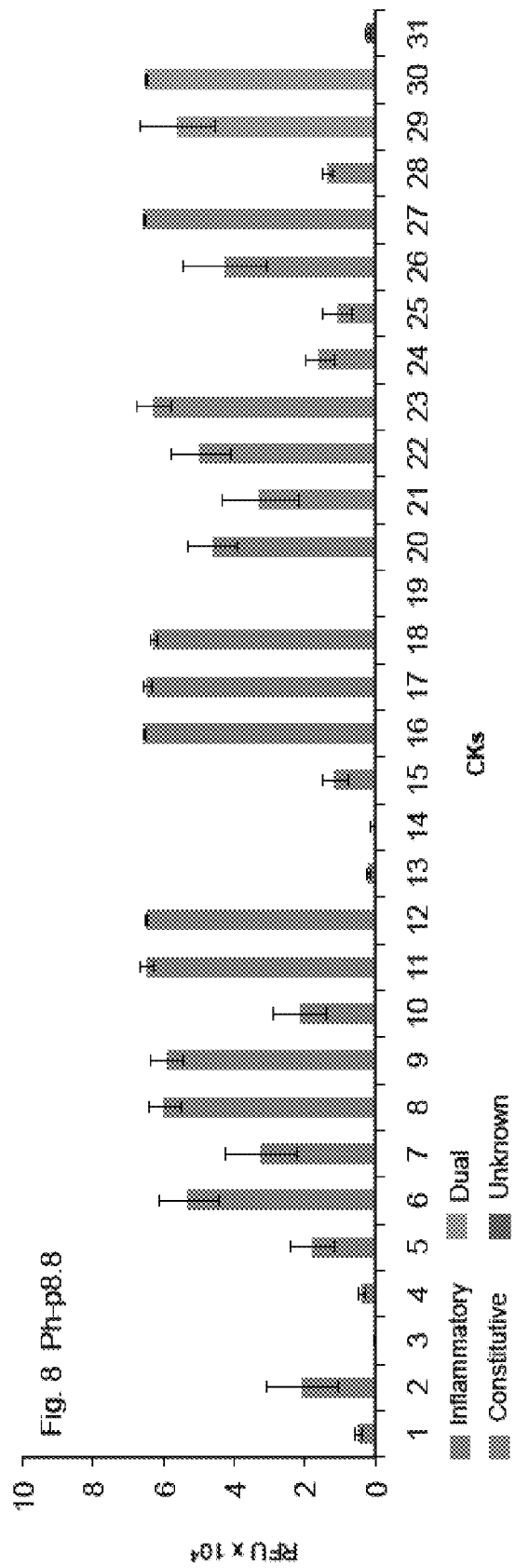
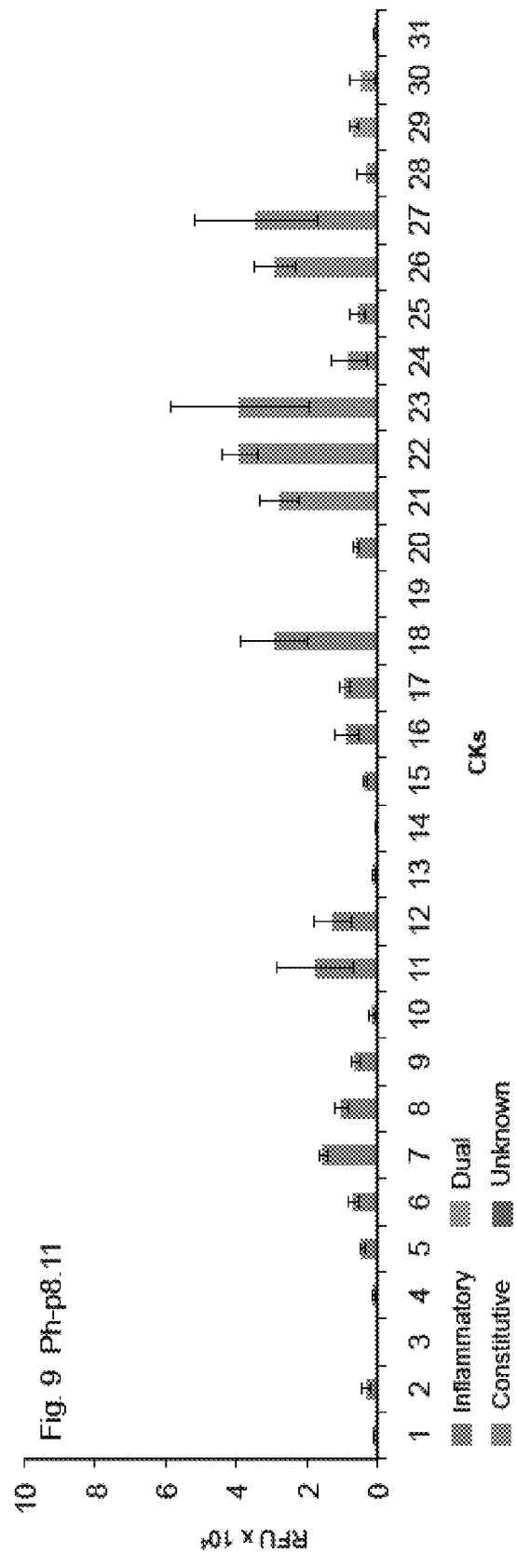

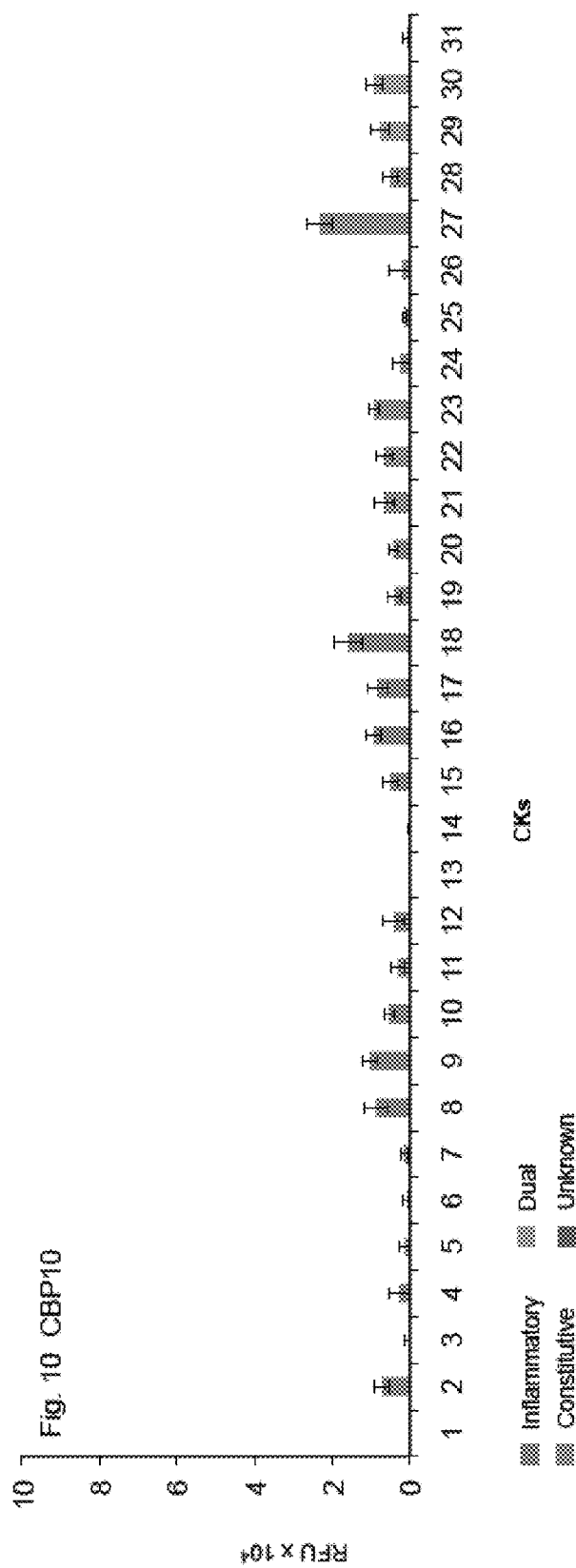

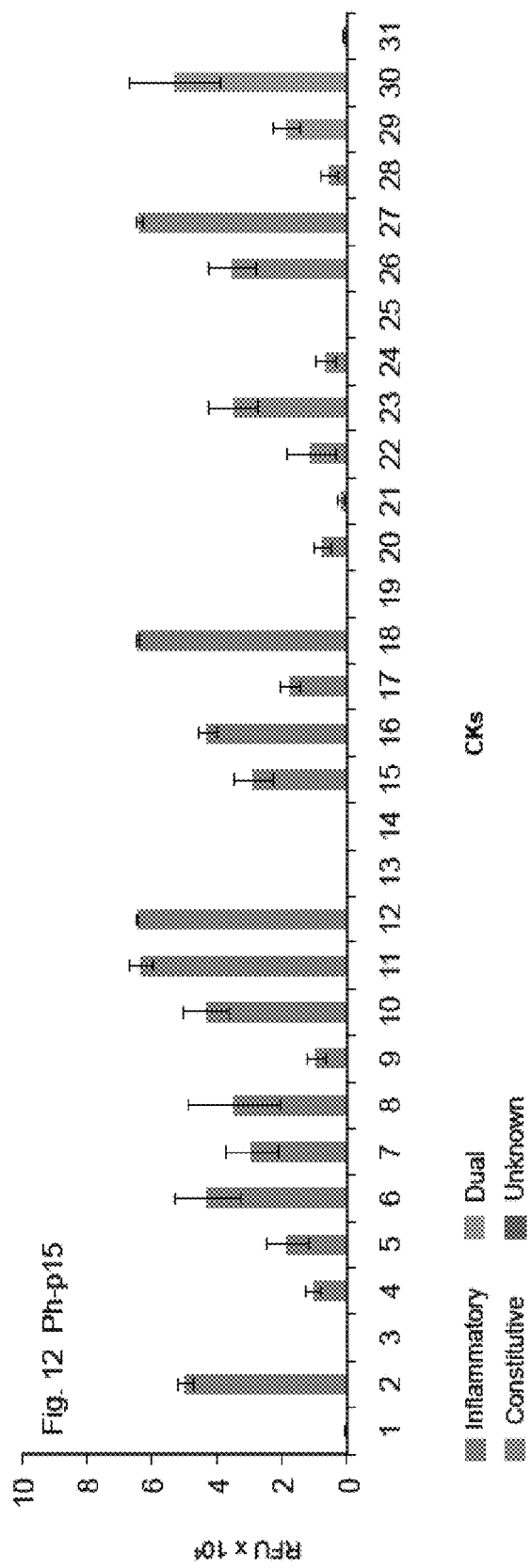
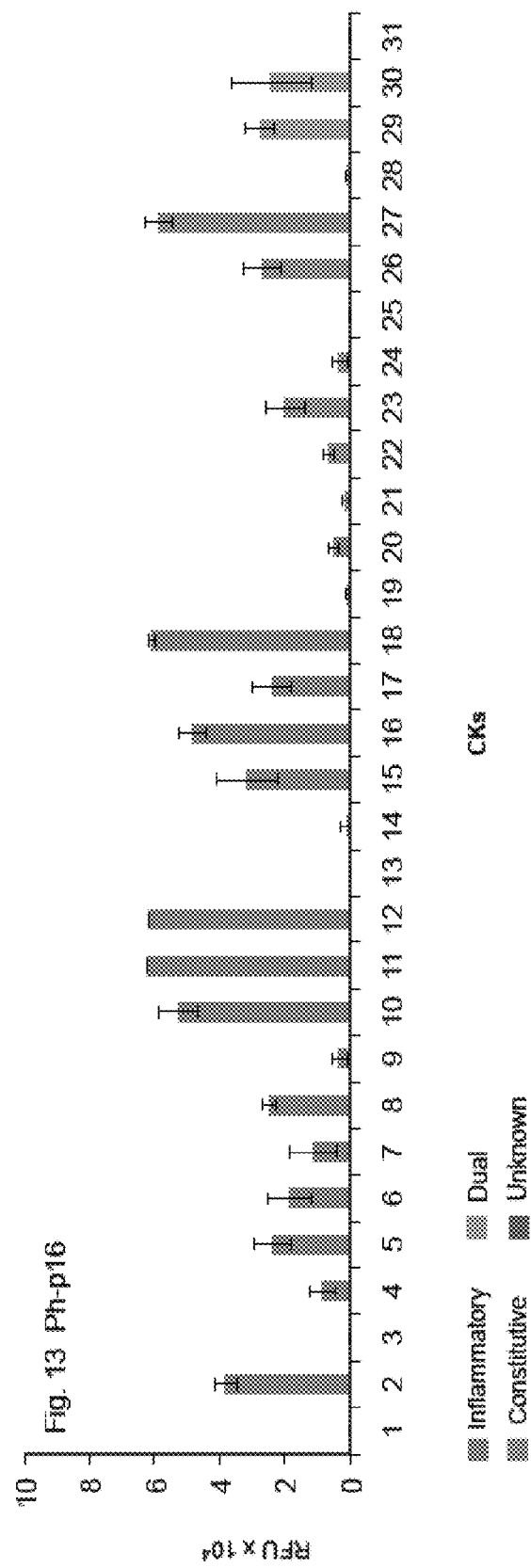

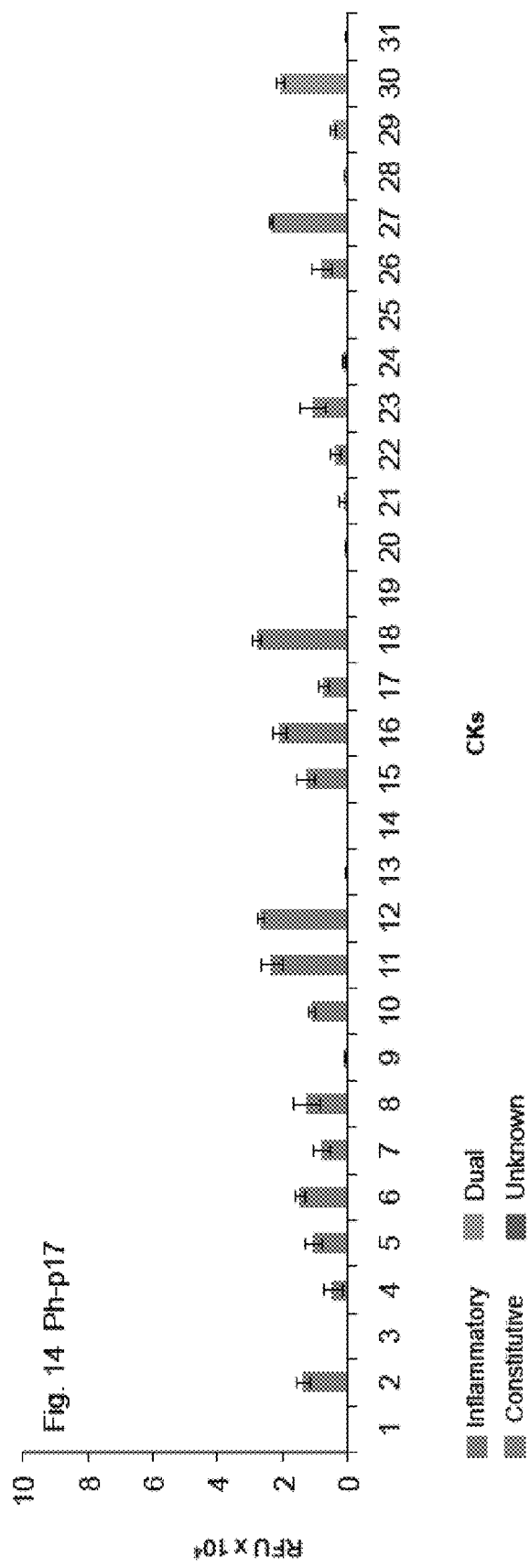
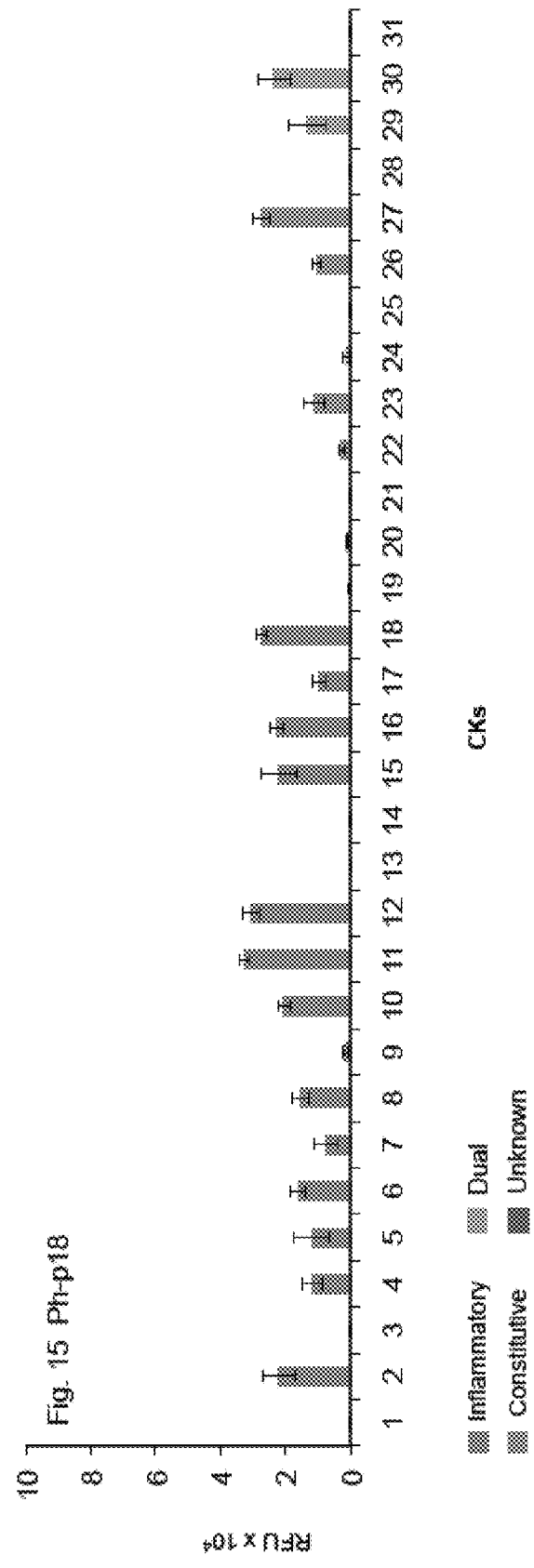

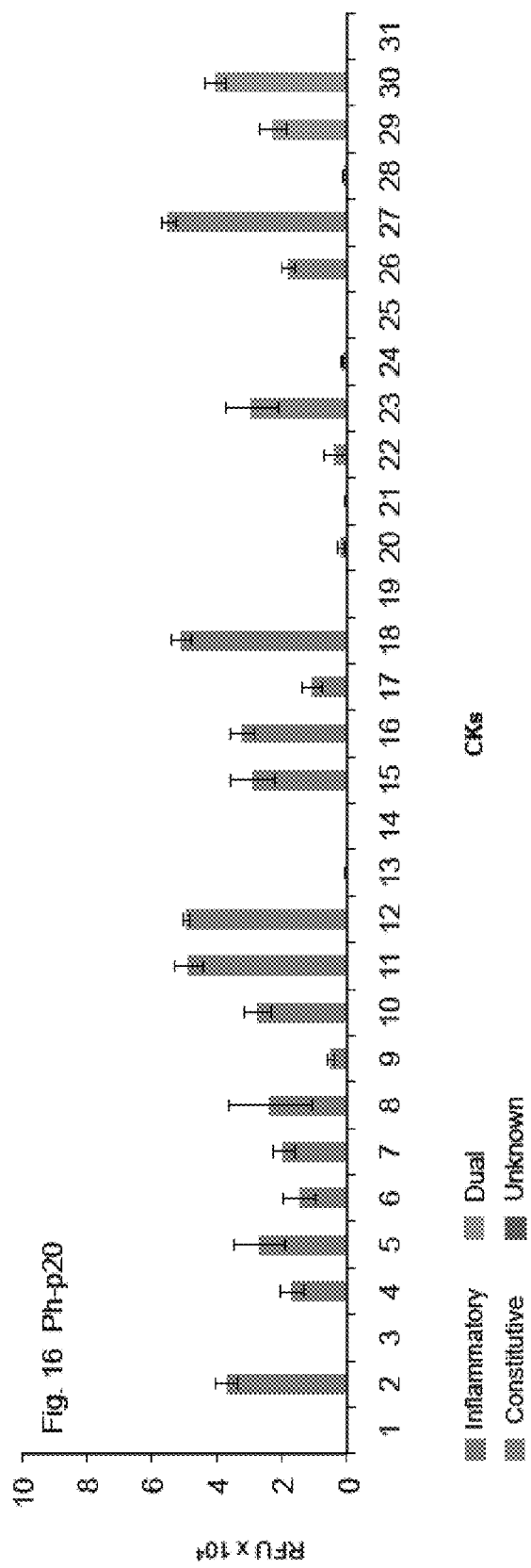
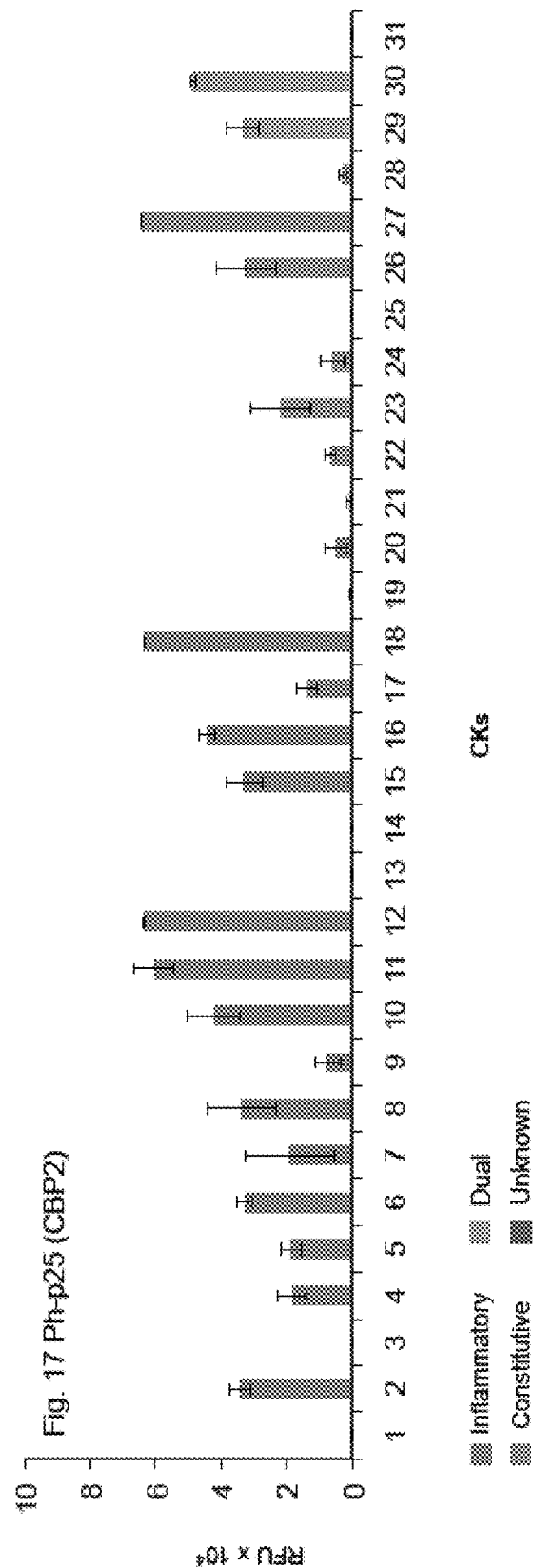

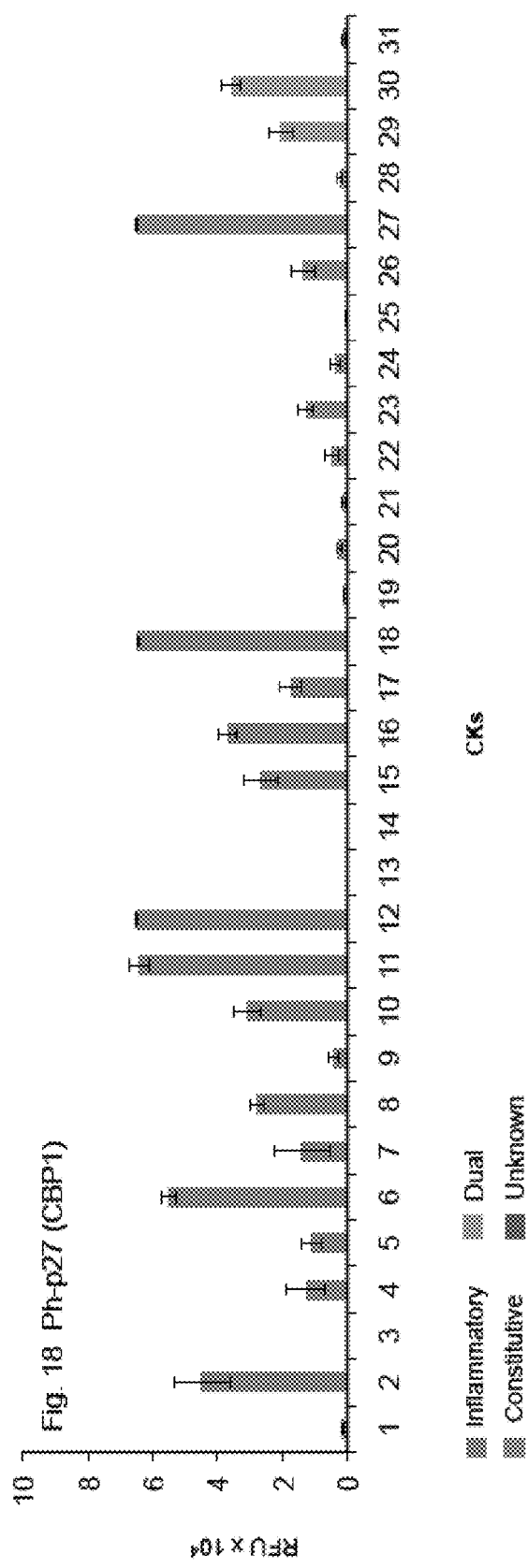
Fig. 18 Ph-p27 (CBP1)
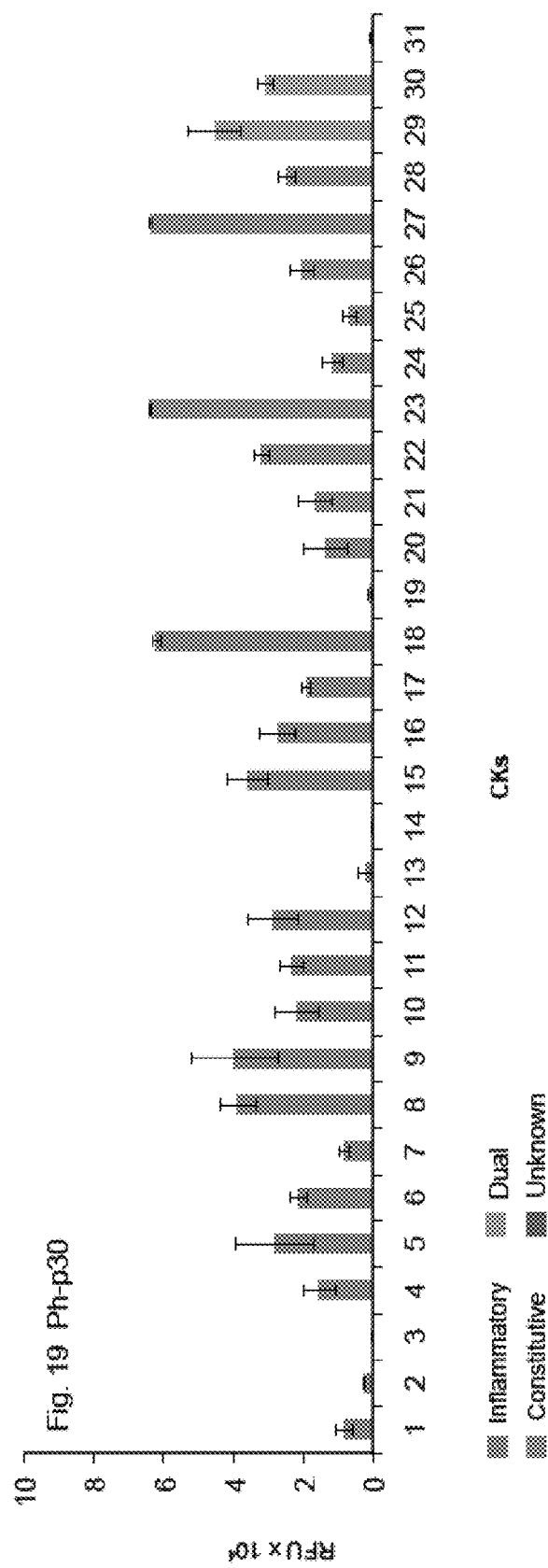
Fig. 19 Ph-p30

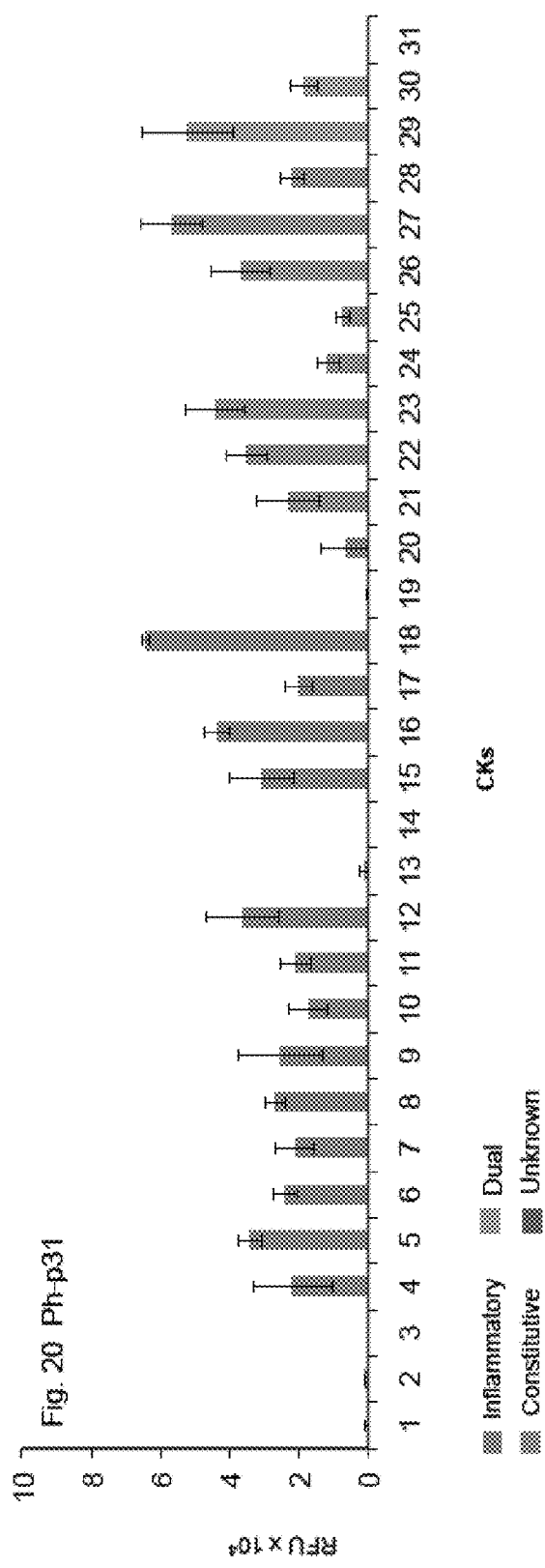
Fig. 20 Ph-p31
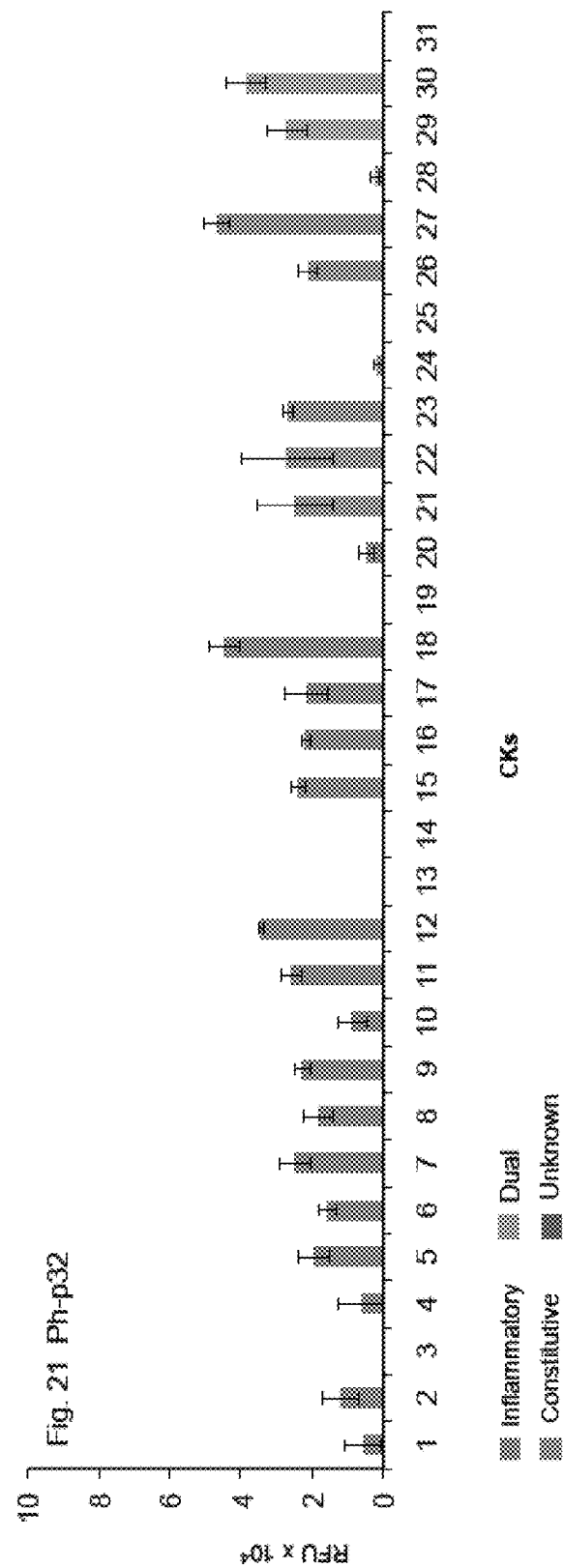
Fig. 21 Ph-p32

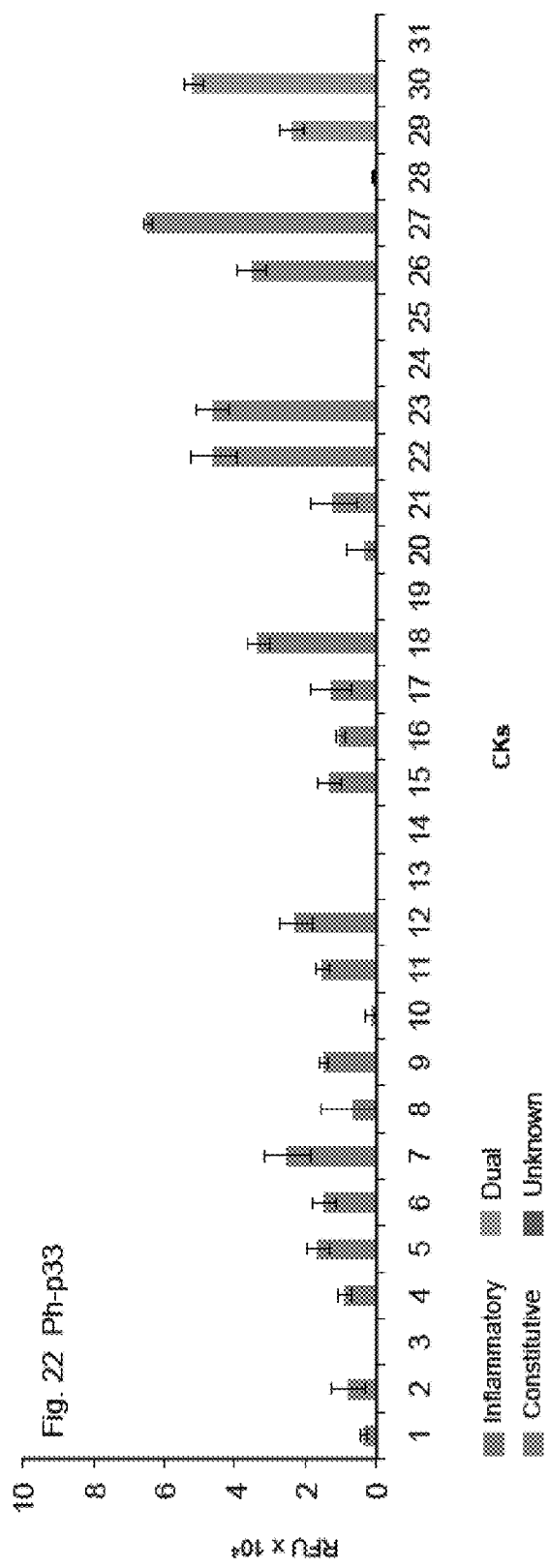
Fig. 22 Ph-p33
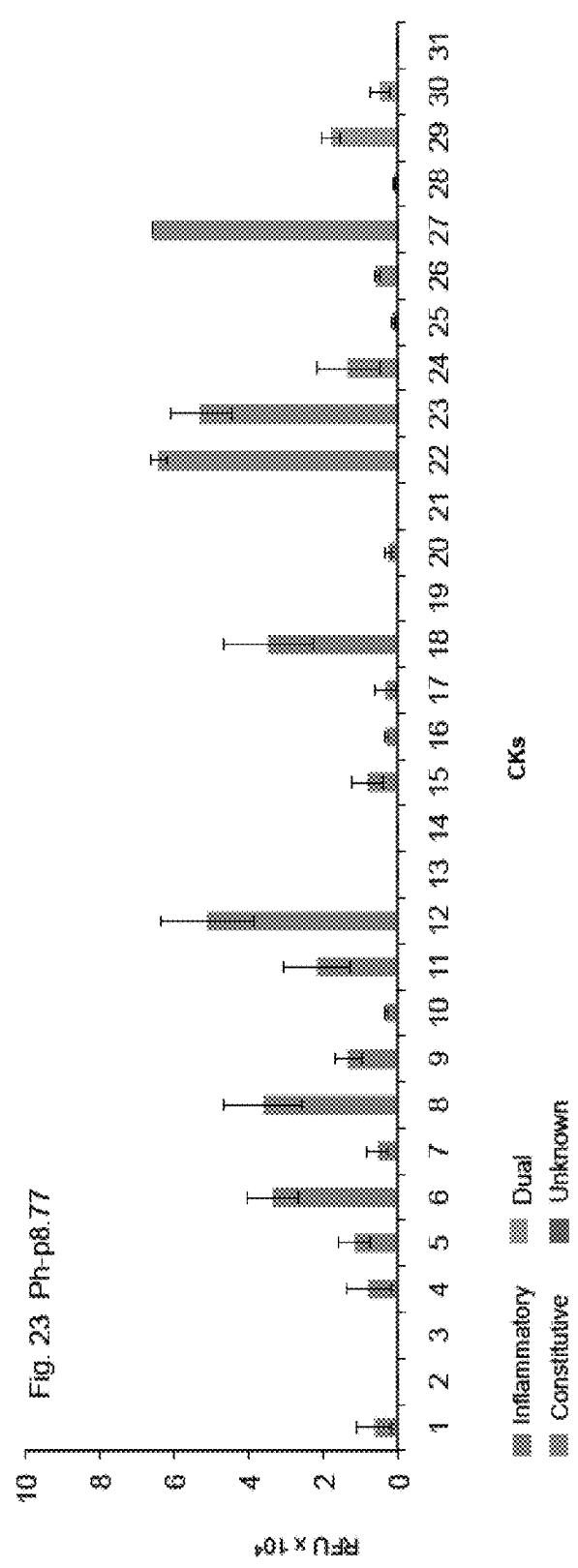
Fig. 23 Ph-p8.77

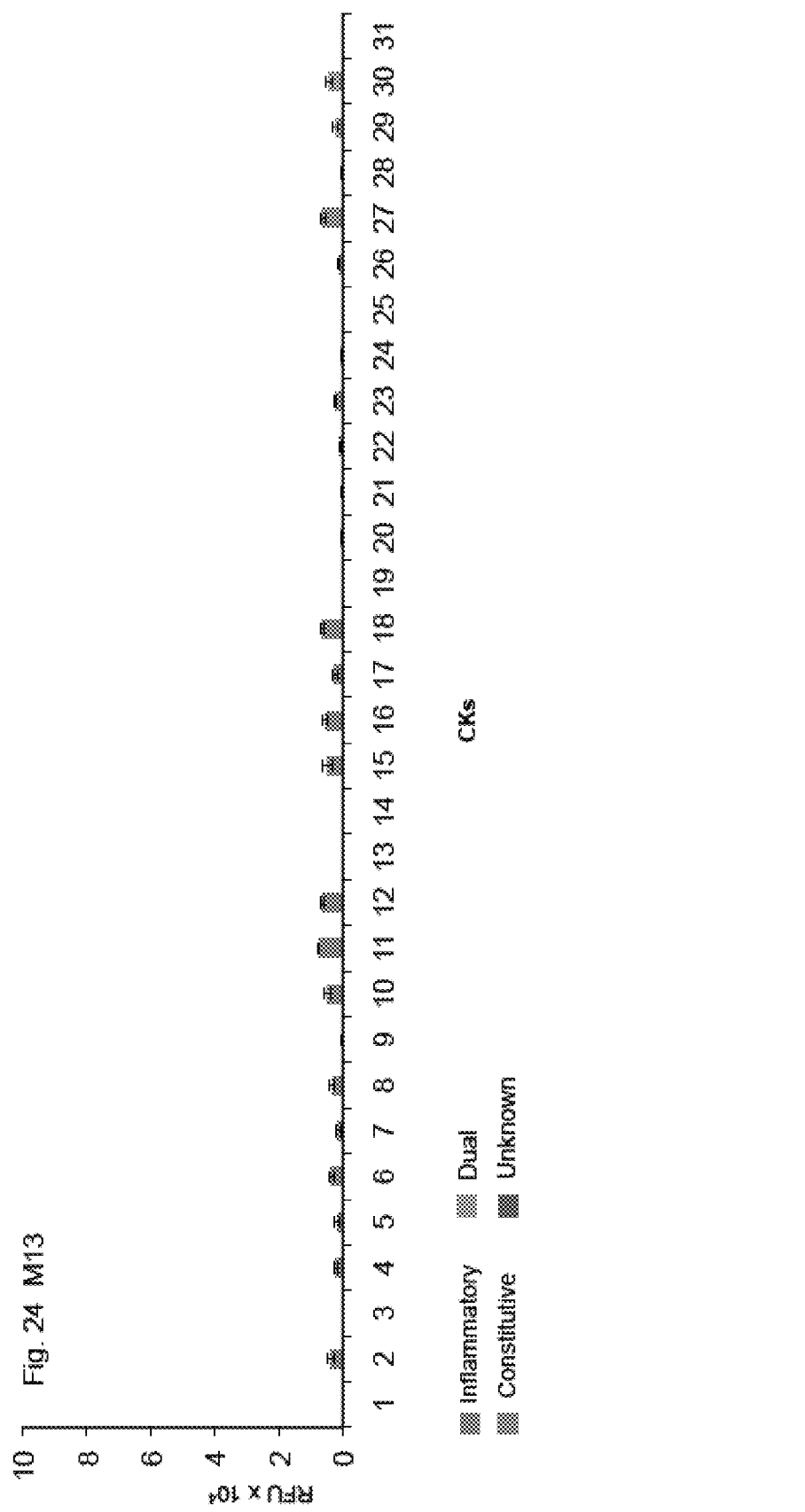

Figure. 27  P15 [ug]

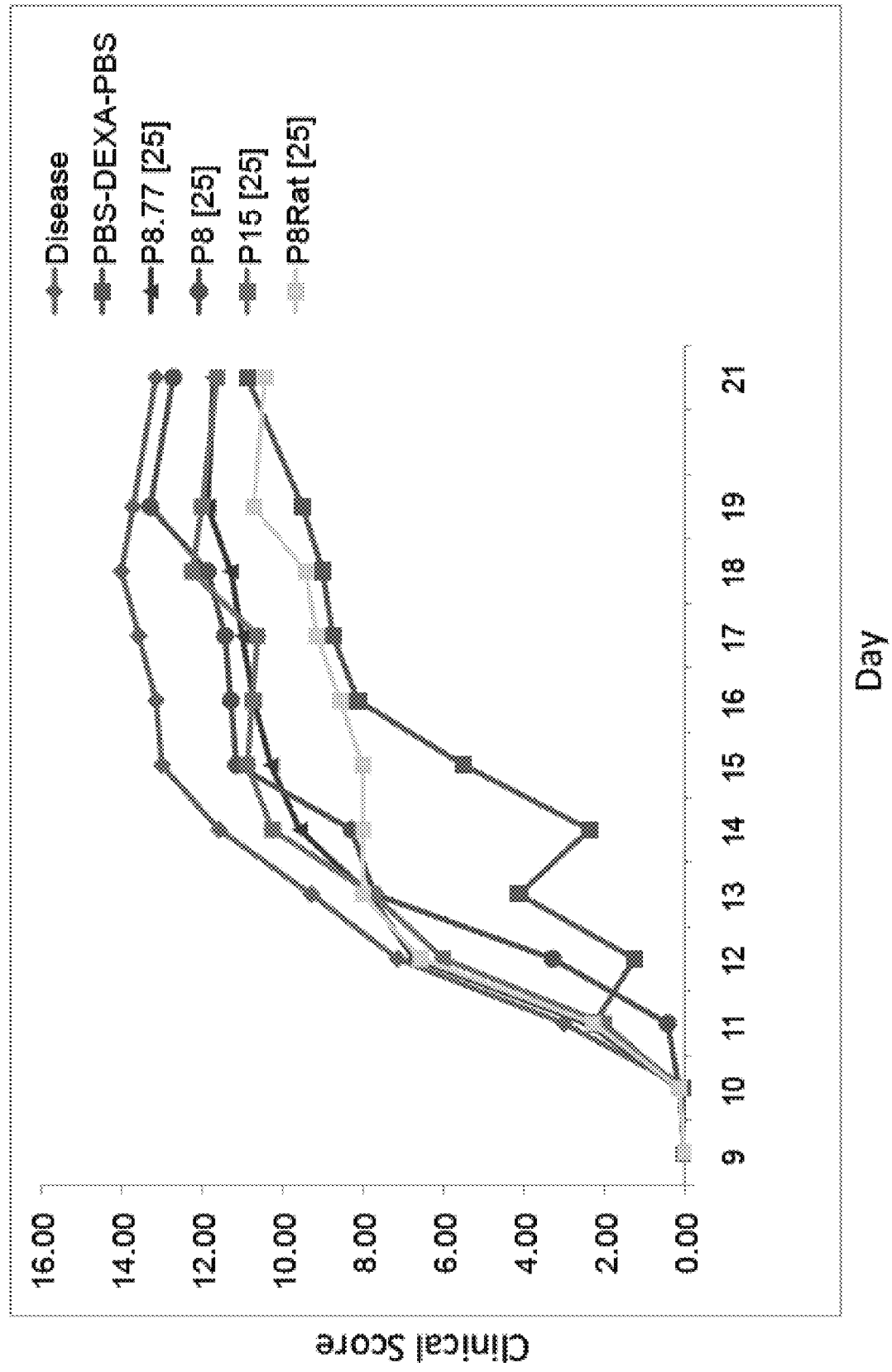
Figure. 31    P8.77, P8, P15, P8Rat [ug]

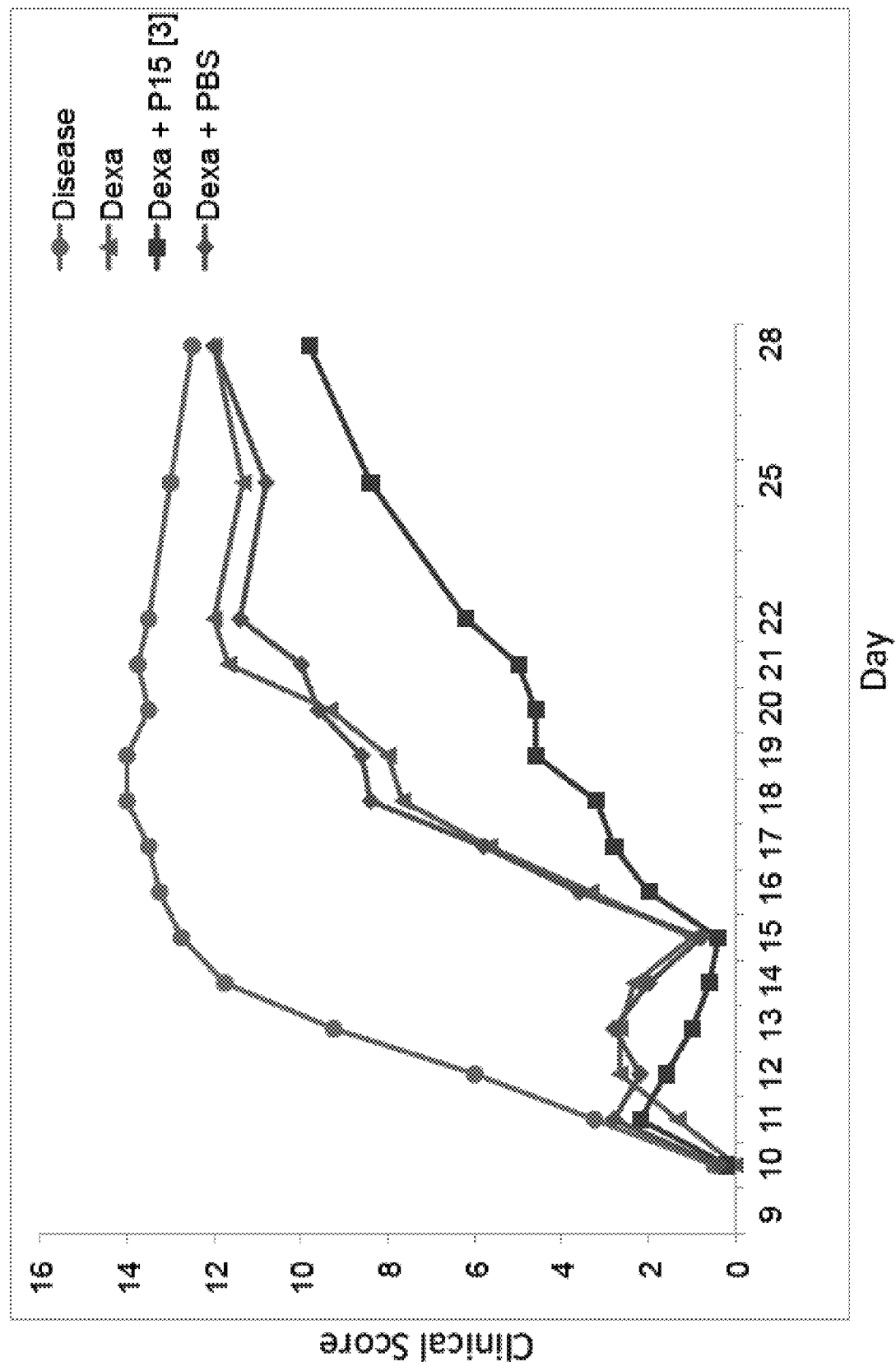

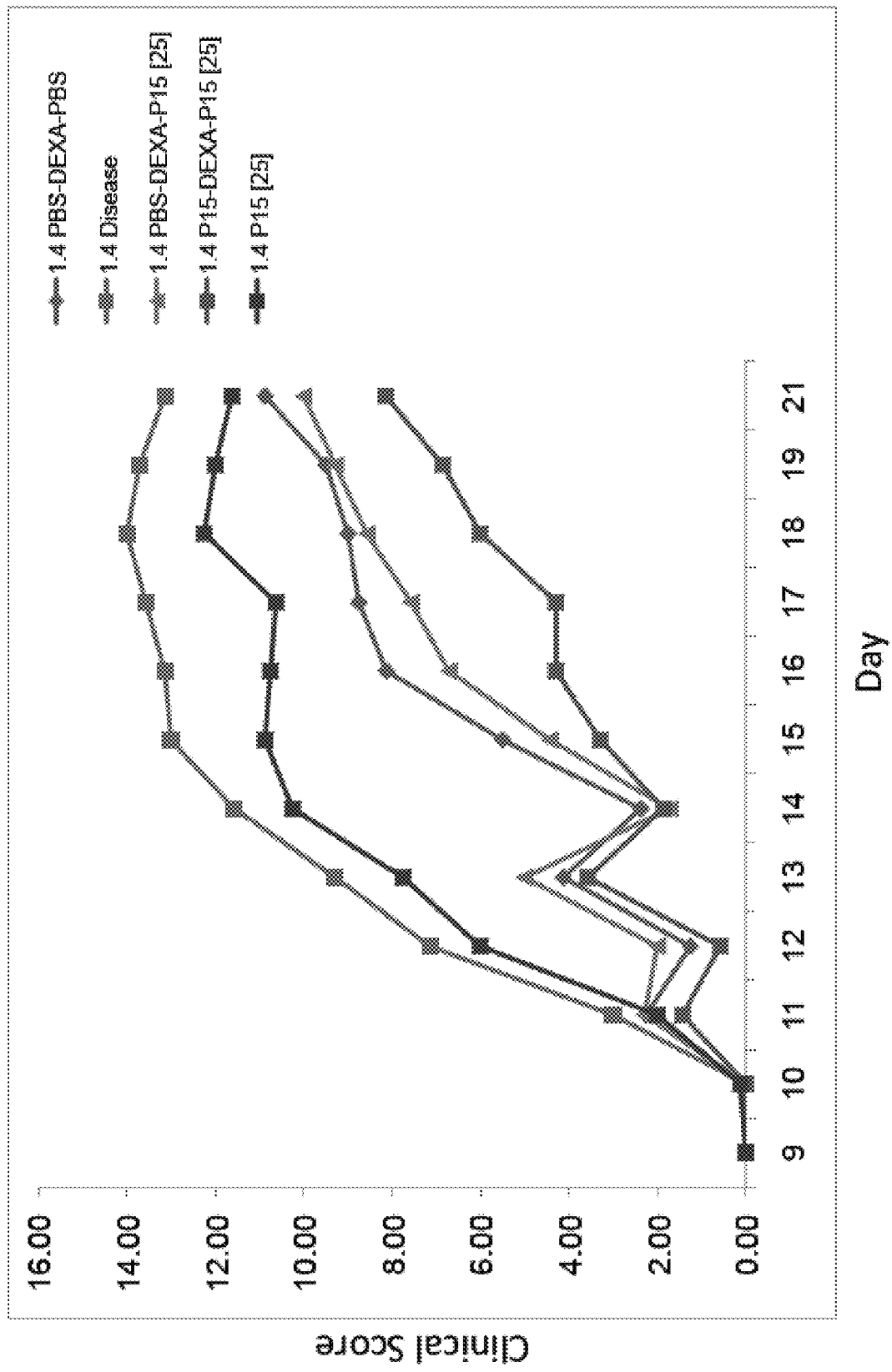
Figure. 33 Comparative Analysis of P15 Administration Protocols [ug].

PHARMACEUTICAL PEPTIDES FOR THE TREATMENT OF INFLAMMATORY DISEASES

RELATED APPLICATIONS

This application claims priority as a continuation-in-part of U.S. patent application Ser. No. 12/225,122, filed Sep. 15, 2008, which is the National Stage of International Application No. PCT/IL2007/000350, filed Mar. 18, 2007.

This application claims the benefit of priority to U.S. Provisional Application No. 61/195,691, filed Oct. 10, 2008.

FIELD

This application describes peptides and related compounds that modulate a plurality of chemokines and methods related thereto.

BACKGROUND

The pharmaceutical industry is struggling to provide efficacious drugs for serious, high incidence diseases such as diabetes, cancer, heart disease, arthritis and depression. One explanation is that drug discovery and development has been based on a misconceived strategy of one drug for one target. Single target drugs were selected for their high affinity to disease-related proteins and low cross reactivity with disease-unrelated proteins. Drugs were designed to be potent pharmacological agents with minimal side effects. The diseases in question, however, are now known to be multi-factorial. A therapeutic strategy that targets but one of multiple pathogenic factors cannot be expected to produce drugs of high efficacy. Another shortcoming of the strategy is that the robust biological networks that underpin both physiological and pathological processes have the capacity to compensate for individual drug-compromised proteins and circumvent drug-inactivated pathways.

It transpired that a number of successful medicines, although conceived as single target drugs, act on multiple disease-related proteins. The anti-depressant, Duloxetine, inhibits the uptake of two discrete neuropeptides, serotonin and noradrenaline. The anti-cancer drugs, Gleevec and Sutent, developed to inhibit the EGF receptor, were found to target multiple kinases. Atypical anti-psychotics, such as clozapine, act on a group of G-protein-coupled receptors (GPCRs) rather than on any single one. The efficacy of these medicines rests on their poly-pharmacology, their ability to modulate multiple disease-related targets.

Biological interactions in living organisms occur in the context of protein networks. Physiological processes are an expression of normal network activity, whereas aberrant network activity underlies patho-physiological processes. The efficacy of multi-target drugs derives from their ability to alter the overall activity of disease-associated networks. This is achieved by modifying the activities of multiple proteins of the network, as opposed to neutralizing the activity of any individual protein. In this way, they both pre-empt redundancy in the network and obviate the activation of alternative disease-associated pathways. In order to simultaneously modify multiple proteins, the drugs are preferably low affinity (Kd≥µM), rapid kinetic (1-100 $s^{-1}$), transient binding agents. Despite the contributions of Network Biology and Systems Biology, there is a paucity of information concerning low affinity protein-protein interactions and those weak affinity interactions that have been identified in databases include many false positives.

The pharmaceutical industry relies heavily on High Through-put Screening (HTS) of large molecular libraries to identify drug leads. Weakly binding compounds are difficult to detect in the low concentration (≤µM) libraries used for HTS because negligible amounts of low affinity compounds remain bound at equilibrium. The indirect detection methods employed by HTS, fluorescent and radioactive labeling, are inappropriate for evaluating weak binding events. False positive and negative results are inherent in the HTS of low affinity binding compounds, therefore, validation of genuine protein-protein interactions requires extensive retrospective theoretical and empirical analysis. The above difficulties are compounded for multiple-hit compounds. Unlike the single-target lead that binds strongly to its target, multi-target compounds preferably bind weakly to several targets. Yeast two-hybrid screening and affinity purification-mass spectrometry, are two additional methods used in drug discovery, but being essentially low through-put technologies, find limited use in the pharmaceutical industry.

Arthritis, multiple sclerosis and Crohn's disease are examples of polygenic, multi-factorial inflammatory diseases that are intractable to currently available treatments.

Laboratory research and clinical observations indicated that the expression of specific chemo-attractant cytokines, Chemokines (CKs), correlated with specific autoimmune diseases. The use of receptor antagonists and studies of CK receptor knock-out mice, validated CK receptors as drug targets. The CK receptors, CXCR1/2, CCR2, CX3CR1, CXCR3, CCR5 and CXCR4 and their respective cognate ligands are expressed at elevated levels in Rheumatoid Arthritis. Given that CKs and CK receptors constitute a network of interacting proteins, these validated drug targets are prime candidates for treatment with multi-target, low affinity drugs.

Peptides that interact with disease-related proteins, potential therapeutic agents, are generally identified by screening randomly generated peptide libraries. Although peptide-protein interactions are ubiquitous in nature, the high affinity binding peptides identified by library screening are inappropriate as regulators of physiological proteins. Peptides that function as regulators are preferably low affinity, transiently binding sequences that modulate, rather than negate protein activity. There is thus a need for a means to identify low affinity, transiently binding sequences that modulate physiological proteins such as CKs and CK receptors.

SUMMARY

The present invention is based on the experimental findings that specific amino acid sequences, originating in and abstracted from the CK regulatory domains of CK receptors, are capable of modulating immune system activity. The inventors have found that individual CK Receptor-Derived (CKRD) peptides can alter the course of an inflammatory disease induced in animals. In some embodiments, the individual CK receptor-derived peptides are derived from the extracellular domains of CK receptors. Preferred CK receptors include CXCR2, CCR2, CX3CR1, CXCR3, CCR5, CCR7, and CXCR4.

According to some embodiments, the CKRD peptides comprise the amino acid sequence of any one of SEQ ID NOs: 1-149. According to some embodiments, there is provided CKRD peptides and peptidic compounds that are 3 to 25 amino acids long comprising the amino acid sequence of any one of SEQ ID NOs: 1-149.

In some embodiments, there is provided CKRD peptides and peptidic compounds that are 3 to 25 amino acids long comprising the amino acid sequence of any one of SEQ ID NOs: 1-149, wherein one, two, three, or four amino acids have been substituted, deleted from, and/or inserted into the amino acid sequence. In still other preferred embodiments, the CKRD peptide or peptidic compounds have an amino acid sequence that is at least 60, 70, 80, 85, 90, 95, 98, 99, or 100% identical to any one of SEQ ID Nos. 1-149.

According to some embodiments, the CKRD peptides and peptidic compounds include at least 3, 4, 5, 6, 7, 8, or 9 consecutive amino acids of any one of the amino acid sequences of SEQ ID Nos. 1-149 and consist of between 3 and 25 amino acids.

According to some embodiments, the CKRD peptides and peptidic compounds are 3 to 25 amino acids in length and includes at least 4, 5, 6, 7, 8, 9, 10, 11, 12, or 13 amino acids from any one of the amino acid sequences of SEQ ID Nos. 1-149, as appropriate, wherein the at least 4, 5, 6, 7, 8, 9, 10, 11, 12, or 13 amino acids maintain their relative positions as they appear in the amino acid sequences of SEQ ID Nos. 1-149.

According to some embodiments, the CKRD peptides and peptidic compounds are non-covalent, low affinity modulators of disease-related CK activity. In preferred embodiments, the peptides and peptidic compounds display peptide binding with disease-related CKs in the micro-milli molar range.

According to some embodiments, there is provided peptidic compounds derived from the CKRD peptides of the present invention. Preferably, the peptidic compounds are structurally similar bioactive equivalents of the CKRD peptides of the present embodiments. The peptidic compounds are non-covalent, low affinity modulators of disease-related CK activity that preferably display binding with disease-related CKs in the micro-milli molar range.

According to some embodiments, there is provided pharmaceutical compositions comprising one or more CKRD peptide or peptidic compounds of the present invention and a pharmaceutically acceptable excipient. The pharmaceutical composition may be in any form suitable for administration. In a preferred embodiment, the pharmaceutical composition is in a form suitable for injection.

In a preferred embodiment, the peptide of the pharmaceutical composition comprises at least a portion of an extracellular domain of the receptor. In an even more preferred embodiment, the peptide of the pharmaceutical composition comprises at least a portion of a regulatory sequence of the receptor. In yet another embodiment, the pharmaceutical peptide is shown to interact specifically and differentially with multiple disease-related CKs in vitro.

According to some embodiments, the invention provides use of the pharmaceutical composition of the invention for altering immune system functioning, such as an autoimmune disease, multiple sclerosis, transplant rejection, psoriasis and asthma.

According to some embodiments, the invention provides CKRD peptides and peptidic compounds selected from (a) CKRD peptides and peptidic compounds comprising the amino acid sequence of any one of SEQ ID NO. 1-149, (b) a peptide or peptidic compound having at least 70% (e.g., at least 80%, 85%, 90%, or 95%, inclusive) sequence identity with a peptide of '(a)' and (c) a peptide of '(a)' or '(b)' wherein at least one amino acid has been chemically modified.

According to some embodiments, the invention provides for two or more peptides selected from (a) CKRD peptides and peptidic compounds comprising the amino acid sequence of any one of SEQ ID NO. 1-149, (b) a peptide or peptidic compound having at least 70% (e.g., at least 80%, 85%, 90%, or 95%, inclusive) sequence identity with a peptide of '(a)' and (c) a peptide of '(a)' or '(b)' wherein at least one amino acid has been chemically modified, when the peptides are administered in combination in the optimal molecular ratio.

According to some embodiments, the invention provides for a peptide to be used in a combination protocol with anti-inflammatory agents of other drug classes. The diseases targeted by the invention are, in the majority of cases, of a chronic, relapsing-remitting nature. It is highly probable that recipients of the therapeutic peptides of the invention will therefore have received, or be receiving drugs. The invention, therefore, provides for a peptide selected from (a) CKRD peptides and peptidic compounds comprising the amino acid sequence of any one of SEQ ID NO. 1-149, (b) a peptide or peptidic compound having at least 70% (e.g., at least 80%, 85%, 90%, or 95%, inclusive) sequence identity with a peptide of '(a)' and (c) a peptide of '(a)' or '(b)' wherein at least one amino acid has been chemically modified, when the peptide, or peptides are used in a combination protocol, simultaneously, or sequentially with an anti-inflammatory steroid, a non-steroidal anti-inflammatory agent, an immune modulator, or an immune suppressor.

The pharmaceutical compositions of the invention may be used to alter and modulate immune system functioning to treat autoimmune diseases specifically and inflammatory disorders in general. In some embodiments, there is provides methods of treating rheumatoid arthritis comprising administering to a subject in need thereof and therapeutically effective amount of one or more CKRD peptide or peptidic compounds of the present invention and a pharmaceutically acceptable excipient.

According to some embodiments, there is provided a method for identifying CKRD peptides or peptidic compounds comprising: selecting a candidate peptide containing from about 3 to about 25 amino acids derived from a chemokine receptor regulatory domain; and determining the ability of the candidate peptide to modulate the activity of disease-related chemokines.

BRIEF DESCRIPTION OF THE DRAWINGS

In order to understand the invention and to demonstrate how it may be carried out in practice, embodiments will now be described, by way of non-limiting example only, with reference to the accompanying drawings in which:

FIG. 1 shows the chemokine (CK) key to chemokine usage for FIGS. 2-24.
FIG. 2 shows CK binding of peptide 5.
FIG. 3 shows CK binding of Phage-presented peptide (Ph-p)28.
FIG. 4 shows CK binding of Ph-p8.1.
FIG. 5 shows CK binding of Ph-p8.4.
FIG. 6 shows CK binding of Ph-p8.6.
FIG. 7 shows CK binding of Ph-p8.7.
FIG. 8 shows CK binding of Ph-p8.8.
FIG. 9 shows CK binding of Ph-p8.11.
FIG. 10 shows CK binding of peptide 10.
FIG. 11 shows CK binding of Ph-p11.
FIG. 12 shows CK binding of Ph-p15.
FIG. 13 shows CK binding of Ph-p16.
FIG. 14 shows CK binding of Ph-p17.
FIG. 15 shows CK binding of Ph-p18.
FIG. 16 shows CK binding of Ph-p20.
FIG. 17 shows CK binding of Ph-p25.
FIG. 18 shows CK binding of Ph-p27.

FIG. 19 shows CK binding of Ph-p30.
FIG. 20 shows CK binding of Ph-p31.
FIG. 21 shows CK binding of Ph-p32.
FIG. 22 shows CK binding of Ph-p33.
FIG. 23 shows CK binding of Ph-p8.77.
FIG. 24 shows CK binding of M13 Phage.
FIG. 31 shows the effects of homologous native peptides administered to AIA rats.
FIG. 32 shows the effects of Dexamethasone and peptide 15 administered sequentially to AIA rats.
FIG. 33 shows the effects of different combination protocols using Dexamethasone and peptides to treat AIA rats.

DETAILED DESCRIPTION OF THE PREFERRED EMBODIMENTS

Figure 25A:
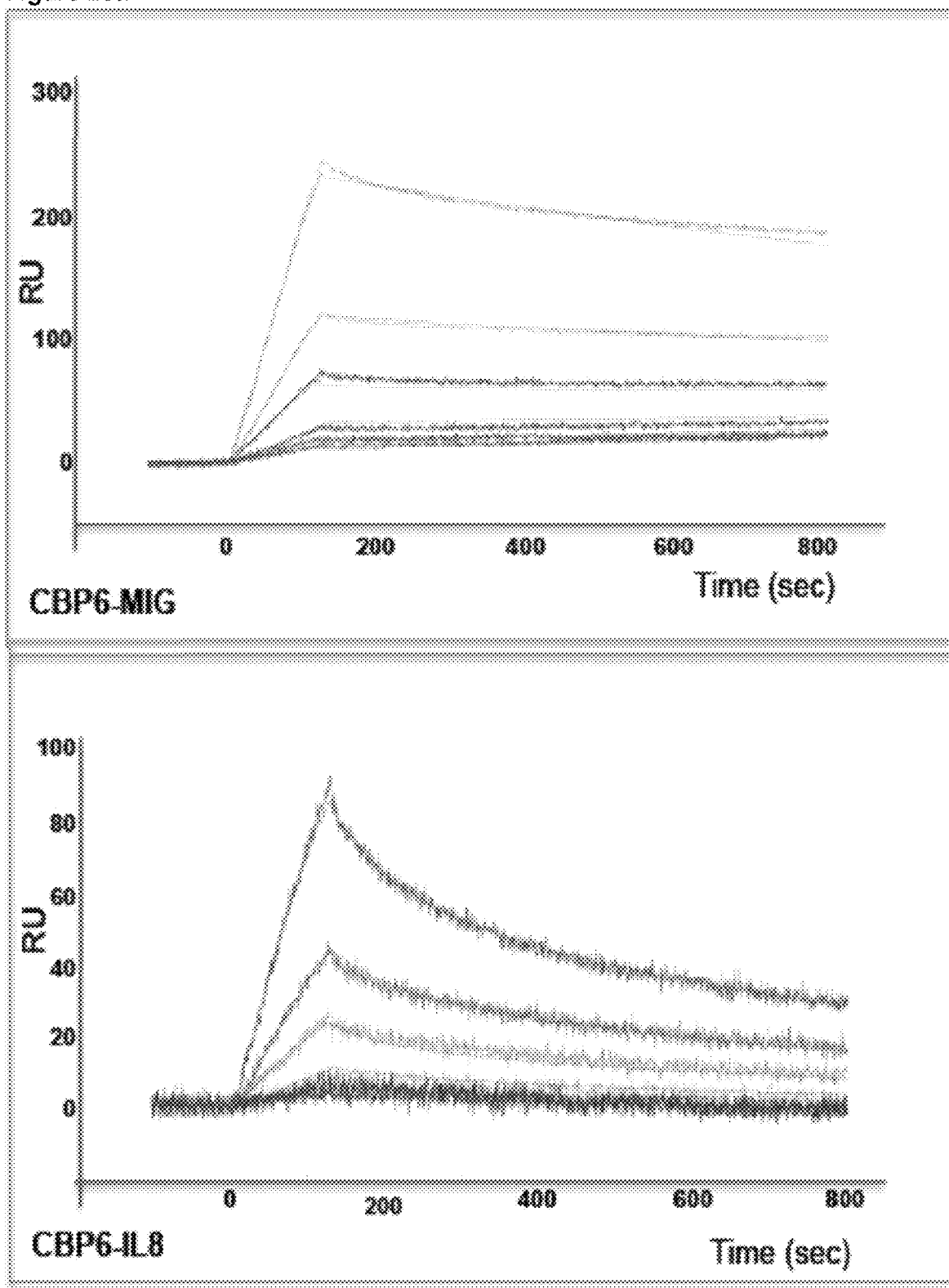
FIG. 25 shows Surface Plasmon Resonance analysis of peptide CB6R2 binding to the the CKs, Mig and IL8.

The present inventors have determined that CK ligand binding domains in the CK receptors contain regulatory sequences responsive to the multiple cognate and unrelated CKs of the CK network. The CK Receptor-Derived (CKRD) peptides and peptidic compounds of the present invention have the ability to modulate the activity of multiple cognate and unrelated chemokines, and more preferably, disease related chemokines that include, but are not limited to, Inflammatory CKs, Constitutive CKs, and Dual Function (Inflammatory and Constitutive) CKs.

According to some embodiments, the CKRD peptides comprise the amino acid sequence of any one of SEQ ID NO: 1-149. The CKRD peptides may be 3 to 25 amino acids in length and comprise the amino acid sequence of any one of SEQ ID NOs: 1-149, as appropriate.

In some embodiments, the CKRD peptide and related peptidic compounds have the formula $X_1$—C—$X_2$, where C comprises the amino acid sequence of any one of SEQ ID NO: 1-149, where $X_1$ and $X_2$ are each 0 to 21 amino acids in length, with the proviso that the total length of the peptide is no more than 25 amino acids. For example, where a CKRD peptide is 9 amino acid in length, as with SEQ ID NO: 8, the amino acid sequence of SEQ ID NO: 8 may be contained in larger amino acid sequence such as a peptide of 10 to 25 amino acids. In such an instance, the amino acid sequence of SEQ ID NO: 8 is referred to as the core sequence. A CKRD peptide comprising SEQ ID NO: 8 may therefore be represented by the following formula: $X_1$—C—$X_2$, where $X_1$ and $X_2$ are each 0 to 16 amino acids in length, wherein the total length of the peptide is no more than 25 amino acids. A CKRD peptide comprising the tri-peptide (e.g., DYD) may be represented by the following formula: $X_1$—C—$X_2$, where $X_1$ and $X_2$ are each 0 to 22 amino acids in length, wherein the total length of the peptide is no more than 25 amino acids. Accordingly, the maximum value of the sum of $X_1$ and $X_2$ may be determined by subtracting the length of the core sequence from the total length of the CKRD peptide. In preferred embodiments, the maximum value of the sum of $X_1$ and $X_2$ is selected from the group consisting of 0, 1, 2, 3, 4, 5, 6, 7, 8, 9, 10, 11, 12, 13, 14, 15, or 16.

The amino acids that make up the $X_1$ and $X_2$ components may be adaptor sequences, linking sequences, additional amino acids from the CK receptor (preferably from the regulatory region from which the CKRD peptide was derived), or other sequences. The sequence and length of the sequence is chosen so as not to significantly affect the activity of the core protein.

In some embodiments, the CKRD peptides are from 3 to 15 amino acids in length. This includes, for example, 3 to 12, 3 to 9, 3 to 7, 5 to 12, 5 to 9, 5 to 7, 7 to 13, 7 to 9, 9 to 15, 9 to 13, and 9 to 12.

In some embodiments, there is provided CKRD peptides and related peptidic compounds that comprise variants of the core sequence (C). In these embodiments, the CKRD peptides are 3 to 25 amino acids long comprising the amino acid sequence of any one of SEQ ID NOs: 1-149, as above, wherein one, two, three, or four amino acids have been substituted, deleted from, and/or inserted into the core amino acid sequence. In still other preferred embodiments, the core sequence of the CKRD peptide or peptidic compounds has an amino acid sequence that is at least 60, 70, 80, 85, 90, 95, 98, 99, or 100% identical to any one of SEQ ID Nos. 1-149.

According to some embodiments, the CKRD peptides and peptidic compounds are 3 to 25 amino acids in length and includes at least 4, 5, 6, 7, 8, 9, 10, 11, 12, or 13 amino acids from any one of the amino acid sequences of SEQ ID Nos. 1-149, as appropriate, wherein the at least 4, 5, 6, 7, 8, 9, 10, 11, 12, or 13 amino acids maintain their relative positions as they appear in the amino acid sequences of SEQ ID Nos. 1-149. In some embodiments, the at least 4, 5, 6, 7, 8, 9, 10, 11, 12, or 13 amino acids maintain their relative positions within the original length of the core sequence of one of SEQ ID Nos. 1-149.

Core sequences of the CKRD peptides are provided in the table below:

TABLE 1

Examples of core sequences of the CKRD peptides.

| Peptide | SEQ ID NO |
|---|---|
| GROUP I | |
| *(WVFGXXXCK)* | SEQ ID NO: 150 |
| WVFGHGMCK | SEQ ID NO: 2 |
| WVFGTFLCK | SEQ ID NO: 4 |
| WVFGNAMCK | SEQ ID NO: 5 |
| WVFGAAACK | SEQ ID NO: 8 |
| WVFGNAACK | SEQ ID NO: 9 |
| WVFGVHFCK | SEQ ID NO: 10 |
| WVFGAAMCK | SEQ ID NO: 11 |
| WVFGSGLCK | SEQ ID NO: 16 |
| WVFGHGMCK | SEQ ID NO: 22 |
| WVFGNMICK | SEQ ID NO: 27 |
| WVFGDAMCK | SEQ ID NO: 29 |
| WVFGNTMCK | SEQ ID NO: 30 |

TABLE 1-continued

Examples of core sequences of the CKRD peptides.

| Peptide | SEQ ID NO |
|---|---|
| WVFGSAMCK | SEQ ID NO: 31 |
| WVFGNGMCK | SEQ ID NO: 32 |
| WVFGNEMCK | SEQ ID NO: 33 |
| WVFSNAMCK | SEQ ID NO: 34 |
| WVFGNVMCK | SEQ ID NO: 35 |
| WVFGKAMCK | SEQ ID NO: 36 |
| WVFGTAMCK | SEQ ID NO: 37 |
| WTFGNAMCK | SEQ ID NO: 38 |
| WVFGNALCK | SEQ ID NO: 39 |
| WVFGGAMCK | SEQ ID NO: 40 |
| WIFGDAMCK | SEQ ID NO: 41 |
| WVFGNIMCK | SEQ ID NO: 42 |
| WIFGDAMCK | SEQ ID NO: 43 |
| WVFGNAACK | SEQ ID NO: 44 |
| HNAMCK | SEQ ID NO: 155 |
| WYFG | SEQ ID NO: 156 |
| WSLGSATCR | SEQ ID NO: 157 |
| WVFSNATCK | SEQ ID NO: 158 |
| WKFQTFMCK | SEQ ID NO: 159 |
| WIFGTFLCK | SEQ ID NO: 161 |
| WVFGQVMCK | SEQ ID NO: 160 |
| WVFS | SEQ ID NO: 45 |
| GNAMCK | SEQ ID NO: 6 |
| NAMCK | SEQ ID NO: 12 |
| GNSMCK | SEQ ID NO: 68 |
| GDAMCK | SEQ ID NO: 69 |
| GROUP II | |
| (-DYD-) | |
| DYDY | SEQ ID NO: 26 |
| DYDYG | SEQ ID NO: 25 |
| DYDYGAPC | SEQ ID NO: 24 |
| SYYDDVGL | SEQ ID NO: 1 |
| TTFFDYDYG | SEQ ID NO: 14 |
| NTTEDYDT | SEQ ID NO: 21 |
| SYYDDVGL | SEQ ID NO: 23 |
| TTFFYYDLQ | SEQ ID NO: 162 |
| VTTFFDYDYGAPC | SEQ ID NO: 28 |
| NTTEDYD | SEQ ID NO: 116 |
| TTEDYT | SEQ ID NO: 117 |
| NTTDNYDT | SEQ ID NO: 118 |
| DTTEDYET | SEQ ID NO: 119 |
| NTSENYDT | SEQ ID NO: 120 |
| NSTEDYD | SEQ ID NO: 121 |
| TTEDYET | SEQ ID NO: 122 |
| DYDYSAPC | SEQ ID NO: 123 |
| DYDYAAPC | SEQ ID NO: 124 |
| DYVLGDYGAPC | SEQ ID NO: 125 |
| DYEYAAPC | SEQ ID NO: 126 |
| DYEYGAP | SEQ ID NO: 127 |
| NYDYGAP | SEQ ID NO: 128 |
| DYDYSEPC | SEQ ID NO: 129 |
| DYDYGTP | SEQ ID NO: 130 |
| DYDYGGP | SEQ ID NO: 131 |
| DYDFGAP | SEQ ID NO: 132 |
| TTFFDYD | SEQ ID NO: 133 |
| VTTIFDYDYGAPC | SEQ ID NO: 134 |
| TTIYDYDYSAPC | SEQ ID NO: 135 |
| TTNYDYDYSAPC | SEQ ID NO: 136 |
| TFFDYDYIGA | SEQ ID NO: 137 |
| TTSYDYDYSEPC | SEQ ID NO: 138 |
| TTFYDYEFAQPC | SEQ ID NO: 139 |
| VTTFYIDYDY | SEQ ID NO: 140 |
| YYDDVGL | SEQ ID NO: 141 |
| SYYDDVG | SEQ ID NO: 142 |
| SYYDDVAL | SEQ ID NO: 143 |
| SYYDDVDL | SEQ ID NO: 144 |
| SYYDDLGL | SEQ ID NO: 145 |
| SYYDDVEL | SEQ ID NO: 146 |
| YYDDIGL | SEQ ID NO: 147 |
| SYYDDIG | SEQ ID NO: 148 |
| SYYDSVGL | SEQ ID NO: 149 |
| GROUP III | |
| (HXTCSXHFP) | SEQ ID NO: 151 |
| HHTCSLHFP | SEQ ID NO: 17 |
| SYTCSSHFP | SEQ ID NO: 18 |
| HRTCSLHFP | SEQ ID NO: 46 |

TABLE 1-continued

Examples of core sequences of the CKRD peptides.

| Peptide | SEQ ID NO |
|---|---|
| HYTCSLHFP | SEQ ID NO: 47 |
| HHTCSPHFP | SEQ ID NO: 48 |
| HFTCSLHFP | SEQ ID NO: 49 |
| HTTCSLHFP | SEQ ID NO: 50 |
| HHECSLHF | SEQ ID NO: 53 |
| TCSLHFP | SEQ ID NO: 51 |
| HHASSLHFP | SEQ ID NO: 52 |
| QHTCSPHFP | SEQ ID NO: 54 |
| HSCNLHFP | SEQ ID NO: 55 |
| HTCSPHFP | SEQ ID NO: 56 |
| HNTCSSHFP | SEQ ID NO: 61 |
| HRTCSPHFP | SEQ ID NO: 65 |
| HYTCSPHFP | SEQ ID NO: 66 |
| CSLHFP | SEQ ID NO: 63 |
| HSCSLHYP | SEQ ID NO: 57 |
| TCSLHFP | SEQ ID NO: 51 |
| TCTLHFP | SEQ ID NO: 59 |
| CSLHFP | SEQ ID NO: 63 |
| HTCNLHF | SEQ ID NO: 58 |
| HSCSLHF | SEQ ID NO: 60 |
| HTCSLQF | SEQ ID NO: 64 |
| HHSCSLH | SEQ ID NO: 62 |
| HHTCSL | SEQ ID NO: 67 |
| GROUP IV | |
| (LFGXXXCE) | SEQ ID NO: 152 |
| LFGNDCE | SEQ ID NO: 3 |
| FGNDCE | SEQ ID NO: 71 |
| LYGNDCE | SEQ ID NO: 72 |
| LFGSDCE | SEQ ID NO: 73 |
| LFNNDCE | SEQ ID NO: 75 |
| LFDNDCE | SEQ ID NO: 76 |
| LFGTDCE | SEQ ID NO: 77 |
| LFGNGCE | SEQ ID NO: 78 |
| LFGNDAACE | SEQ ID NO: 79 |
| LFGNDACE | SEQ ID NO: 80 |
| LFGNACE | SEQ ID NO: 81 |
| LFGNINDCE | SEQ ID NO: 82 |
| LFFVGNDCE | SEQ ID NO: 83 |

TABLE 1-continued

Examples of core sequences of the CKRD peptides.

| Peptide | SEQ ID NO |
|---|---|
| LFGYDCE | SEQ ID NO: 84 |
| LFGNECE | SEQ ID NO: 70 |
| LFGDECE | SEQ ID NO: 85 |
| MFGNECE | SEQ ID NO: 86 |
| FGNECE | SEQ ID NO: 87 |
| FGNNCE | SEQ ID NO: 89 |
| FGDDCE | SEQ ID NO: 90 |
| FFGLNNC | SEQ ID NO: 13 |
| LFGNDC | SEQ ID NO: 74 |
| LYGNDCD | SEQ ID NO: 88 |
| LFGNDSE | SEQ ID NO: 91 |
| GROUP V | |
| (KCQXXXSVY) | SEQ ID NO: 153 |
| HCQNEISVY | SEQ ID NO: 95 |
| KCQVPEDSVY | SEQ ID NO: 96 |
| KCQKEESIVY | SEQ ID NO: 97 |
| KCQKGDSV | SEQ ID NO: 98 |
| KCQKGDTVY | SEQ ID NO: 99 |
| KCLKEDSIY | SEQ ID NO: 100 |
| KCQKENLVY | SEQ ID NO: 101 |
| KCQKEFDISVY | SEQ ID NO: 111 |
| TKSQKEDFLESEKESVY | SEQ ID NO: 112 |
| TKCQKE | SEQ ID NO: 20 |
| TKCQKEDSVY | SEQ ID NO: 92 |
| TKCQKEN | SEQ ID NO: 93 |
| TKCEKED | SEQ ID NO: 94 |
| KCQKEDS | SEQ ID NO: 106 |
| KCQKEFDISVY | SEQ ID NO: 111 |
| QKEDSVY | SEQ ID NO: 102 |
| QKDDSVY | SEQ ID NO: 103 |
| CQKADAVY | SEQ ID NO: 104 |
| CQKEDSV | SEQ ID NO: 105 |
| CQKGDSVY | SEQ ID NO: 110 |
| QKEDSVY | SEQ ID NO: 107 |
| EDSVY | SEQ ID NO: 15 |
| CQKEDQVY | SEQ ID NO: 108 |
| CEKEDSIY | SEQ ID NO: 109 |

TABLE 1-continued

Examples of core sequences of the CKRD peptides.

| Peptide | SEQ ID NO |
|---|---|
| GROUP VI | |
| (DRYLXXVHAT) | SEQ ID NO: 154 |
| DRYLNIVHAT | SEQ ID NO: 19 |
| DRYLNIVHA | SEQ ID NO: 113 |
| DRYLSIVHAT | SEQ ID NO: 114 |
| DRYLAIVHAT | SEQ ID NO: 115 |

According to some embodiments, the CKRD peptides and peptidic compounds include at least 3, 4, 5, 6, 7, 8, 9, 10, 11, 12, or 13 consecutive amino acids of any one of the amino acid sequences of SEQ ID Nos. 1-149 and consist of between 3 and 25 amino acids, inclusive.

Group 1

According to some embodiments, a CKRD peptide or peptidic compound comprises an amino acid sequence of WVFGX$_a$X$_b$X$_c$CK (SEQ ID NO: 150), where X$_a$, X$_b$, and X$_c$ are each any amino acid or none. In some embodiments, X$_a$ may be H, T, N, A, G, D, E, K, V, S, or none. In some embodiments, X$_b$ may be F, H, M, T, I, A, G, D, E, K, V, S, or none. In some embodiments, X$_c$ may be M, L, A, G, F, I, or none. Preferably, the CKRD peptide or peptidic compound is between 6 to 25 amino acids in length as described herein elsewhere. For example, in some embodiments, a CKRD peptide or peptidic compound may comprise the amino acid sequence of any one of SEQ ID NOs: 2, 4, 5, 8, 9, 10, 11, 16, 22, 27, 29-44, 158, and 160 wherein the peptide is 9 to 25 amino acids in length.

According to some embodiments, a CKRD peptide or peptidic compound may be described by the formula X$_1$—C—X$_2$, where C is derived from the amino acid sequence of WVFGX$_a$X$_b$X$_c$CK (SEQ ID NO: 150), where X$_1$ and X$_2$ are each 0 to 16 amino acids in length, wherein the total length of the peptide is no more than 25 amino acids. The maximum value of the sum of X$_1$ and X$_2$ may be 0, 1, 2, 3, 4, 5, 6, 7, 8, 9, 10, 11, 12, 13, 14, 15, or 16.

According to some embodiments, a CKRD peptide or peptidic compound derived from the amino acid sequence of any one of SEQ ID NOs: 2, 4, 5, 8, 9, 10, 11, 16, 22, 27, 29-44, and 155-161 wherein the amino acid sequence comprises a core sequence of at least 4, 5, 6, 7, or 8 amino acids from SEQ ID NOs: 2, 4, 5, 8, 9, 10, 11, 16, 22, 27, 29-44, and 155-161, where the at least 4, 5, 6, 7, 8, or 9 amino acids maintain their relative positions as they appear in SEQ ID NOs: 2, 4, 5, 8, 9, 10, 11, 16, 22, 27, 29-44, and 155-161. In some embodiments, the CKRD peptide or peptidic compound is between 6 to 25 amino acids in length, as described herein elsewhere, and the at least 4, 5, 6, 7, 8, or 9 amino acids maintain their relative positions as they appear in SEQ ID NOs: 2, 4, 5, 8, 9, 10, 11, 16, 22, 27, 29-44, and 155-161 over the span of 9 or 10 amino acids. For example, a CKRD peptide or peptidic compound may be derived from the amino acid sequence of SEQ ID NO: 16 where the at least 4, 5, 6, 7, or 8 amino acids maintain their relative positions as they appear in SEQ ID NO: 16, where the at least 4, 5, 6, 7, or 8 amino acids maintain their relative positions as they appear in SEQ ID NO: 16 over the span of 9 amino acids.

In some embodiments, a CKRD peptide or peptidic compound may be described by the formula X$_1$—C—X$_2$, where C is derived from the amino acid sequence of any one of SEQ ID NOs: 2, 4, 5, 8, 9, 10, 11, 16, 22, 27, 29-44, and 155-161, wherein said amino acid sequence is 6, 7, 8, or 9 amino acids in length, wherein said amino acid sequence comprises at least 4, 5, 6, 7, or 8 amino acids from any one of SEQ ID NOs: 2, 4, 5, 8, 9, 10, 11, 16, 22, 27, 29-44, and 155-161, and wherein said at least 4, 5, 6, 7, or 8 amino acids maintain their relative positions as they appear in any one of SEQ ID NOs: 2, 4, 5, 8, 9, 10, 11, 16, 22, 27, 29-44, and 155-161; where X$_1$ and X$_2$ are each 0 to 16 amino acids in length, wherein the total length of the peptide is no more than 25 amino acids. The sum of X$_1$ and X$_2$ may be 0, 1, 2, 3, 4, 5, 6, 7, 8, 9, 10, 11, 12, 13, 14, 15, or 16. In some embodiments, the at least 6 amino acids are W, V, F, G, C, and K.

Group 2

According to some embodiments, a CKRD peptide or peptidic compound is provided comprising the amino acid sequence D-Y-D, wherein the CKRD peptide or peptidic compound is between 3 to 25 (e.g., 3 to 20, 3 to 15, 3 to 9, etc.) amino acids in length.

According to some embodiments, a CKRD peptide or peptidic compound is provided comprising the amino acid sequence of any one of SEQ ID NO: 1, 14, 21, 23-26, 28, 116-149, and 162, wherein the CKRD peptide or peptidic compound is between 3 to 25 (e.g., 3 to 20, 3 to 15, 3 to 9, etc.) amino acids in length.

According to some embodiments, a CKRD peptide or peptidic compound is provided comprising the amino acid sequence D-Y-D-X, wherein X is Y or T, and wherein the CKRD peptide or peptidic compound is between 4 to 25 (e.g., 4 to 20, 4 to 15, 4 to 9, etc.) amino acids in length.

According to some embodiments, a CKRD peptide or peptidic compound is provided comprising the amino acid sequence X1-Y-D-X2, wherein X1 is D, Y, or N, wherein X2 is D or Y, and wherein the CKRD peptide or peptidic compound is between 4 to 25 (e.g., 4 to 20, 4 to 15, 4 to 9, etc.) amino acids in length.

According to some embodiments, a CKRD peptide or peptidic compound is provided comprising the amino acid sequence X—Y—Y-D-D, wherein X is S or none, and wherein the CKRD peptide or peptidic compound is between 4 to 25 (e.g., 5 to 20, 5 to 15, 5 to 9, etc.) amino acids in length.

According to some embodiments, a CKRD peptide or peptidic compound is provided comprising the amino acid sequence S—Y—Y-D-X, wherein X is S or none, and wherein the CKRD peptide or peptidic compound is between 4 to 25 (e.g., 5 to 20, 5 to 15, 5 to 9, etc.) amino acids in length.

A CKRD peptide or peptidic compound comprising the amino acid sequence D-Y-D-X-G, wherein X is Y or T, and wherein the CKRD peptide or peptidic compound is between 5 to 25 (e.g., 5 to 20, 5 to 15, 5 to 9, etc.) amino acids in length.

Group 3

According to some embodiments, a CKRD peptide or peptidic compound comprises an amino acid sequence of HX$_a$TCSX$_b$HFP (SEQ ID NO: 151), where X$_a$ and X$_b$ are each any amino acid or none. In some embodiments, X$_a$ may be H, T, N, R, Y, F, or none. In some embodiments, X$_b$ may be L, S, P, or none. Preferably, the CKRD peptide or peptidic compound is between 7 to 25 amino acids in length as described herein elsewhere. For example, in some embodiments, a CKRD peptide or peptidic compound may comprise the amino acid sequence of any one of SEQ ID NOs: 17, 18, and 46-50, 56, 61, 65, and 66.

According to some embodiments, a CKRD peptide or peptidic compound may be described by the formula $X_1$—C—$X_2$, where C is derived from the amino acid sequence of $HX_aTCSX_bHFP$ (SEQ ID NO: 151), where $X_1$ and $X_2$ are each 0 to 16 amino acids in length, wherein the total length of the peptide is no more than 25 amino acids. In some embodiments, $X_a$ may be H, Y, R, F, N, or none. In some embodiments, $X_b$ may be L, S, P, or none. The maximum value of the sum of $X_1$ and $X_2$ may be 0, 1, 2, 3, 4, 5, 6, 7, 8, 9, 10, 11, 12, 13, 14, 15, or 16.

According to some embodiments, a CKRD peptide or peptidic compound derived from the amino acid sequence of any one of any one of SEQ ID NOs: 17, 18, and 46-67, wherein the amino acid sequence comprises a core sequence of at least 4, 5, 6, 7, 8 or 9 amino acids from any one of SEQ ID NOs: 17, 18, and 46-67, where the at least 4, 5, 6, 7, 8 or 9 amino acids maintain their relative positions as they appear in any one of SEQ ID NOs: 17, 18, and 46-67. In some embodiments, the CKRD peptide or peptidic compound is between 6 to 25 amino acids in length, as described herein elsewhere, and the at least 4, 5, 6, 7, 8 or 9 amino acids maintain their relative positions as they appear in any one of SEQ ID NOs: 17, 18, and 46-67 over the span of 9 or 10 amino acids. For example, a CKRD peptide or peptidic compound may be derived from the amino acid sequence of SEQ ID NO: 17 where the at least 4, 5, 6, 7, or 8 amino acids maintain their relative positions as they appear in SEQ ID NO: 17, where the at least 4, 5, 6, 7, or 8 amino acids maintain their relative positions as they appear in SEQ ID NO: 17 over the span of 9 amino acids.

In some embodiments, a CKRD peptide or peptidic compound may be described by the formula $X_1$—C—$X_2$, where C is derived from the amino acid sequence of any one of SEQ ID NOs: 17, 18, and 46-67, wherein said amino acid sequence is 6, 7, 8, or 9 amino acids in length, wherein said amino acid sequence comprises at least 4, 5, 6, 7, 8 or 9 amino acids from any one of SEQ ID NOs: 17, 18, and 46-67, and wherein said at least 4, 5, 6, 7, 8 or 9 amino acids maintain their relative positions as they appear in any one of SEQ ID NOs: 17, 18, and 46-67; where $X_1$ and $X_2$ are each 0 to 16 amino acids in length, wherein the total length of the peptide is no more than 25 amino acids. The sum of $X_1$ and $X_2$ may be 0, 1, 2, 3, 4, 5, 6, 7, 8, 9, 10, 11, 12, 13, 14, 15, or 16.

In some embodiments, a CKRD peptide or peptidic compound may be described by the formula $X_1$—C—$X_2$, where C is derived from the amino acid sequence of HHTCSLHFP (SEQ ID NO: 17), wherein said amino acid sequence is 9 amino acids in length, wherein said amino acid sequence comprises at least 6, 7, or 8 amino acids from HHTCSLHFP (SEQ ID NO: 17), and wherein said at least 6, 7, or 8 amino acids maintain their relative positions as they appear in HHTCSLHFP (SEQ ID NO: 17); where $X_1$ and $X_2$ are each 0 to 16 amino acids in length, wherein the total length of the peptide is no more than 25 amino acids. The sum of $X_1$ and $X_2$ may be 0, 1, 2, 3, 4, 5, 6, 7, 8, 9, 10, 11, 12, 13, 14, 15, or 16.

In some embodiments, a CKRD peptide or peptidic compound may be described by the formula $X_1$—C—$X_2$, where C is derived from the amino acid sequence of HYTCSSHFP (SEQ ID NO: 18), wherein said amino acid sequence is 9 amino acids in length, wherein said amino acid sequence comprises at least 6, 7, or 8 amino acids from HYTCSSHFP (SEQ ID NO: 18), and wherein said at least 6, 7, or 8 amino acids maintain their relative positions as they appear in HYTCSSHFP (SEQ ID NO: 18); where $X_1$ and $X_2$ are each 0 to 16 amino acids in length, wherein the total length of the peptide is no more than 25 amino acids. The sum of $X_1$ and $X_2$ may be 0, 1, 2, 3, 4, 5, 6, 7, 8, 9, 10, 11, 12, 13, 14, 15, or 16.

Group 4

According to some embodiments, a CKRD peptide or peptidic compound comprises an amino acid sequence of $LFGX_aX_bX_cCE$ (SEQ ID NO: 152), where $X_a$, $X_b$, and $X_c$ are each any amino acid or none. In some embodiments, $X_a$ may be N, S, T, Y, D, E, or none. In some embodiments, $X_b$ may be D, G, A, E, or none. In some embodiments, $X_c$ may be G, A, or none. Preferably, the CKRD peptide or peptidic compound is between 6 to 25 amino acids in length as described herein elsewhere. For example, in some embodiments, a CKRD peptide or peptidic compound may comprise the amino acid sequence of any one of SEQ ID NOs: 3, 70, 73, 77, 78, 80, 81, 84, and 85 wherein the peptide is 9 to 25 amino acids in length.

According to some embodiments, a CKRD peptide or peptidic compound may be described by the formula $X_1$—C—$X_2$, where C is derived from the amino acid sequence of $LFGX_aX_bX_cCE$ (SEQ ID NO: 152), where $X_1$ and $X_2$ are each 0 to 16 amino acids in length, wherein the total length of the peptide is no more than 25 amino acids. The maximum value of the sum of $X_1$ and $X_2$ may be 0, 1, 2, 3, 4, 5, 6, 7, 8, 9, 10, 11, 12, 13, 14, 15, or 16.

According to some embodiments, a CKRD peptide or peptidic compound derived from the amino acid sequence of any one of SEQ ID NOs: 3, 13, and 71-91, wherein the amino acid sequence comprises a core sequence of at least 4, 5, 6, 7, 8, or 9 amino acids from SEQ ID NOs: 3, 13, and 71-91, where the at least 4, 5, 6, 7, 8, or 9 amino acids maintain their relative positions as they appear in any one of SEQ ID NOs: 3, 13, and 71-91. In some embodiments, the CKRD peptide or peptidic compound is between 6 to 25 amino acids in length, as described herein elsewhere, and the at least 4, 5, 6, 7, 8, or 9 amino acids maintain their relative positions as they appear in any one of SEQ ID NOs: 3, 13, and 71-91 over the span of 7, 8, 9, or 10 amino acids. For example, a CKRD peptide or peptidic compound may be derived from the amino acid sequence of SEQ ID NO: 3 where the at least 4, 5, 6, or 7 amino acids maintain their relative positions as they appear in SEQ ID NO: 3, where the at least 4, 5, 6, or 7 amino acids maintain their relative positions as they appear in SEQ ID NO: 3 over the span of 7, 8, or 9 amino acids.

In some embodiments, a CKRD peptide or peptidic compound may be described by the formula $X_1$—C—$X_2$, where C is derived from the amino acid sequence of any one of SEQ ID NOs: 3, 13, and 71-91, wherein said amino acid sequence is 6, 7, 8, or 9 amino acids in length, wherein said amino acid sequence comprises at least 4, 5, 6, 7, or 8 amino acids from any one of any one of SEQ ID NOs: 3, 13, and 71-91, and wherein said at least 4, 5, 6, 7, or 8 amino acids maintain their relative positions as they appear in any one of SEQ ID NOs: 3, 13, and 71-91; where $X_1$ and $X_2$ are each 0 to 16 amino acids in length, wherein the total length of the peptide is no more than 25 amino acids. The sum of $X_1$ and $X_2$ may be 0, 1, 2, 3, 4, 5, 6, 7, 8, 9, 10, 11, 12, 13, 14, 15, or 16.

In some embodiments, a CKRD peptide or peptidic compound may be described by the formula $X_1$—C—$X_2$, where C is derived from the amino acid sequence of SEQ ID NO: 3, wherein said amino acid sequence is 7, 8, or 9 amino acids in length, wherein said amino acid sequence comprises at least 4, 5, 6, or 7 amino acids from SEQ ID NO: 3, and wherein said at least 4, 5, 6, or 7 amino acids maintain their relative positions as they appear in SEQ ID NO: 3; where $X_1$ and $X_2$ are each 0 to 18 amino acids in length, wherein the total length of the peptide is no more than 25 amino acids. The sum of $X_1$ and $X_2$ may be 0, 1, 2, 3, 4, 5, 6, 7, 8, 9, 10, 11, 12, 13, 14, 15, 16, 17, or 18.

In some embodiments, a CKRD peptide or peptidic compound may be described by the formula $X_1$—C—$X_2$, where C is derived from the amino acid sequence of SEQ ID NO: 13, wherein said amino acid sequence is 7, 8, or 9 amino acids in length, wherein said amino acid sequence comprises at least 4, 5, 6, or 7 amino acids from SEQ ID NO: 13, and wherein said at least 4, 5, 6, or 7 amino acids maintain their relative positions as they appear in SEQ ID NO: 13; where $X_1$ and $X_2$ are each 0 to 18 amino acids in length, wherein the total length of the peptide is no more than 25 amino acids. The sum of $X_1$ and $X_2$ may be 0, 1, 2, 3, 4, 5, 6, 7, 8, 9, 10, 11, 12, 13, 14, 15, 16, 17, or 18.

Group 5

According to some embodiments, a CKRD peptide or peptidic compound comprises an amino acid sequence of KCQX$_a$X$_b$X$_c$SVY (SEQ ID NO: 153), where X$_a$, X$_b$, and X$_c$ are each any amino acid or none. In some embodiments, X$_a$ may be K, N, E, or none. In some embodiments, X$_b$ may be E, G, D, or none. In some embodiments, X$_c$ may be I, D, E, or none. Preferably, the CKRD peptide or peptidic compound is between 6 to 25 amino acids in length as described herein elsewhere. For example, in some embodiments, a CKRD peptide or peptidic compound may comprise the amino acid sequence of any one of SEQ ID NOs: 15, 20, and 92-112.

According to some embodiments, a CKRD peptide or peptidic compound may be described by the formula $X_1$—C—$X_2$, where C is derived from the amino acid sequence of KCQX$_a$X$_b$X$_c$SVY (SEQ ID NO: 153), where $X_1$ and $X_2$ are each 0 to 16 amino acids in length, wherein the total length of the peptide is no more than 25 amino acids. The maximum value of the sum of $X_1$ and $X_2$ may be 0, 1, 2, 3, 4, 5, 6, 7, 8, 9, 10, 11, 12, 13, 14, 15, or 16.

According to some embodiments, a CKRD peptide or peptidic compound derived from the amino acid sequence of any one of any one of SEQ ID NOs: 15, 20, and 92-112, wherein the amino acid sequence comprises a core sequence of at least 4, 5, 6, 7, 8, or 9 amino acids from any one of SEQ ID NOs: 15, 20, and 92-112, where the at least 4, 5, 6, 7, 8, or 9 amino acids maintain their relative positions as they appear in any one of SEQ ID NOs: 15, 20, and 92-112. In some embodiments, the CKRD peptide or peptidic compound is between 6 to 25 amino acids in length, as described herein elsewhere, and the at least 4, 5, 6, 7, 8, or 9 amino acids maintain their relative positions as they appear in any one of SEQ ID NOs: 15, 20, and 92-112 over the span of 9 or 10 amino acids. For example, a CKRD peptide or peptidic compound may be derived from the amino acid sequence of SEQ ID NO: 15 where the at least 4 or 5 amino acids maintain their relative positions as they appear in SEQ ID NO: 15, where the at least 44 or 5 amino acids maintain their relative positions as they appear in SEQ ID NO: 15 over the span of 5 or 6 amino acids.

In some embodiments, a CKRD peptide or peptidic compound may be described by the formula $X_1$—C—$X_2$, where C is derived from the amino acid sequence of any one of SEQ ID NOs: 15, 20, and 92-112, wherein said amino acid sequence is 4, 5, 6, 7, 8, or 9 amino acids in length, wherein said amino acid sequence comprises at least 4, 5, 6, 7, 8, or 9 amino acids from any one of SEQ ID NOs: 15, 20, and 92-112, and wherein said at least 4, 5, 6, 7, 8, or 9 amino acids maintain their relative positions as they appear in any one of SEQ ID NOs: 15, 20, and 92-112; where $X_1$ and $X_2$ are each 0 to 16 amino acids in length, wherein the total length of the peptide is no more than 25 amino acids. The sum of $X_1$ and $X_2$ may be 0, 1, 2, 3, 4, 5, 6, 7, 8, 9, 10, 11, 12, 13, 14, 15, 16, 17, 18, 19, or 20. In some embodiments, the at least 6 amino acids are W, V, F, G, C, and K.

In some embodiments, a CKRD peptide or peptidic compound may be described by the formula $X_1$—C—$X_2$, where C is derived from the amino acid sequence of SEQ ID NO: 15, wherein said amino acid sequence is 5 amino acids in length, wherein said amino acid sequence comprises at least 4 or 5 amino acids from SEQ ID NO: 15, and wherein said at least 4 or 5 amino acids maintain their relative positions as they appear in SEQ ID NO: 15; where $X_1$ and $X_2$ are each 0 to 20 amino acids in length, wherein the total length of the peptide is no more than 25 amino acids. The sum of $X_1$ and $X_2$ may be 0, 1, 2, 3, 4, 5, 6, 7, 8, 9, 10, 11, 12, 13, 14, 15, 16, 17, 18, 19, or 20.

In some embodiments, a CKRD peptide or peptidic compound may be described by the formula $X_1$—C—$X_2$, where C is derived from the amino acid sequence of SEQ ID NO: 20, wherein said amino acid sequence is 6 amino acids in length, wherein said amino acid sequence comprises at least 4, 5, or 6 amino acids from SEQ ID NO: 20, and wherein said at least 4, 5, or 6 amino acids maintain their relative positions as they appear in SEQ ID NO: 20; where $X_1$ and $X_2$ are each 0 to 19 amino acids in length, wherein the total length of the peptide is no more than 25 amino acids. The sum of $X_1$ and $X_2$ may be 0, 1, 2, 3, 4, 5, 6, 7, 8, 9, 10, 11, 12, 13, 14, 15, 16, 17, 18, or 19.

Group 6

According to some embodiments, a CKRD peptide or peptidic compound comprises an amino acid sequence of DRYLX$_a$X$_b$VHAT (SEQ ID NO: 154), where X$_{a\ and}$ X$_b$ are each any amino acid or none. Preferably, the CKRD peptide or peptidic compound is between 8 to 25 amino acids in length as described herein elsewhere. For example, in some embodiments, a CKRD peptide or peptidic compound may comprise the amino acid sequence of any one of SEQ ID NOs: 19 and 113-115.

According to some embodiments, a CKRD peptide or peptidic compound may be described by the formula $X_1$—C—$X_2$, where C is derived from the amino acid sequence of DRYLX$_a$X$_b$VHAT (SEQ ID NO: 154), where $X_1$ and $X_2$ are each 0 to 17 amino acids in length, wherein the total length of the peptide is no more than 25 amino acids. The maximum value of the sum of $X_1$ and $X_2$ may be 0, 1, 2, 3, 4, 5, 6, 7, 8, 9, 10, 11, 12, 13, 14, 15, 16, or 17.

According to some embodiments, a CKRD peptide or peptidic compound derived from the amino acid sequence of any one of SEQ ID NOs: 19 and 113-115, wherein the amino acid sequence comprises a core sequence of at least 5, 6, 7, 8, 9, or 10 amino acids from any one of SEQ ID NOs: 19 and 113-115, where the at least 5, 6, 7, 8, 9, or 10 amino acids maintain their relative positions as they appear in any one of SEQ ID NOs: 19 and 113-115. In some embodiments, the CKRD peptide or peptidic compound is between 6 to 25 amino acids in length, as described herein elsewhere, and the at least 5, 6, 7, 8, 9, or 10 amino acids maintain their relative positions as they appear in any one of SEQ ID NOs: 19 and 113-115 over the span of 7, 8, 9, or 10 amino acids. For example, a CKRD peptide or peptidic compound may be derived from the amino acid sequence of SEQ ID NO: 19 where the at least 5, 6, 7, 8, or 9 amino acids maintain their relative positions as they appear in SEQ ID NO: 19, where the at least 5, 6, 7, 8, or 9 amino acids maintain their relative positions as they appear in SEQ ID NO: 19 over the span of 8, 9, or 10 amino acids.

In some embodiments, a CKRD peptide or peptidic compound may be described by the formula $X_1$—C—$X_2$, where C is derived from the amino acid sequence of any one of SEQ ID NOs: 19 and 113-115, wherein said amino acid sequence is 8 to 10 amino acids in length, wherein said amino acid sequence comprises at least 5, 6, 7, 8, or 9 amino acids from any one of SEQ ID NOs: 19 and 113-115, and wherein said at least 5, 6, 7, 8, or 9 amino acids maintain their relative positions as they appear in any one of SEQ ID NOs: 15, 20, and 92-112; where $X_1$ and $X_2$ are each 0 to 16 amino acids in length, wherein the total length of the peptide is no more than 25 amino acids. The sum of $X_1$ and $X_2$ may be 0, 1, 2, 3, 4, 5, 6, 7, 8, 9, 10, 11, 12, 13, 14, 15, or 16.

In some embodiments, a CKRD peptide or peptidic compound may be described by the formula $X_1$—C—$X_2$, where C is derived from the amino acid sequence of SEQ ID NO: 19, wherein said amino acid sequence is 9 amino acids in length, wherein said amino acid sequence comprises at least 5, 6, 7, 8, or 9 amino acids from SEQ ID NO: 19, and wherein said at least 5, 6, 7, 8, or 9 amino acids maintain their relative positions as they appear in SEQ ID NO: 19 over the span of 9 or 10 amino acids; where $X_1$ and $X_2$ are each 0 to 16 amino acids in length, wherein the total length of the peptide is no more than 25 amino acids. The sum of $X_1$ and $X_2$ may be 0, 1, 2, 3, 4, 5, 6, 7, 8, 9, 10, 11, 12, 13, 14, 15, or 16.

Peptidic Compounds

According to some embodiments, there is provided peptidic compounds derived from the CKRD peptides of the present invention. Preferably, the peptidic compounds are structurally similar bioactive equivalents of the CKRD peptides of the present embodiments. CKRD peptidic compounds may be a steric enantiomer (D isomer), a rare amino acid of plant origin, an unnatural amino acid or amino acid mimetic, or a chemically modified amino acid. Such chemically modified amino acids are well-known in the art and include amino acids modified by acetylation, acylation, phosporylation, dephosphorylation, glycosylation, myristollation, amidation, aspartic acid/asparagine hydroxylation, phosphopantethane attachment, methylation, methylthiolation, prensyl group attachment, intein N-/C-terminal splicing, ADP-ribosylation, bromination, citrullination, deamination, dihydroxylation, formylation, geranyl-geranilation, glycation, or palmitoylation. According to some embodiments, the candidate CKRD peptidic compounds comprises at least one modifications selected from the groups consisting of: N- and/or C-terminal acetylation; N- and/or C-terminal glycosylation; N- and/or C-terminal biotinylation; a D-amino acid; an un-natural amino acid; and cyclic amino acid substitution.

The CKRD peptidic compounds can comprise D- or L-amino acids. The peptides can comprise all D-amino acids. The peptides can have an acid C-terminus (—$CO_2H$) or an amide C-terminus (—$CONH_2$, —CONHR, or —$CONR_2$).

According to some embodiments, the CKRD peptides and peptidic compounds are non-covalent, low affinity modulators of disease-related CK activity. In preferred embodiments, the peptides and peptidic compounds display peptide binding with disease-related CKs in the micro-milli molar range.

Accordingly, the invention provides for peptides and peptidic compounds that bind disease-related CKs with a dissociation constant less than 10 mM (that is, binds disease-related CKs more tightly than a $K_D$ of 10 mM). Preferably, the dissociation constant is equal to or less than 5 mM, 1 mM, 100 μM, 50 μM, 25 μM, 10 μM, or even 5 μM. In one preferred embodiment, the dissociation constant is less than 10 mM, 5 mM, 1 mM, 100 μM, 50 μM, or 25 μM; and greater than 0.01 μM, 0.1 μM, 1 μM, 5 μM, or 10 μM. In another preferred embodiment, the value of the dissociation constant is contained in one of the following ranges: 5 mM to 1 mM, 1 mM to 100 μM, 100 μM to 50 μM, 50 μM to 25 μM, 25 μM to 10 μM, 10 μM to 5 μM, 5 μM to 1 μM, or 5 μM to 0.1 μM, inclusive.

Accordingly, the invention provides for peptides and peptidic compounds that bind disease-related CKs with a dissociation constant less than 10 μM (that is, binds disease-related CKs more tightly than a $K_D$ of 10 μM). Preferably, the dissociation constant is equal to or less than 5 μM, 1 μM, 100 nM, 50 nM, 25 nM, 10 nM, or even 5 nM. In one preferred embodiment, the dissociation constant is less than 10 μM, 5 μM, 1 μM, 100 nM, 50 nM, or 25 nM; and greater than 0.01 nM, 0.1 nM, 1 nM, 5 nM, or 10 nM. In another preferred embodiment, the value of the dissociation constant is contained in one of the following ranges: 5 μM to 1 μM, 1 μM to 100 nM, 100 nM to 50 nM, 50 nM to 25 nM, 25 nM to 10 nM, 10 nM to 5 nM, 5 nM to 1 nM, or 5 nM to 0.1 nM, inclusive.

According to some embodiments, the CKRD peptides and peptidic compound of the present invention comprise 3 to 9 amino acids and comprise the tripeptide of DYD. The table below provides an exemplary list of CKRD peptides comprising the DYD tripeptide.

| CKRD peptide | SEQ ID NO: |
|---|---|
| NTTEDYDT | SEQ ID NO: 21 |
| DYDYGAPC | SEQ ID NO: 24 |
| DYDYG | SEQ ID NO: 25 |
| DYDY | SEQ ID NO: 26 |
| TTFFDYDYG | SEQ ID NO: 14 |

Screening Methods

According to some embodiments, there is provided a method for identifying CKRD peptides or peptidic compounds comprising: selecting a candidate peptide containing from about 3 to about 25 amino acids derived from a chemokine receptor regulatory domain; and determining the ability of the candidate peptide to modulate the activity of disease-related chemokines. The chemokine receptor regulatory domain may be from conserved regions of the extracellular domain. In some embodiments, the chemokine receptor regulatory domains are from conserved regions of the extracellular domain that are responsive to one or more cognate and unrelated chemokines.

According to some embodiments, there is provided a method for identifying CKRD peptides or peptidic compounds comprising: selecting a candidate peptide containing from about 3 to about 15 amino acids derived from functional domains of GPCRs/CKRs (N-terminus/ECL1, ECL2, ECL3, ECL4); and determining the ability of the candidate peptide to bind to chemokines.

The candidate peptides may contain from about 3 to about 25 amino acids derived from an extracellular region of a chemokine receptor. In some embodiments, the candidate peptide may contain from 3 to 15 amino acids in length (e.g., 3, 4, 5, 6, 7, 8, 9, 10, etc.) derived from an extracellular region of a chemokine receptor, preferably those regions responsive to one or more cognate and unrelated chemokines. This includes, for example, 3 to 12, 3 to 9, 3 to 7, 5 to 12, 5 to 9, 5 to 7, 7 to 13, 7 to 9, 9 to 15, 9 to 13, and 9 to 12 amino acid sequences derived from an extracellular region of a chemokine receptor. Preferred chemokines receptors include, but are not limited to, CXCR1/2, CCR2, CX3CR1, CXCR3, CCR5, CCR7, and CXCR4.

Preferred candidate CKRD peptides have the ability to modulate the activity of one or more (e.g., 2, 3, 4, 5, 6, 7, 8, 9, 10, 11, 12, 15, or more) cognate and unrelated chemokines, and more preferably, disease related chemokines. Disease related CKs include Inflammatory CKs, Constitutive CKs, and Dual Function (Inflammatory and Constitutive) CKs. Inflammatory CKs include, but are not limited to, the following: GRO-α; GRO-β; NAP-2; IL-8-72; IL-8-77; Mig; IP-10; I-TAC; I-309; MCP-1; MCP-2; MCP-4; MIP1-α; MIP1-β; RANTES; Eotaxin; Eotaxin2; Eotaxin3; TARC; MDC-69. Dual CKs include, but are not limited to, the following: SDF1-α; SDF1-β; BCA-1; MIP3-α; MIP3-β; Exodus-2; TECK; C-TAC. Constitutive CKs include, but are not limited to, the following: Fractalkine and Lymphotactin. Other disease related CKs include, but are not limited to, PF-4.

The candidate CKRD peptides may be screened for ability to modulate the activity of one or more (e.g., 2, 3, 4, 5, 6, 7, 8, 9, 10, 12, 15, or more) Inflammatory CKs, Constitutive CKs, Dual Function CKs, and/or other CKs. The candidate CKRD peptides may be screened for ability to modulate the activity of at least one CK from one or more, two or more, three or more, or each group of CKs selected from the group consisting of Inflammatory CKs, Constitutive CKs, Dual Function CKs, and/or other CKs According to some embodiments, one or more amino acids in the candidate CKRD peptidic compounds may be a steric enantiomer (D isomer), a rare amino acid of plant origin, an unnatural amino acid or amino acid mimetic, or a chemically modified amino acid. Such chemically modified amino acids are well-known in the art and include amino acids modified by acetylation, acylation, phosporylation, dephosphorylation, glycosylation, myristollation, amidation, aspartic acid/asparagine hydroxylation, phosphopantethane attachment, methylation, methylthiolation, prensyl group attachment, intein N-/C-terminal splicing, ADP-ribosylation, bromination, citrullination, deamination, dihydroxylation, formylation, geranyl-geranilation, glycation, or palmitoylation. According to some embodiments, the candidate CKRD peptidic compounds comprises at least one modifications selected from the groups consisting of: N- and/or C-terminal acetylation; N- and/or C-terminal glycosylation; N- and/or C-terminal biotinylation; a D-amino acid; an un-natural amino acid; and cyclic amino acid substitution.

While not wishing to be bound by a particular theory, it may be inferred from the CK-binding activity of the peptide in vitro that the peptide interacts with endogenous disease-associated CKs in the diseased animal to modify their biological activity for therapeutic effect. It is also understood that the peptide is capable of interacting with endogenous disease-unrelated CKs to alter their activity for therapeutic effect.

Methods of Treating

According to some embodiments, methods are provided for treating an immune system disorder comprising administrating to a subject in need thereof a therapeutically effective amount of a CKRD peptide or peptidic compound of the present invention. The immune disorder may be selected from an autoimmune disease, multiple sclerosis, transplant rejection psoriasis, and asthma According to some embodiments, methods are provided for ameliorating arthritis in a subject comprising administrating to a subject in need thereof a therapeutically effective amount of a CKRD peptide or peptidic compound of the present invention. According to some embodiments, methods are provided for treating arthritis in a subject comprising administrating to a subject in need thereof therapeutically effective amount of a CKRD peptide or peptidic compound of the present invention. The arthritis may be rheumatoid arthritis or related condition resulting from inflammation or autoimmunity. The subject may be a mammal. The subject may be a human.

According to some embodiments, there is provided pharmaceutical compositions comprising one or more CKRD peptide or peptidic compounds of the present invention and a pharmaceutically acceptable excipient. The pharmaceutical composition may be in any form suitable for administration. In a preferred embodiment, the pharmaceutical composition is in a form suitable for injection. The pharmaceutical compositions of the invention may be used to alter and modulate immune system functioning to treat autoimmune diseases specifically and inflammatory disorders in general. In some embodiments, there is provided methods of treating rheumatoid arthritis comprising administering to a subject in need thereof and therapeutically effective amount of one or more CKRD peptide or peptidic compounds of the present invention and a pharmaceutically acceptable excipient.

The pharmaceutical compositions according to the present invention may be administered as a single dose or in multiple doses. The pharmaceutical compositions of the present invention may be administered either as individual therapeutic agents or in combination with other therapeutic agents. In some embodiments, the pharmaceutical compositions of the present invention may be administered either as individual therapeutic agents or in combination with other therapeutic agents known to treat autoimmune diseases or inflammatory disorders, particularly rheumatoid arthritis. The pharmaceutical compositions of the present invention may be administered in combination with an anti-inflammatory steroid, a non-steroidal anti-inflammatory agent, an immune modulator, or an immune suppressor. In some embodiments, the subject receives at the same time, or sequentially an anti-inflammatory steroid, a non-steroidal anti-inflammatory agent, an immune modulator, or an immune suppressor. The pharmaceutical compositions of the present invention may be administered in combination with corticosteroids, glucocorticoids, NSAIDs, and TNF inhibitors (e.g., adalimumab, etanercept, infliximab).

Examples of corticosteroids and glucocorticoids include, but are not limited to, cortisol, cortisone, clobetasol, hydrocortisone, fludrocortisone, fludroxycortide, flumetasone, flunisolide, fluocinolone, fluocinonide, fluocortolone, fluorometholone, prednisone, prednisolone, 6-alpha-methylprednisolone, triamcinolone, alclometasone, beclometasone, betamethasone, budesonide, dexamethasone, dexamethasone sodium phosphate, amcinonide, cortivazol, desonide, desoximethasone diflucortolone, difluprednate, fluclorolone and dichlorisone, fluperinidene, fluticasone, halcinonide, meprednisone, methylprednisolone, paramethasone, prednazoline, prednylidene, tixocortol, triamcinolone, and acid derivatives thereof, e.g., acetate, propionate, dipropionate, valerate, phosphate, isonicotinate, metasulfobenzoate, tebutate, and hemisuccinate.

Examples of NSAIDs include, but are not limited to, aceclofenac, acemetacin, acetaminophen, acetaminosalol, acetyl-salicylic acid, acetyl-salicylic-2-amino-4-picolineacid, 5-aminoacetylsalicylic acid, alclofenac, amino-profen, amfenac, anileridine, azathioprine, bendazac, benoxaprofen, bermoprofen, α-bisabolol, bromfenac, 5-bromosalicylic acid acetate, bromosaligenin, bucloxic acid, butibufen, carprofen, CC 1088, CC 5013, CDC 801, celecoxib, chromoglycate, cinmetacin, cipamfylline, clindanac, clopirac, COX-189, cyclosporine, sodium diclofenac, diflunisal, ditazol, enfenamic acid, etodolac, etofenamate, etoricoxib, felbinac, fenbufen, fenclozic acid, fendosal, fenoprofen, fentiazac, fepradinol, FK-506, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, JTE-522, ketoprofen, ketorolac, L-745337, leflunomide, lornoxicam, loxoprofen, meclofenamic acid, mefenamic acid, meloxicam, mesalamine, mesalazine, methotrexate, metiazinic acid, mofezolac, montelukast, mycophenolic acid, naproxen, niflumic acid, olsalazine, oxaceprol, oxaprozin, oxyphenbutazone, parsalmide, perisoxal, phenyl-acetyl-salicylate, phenylbutazone, phenylsalicylate, teophyline, pyrazolac, piroxicam, pirprofen, pranoprofen, protizinic acid, rapamycine, rofecoxib, salacetamide, salicylamide-O-acetyl acid, salicylsulphuric acid, salicin, salicylamide, salsalate, sulindac, sulfasalazine, suprofen, suxibutazone, tenoxicam, thalidomide, tetrafluorthalidomide, tiaprofenic acid, tiaramide, tinoridine, tolfenamic acid, tolmetin, tomoxiprol, tropesin, valdecoxib (Searle), xenbucin, ximoprofen, zaltoprofen, zomepirac, zafirlukast.

Definitions

A "peptide" refers to a polymer in which the monomers are amino acids linked together through amide bonds. "Peptides" are generally smaller than proteins, i.e., about two to about fifty amino acids in length. The term "peptide" includes "dipeptides" comprised of two amino acids and "tripeptides" comprised of three consecutively linked amino acids, and so forth. The peptides in the present embodiments are 2 to 50 amino acids in length. Preferably, peptides in the present embodiments are 2 to 25 amino acids in length, 2 to 25 amino acids in length, 2 to 20 amino acids in length, 2 to 15 amino acids in length, 2 to 10 amino acids in length, 2 to 9 amino acids in length, 2 to 8 amino acids in length, 2 to 7 amino acids in length, 2 to 6 amino acids in length, 2 to 5 amino acids in length. This includes peptides that are 3 to 25, 3 to 20, 3 to 15, 3 to 10, 3 to 9, 3 to 8, 3 to 7, 3 to 6, 3 to 5, 4 to 25, 4 to 20, 4 to 15, 4 to 10, 4 to 9, 4 to 8,4 to 7, 4 to 6, 5 to 25, 5 to 20, 5 to 15, 5 to 10, 5 to 9, 5 to 8, 5 to 7, 6 to 25, 6 to 20, 6 to 15, 6 to 12, 6 to 10, 6 to 9, 7 to 25, 7 to 20, 7 to 15, 7 to 12, 7 to 10, 7 to 9, 8 to 25, 8 to 20, 8 to 15, 8 to 12, 8 to 10, 9 to 25, 9 to 20, 9 to 18, 9 to 15, 9 to 14, 9 to 12, 10 to 25, 10 to 20, 10 to 15, 10 to 14, 10 to 12, 12 to 25 or 12 to 20 amino acids in length.

The terms "peptidyl" and "peptidic" as used throughout the specification and claims are intended to include active derivatives, variants, and/or mimetics of the peptides according to the present embodiments. Peptidic compounds are structurally similar bioactive equivalents of the peptides according to the present embodiments. By a "structurally similar bioactive equivalent" is meant a peptidyl compound with structure sufficiently similar to that of an identified bioactive peptide to produce substantially equivalent therapeutic effects. For example, peptidic compounds derived from the amino acid sequence of the peptide, or having an amino acid sequence backbone of the peptide, are considered structurally similar bioactive equivalents of the peptide.

The term "variant" refers to a protein or polypeptide in which one or more amino acid substitutions, deletions, and/or insertions are present as compared to the amino acid sequence of an protein or peptide and includes naturally occurring allelic variants or alternative splice variants of an protein or peptide. The term "variant" includes the replacement of one or more amino acids in a peptide sequence with a similar or homologous amino acid(s) or a dissimilar amino acid(s). Preferred variants include alanine substitutions at one or more of amino acid positions. Other preferred substitutions include conservative substitutions that have little or no effect on the overall net charge, polarity, or hydrophobicity of the protein. Conservative substitutions are set forth in the table below. According to some embodiments, the CK polypeptides have at least 60%, 65%, 70%, 75%, 80%, 85%, 88%, 95%, 96%, 97%, 98% or 99% sequence identity with the amino acid sequences of the preferred embodiments.

Conservative Amino Acid Substitutions

| | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | praline |
| | methionine |
| | leucine |
| | isoleucine |

The table below sets out another scheme of amino acid substitution:

| Original Residue | Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include proteins and peptides with additional amino acid residues before or after the protein or peptide amino acid sequence on linker peptides. The term "variant" also encompasses polypeptides that have the amino acid sequence of the proteins/peptides of the present invention with at least one and up to 25 (e.g., 1, 2, 3, 4, 5, 6, 7, 8, 9, 10, 15, 20) additional amino acids flanking either the 3' or 5' end of the amino acid sequence or both.

The term "variant" also refers to a protein that is at least 60 to 99 percent identical (e.g., 60, 65, 70, 75, 80, 85, 90, 95, 98, 99, or 100%, inclusive) in its amino acid sequence of the proteins of the present invention as determined by standard methods that are commonly used to compare the similarity in position of the amino acids of two polypeptides. The degree of similarity or identity between two proteins can be readily calculated by known methods. Preferred methods to determine identity are designed to give the largest match between the sequences tested. Methods to determine identity and similarity are codified in publicly available computer programs. Variants will typically have one or more (e.g., 2, 3, 4, 5, etc.) amino acid substitutions, deletions, and/or insertions as compared with the comparison protein or peptide, as the case may be.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type proteins. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid sidechains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination.

The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to the embodiments provide a spatial arrangement of reactive chemical moieties that closely resemble the three-dimensional arrangement of active groups in the peptide on which the peptide mimetic is based. As a result of this similar active-site geometry, the peptide mimetic has effects on biological systems that are similar to the biological activity of the peptide.

The peptide mimetics of the embodiments are preferably substantially similar in both three-dimensional shape and biological activity to the peptides described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. A second method is altering cyclic structure for stability, such as N to C interchain imides and lactames. An example of this is given in conformationally restricted thymopentin-like compounds, such as those disclosed in U.S. Pat. No. 4,457,489, the disclosure of which is incorporated by reference herein in its entirety. A third method is to substitute peptide bonds in the peptide by pseudopeptide bonds that confer resistance to proteolysis.

A peptide mimetics may include protective groups at one or both ends of the mimetic, or replacement of one or more peptide bonds with non-peptide bonds, is less susceptible to proteolytic cleavage than the peptide itself. For instance, one or more peptide bonds can be replaced with an alternative type of covalent bond (e.g., a carbon-carbon bond or an acyl bond). Peptide mimetics can also incorporate amino-terminal or carboxyl terminal blocking groups such as t-butyloxycarbonyl, acetyl, alkyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl, thereby rendering the mimetic less susceptible to proteolysis. Non-peptide bonds and carboxyl- or amino-terminal blocking groups can be used singly or in combination to render the mimetic less susceptible to proteolysis than the corresponding peptide. Additionally, substitution of D-amino acids for the normal L-stereoisomer can be effected, e.g. to increase the half-life of the molecule. Accordingly, the peptide mimetics include peptides having one or more of the following modifications: peptides wherein one or more of the peptidyl [—C(O)NR—] linkages (bonds) have been replaced by a non-peptidyl linkage such as a —CH$_2$-carbamate linkage [—CH$_2$—OC(O)NR—]; a phosphonate linkage; a —CH$_2$-sulfonamide [—CH$_2$—S(O)$_2$NR—] linkage; a urea [—NHC(O)NH—] linkage; a —CH$_2$-secondary amine linkage; or an alkylated peptidyl linkage [—C(O)NR$^6$— where R$^6$ is lower alkyl]; peptides wherein the N-terminus is derivatized to a —NRR$^1$ group; to a —NRC(O)R group; to a —NRC(O)OR group; to a —NRS(O)$_2$R group; to a —NHC(O)NHR group, where R and R$^1$ are hydrogen or lower alkyl with the proviso that R and R$^1$ are not both hydrogen; to a succinimide group; to a benzyloxycarbonyl-NH—(CBZ—CH—) group; or to a benzyloxycarbonyl-NE- group having from 1 to 3 substituents on the phenyl ring selected from the group consisting of lower alkyl, lower alkoxy, chloro, and bromo; or peptides wherein the C terminus is derivatized to —C(O)R$^2$ where R$^2$ is selected from the group consisting of lower alkoxy, and —NR$^3$ R$^4$ where R$^3$ and R$^4$ are independently selected from the group consisting of hydrogen and lower alkyl.

Preferred mimetics have from zero to all of the —C(O)NH— linkages of the peptide replaced by a linkage selected from the group consisting of a —CR$_2$OC(O)NR— linkage; a phosphonate linkage; a —CH$_2$S(O)$_2$NR— linkage; a —CH$_2$NR— linkage; and a —C(O)NR$^6$— linkage, and a —NHC(O)NH— linkage where R is hydrogen or lower alkyl and R$^6$ is lower alkyl, and wherein the N-terminus of the mimetic is selected from the group consisting of a —NRR$^1$ group; a —NRC(O)R group; a —NRC(O)OR group; a —NRS(O)$_2$R group; a —NHC(O)NHR group; a succinimide group; a benzyloxycarbonyl-NH— group; and a benzyloxycarbonyl-NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl, and still further wherein the C-terminus of the mimetic has the formula —C(O)R$^2$ where R$^2$ is selected from the group consisting of hydroxy, lower alkoxy, and —NR$^3$ R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide, and physiologically acceptable salts thereof.

The term "fragment" or "subsequence" refers to a protein or polypeptide that consists of a continuous subsequence of the amino acid sequence of a protein or peptide and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine. The term "fragment" includes fragments, whether identical or different, from the same protein or peptide, with a contiguous amino acid sequence in common or not, joined together, either directly or through a linker. Such fragments may comprise at least 3 contiguous amino acids that are identical to the amino acid sequence of the present invention.

The phrase "pharmaceutically acceptable" or "therapeutically acceptable" refers to molecular entities and compositions that are physiologically tolerable and preferably do not typically produce an allergic or similar untoward reaction, such as gastric upset, dizziness and the like, when administered to a human. Preferably, as used herein, the term "pharmaceutically acceptable" means approved by a regulatory agency of the Federal or a State government or listed in the U.S. Pharmacopeia or other generally recognized pharmacopeia (e.g., Remington's Pharmaceutical Sciences) for use in animals, and more particularly in humans.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Examples

Example 1

Micro-Array Analysis of Phage Presented Chemokine Binding Peptides—Summary of Materials and Methods Alignment analysis (ClustalW2 alignment) was performed to identify regulatory amino acids, expressed as consensus sequences and potential CK binding peptides, in the CK receptors. Whereas alignment algorithms are routinely used to determine global homology, the present analysis is restricted to discrete CK-binding domains common to related, or shared by unrelated CK receptors. The present inventors determined that consensus sequences identified by alignment analysis in the CK-binding domains of the CK receptors would function as non-covalent, low affinity modulators of disease-related CK activity. Amino acid sequences, not evinced by ClustalW2 alignment analysis as consensus sequences, cryptic regulatory sequences, were also candidate non-covalent, low affinity modulaltors of disease-related CK activity.

Peptide sequences were screened for the ability to bind an array of CKs, which included an array of Inflammatory CKs, Constitutive CKs, Dual Function (Inflammatory and Constitutive) CKs, and other CKs. An example of a protocol used for the micro-array analysis of phage presented chemokine binding peptides in provided in Example 2. For example, peptide 15 (P15), WVFGSGLCK (SEQ ID NO: 16), is found in ECL-1 of human C—X—C chemokine receptor type 3 (CXCR3; Interferon-inducible protein 10 receptor). P15 was found to bind specifically and differentially to the Rheumatoid Arthritis-associated CKs, IP-10, RANTES, MCP1, IL-8 and Fractalkine in micro-array analysis. P15 was found to have an anti-inflammatory effect in a study of Adjuvant-Induced-Arthritis (AIA), evidence that the CK-binding peptide was modulating disease-related CKs for therapeutic effect (Examples 27 and 29). P15, at a greater than therapeutic dose, had no apparent effect, physical or behavioral, on healthy, non-disease-induced animals (Example 30). CK-binding peptides were tested in the animal model of Rheumatoid Arthritis for therapeutic activity.

Disease-related CKs used in the micro-array analysis were obtained from PreproTech Inc. (Rocky Hill, NJ USA). A list of the particular CKs are provided below.

Inflammatory CKs: (1) GRO-α (CXCL1 cat.no.300-11), (2) GRO-β (CXCL2 cat.no.300-39), (3) NAP-2 (CXCL7 cat.no.300-14), (4) IL-8(72aa) (CXCL8 cat.no.200-08N), (5) IL-8(77aa) (CXCL8 cat.no.200-08), (6) Mig (CXCL9 cat.no.300-26), (7) IP-10 (CXCL10 cat.no.300-12), (8) I-TAC (CXCL11 cat.no.300-46), (9) I-309 (CCL1 cat.no. 300-37), (10) MCP-1 (CCL2 cat.no.300-04), (11) MCP-2 (CCL8 cat.no. 300-15), (11) MCP-4 (CCL13 cat.no.300-24), (12) MIP-la (CCL3 cat.no.300-08), (13) MIP-la (CCL4 cat.no.300-09), (14) RANTES (CCL5 cat.no.300-06), (15) Eotaxin (CCL11 cat.no.300-21), (16) Eotaxin 2 (CCL24 cat.no.300-33), (17) Eotaxin 3(CCL26 cat.no.300-48).

Constitutive CKs: (1) TARC (CCL17 cat.no.300-30), (2) MDC(69aa), (CCL22 cat.no.300-36A), (3) SDF-1α (CXCL12 cat.no.300-28a), (4) SDF-1β (CXCL12 cat.no.300-28b), (5) BCA-1 (CXCL13, cat.no.300-47), (6) MIP-3α (CCL20 cat.no.300-29A), (7) MIP-3β (CCL19 cat.no.300-29B), (8) Exodus-2 (CCL21 cat.no.300-35), (9) TECK (CCL25 cat.no.300-45), (10) CTAC (CCL27 cat.no.300-54).

Dual Function (Inflammatory and Constitutive) CKs: (1) Fractalkine (CX3CL1 cat.no.300-31), (2) Lymphotactin (XCL-1 cat.no.300-20), (3) PF-4 (CXCL4 cat.no.300-16).

The following CK receptor-derived peptides were screened for relevant activities:

SEQ ID NO. 1: SYYDDVGL, referred to herein as "Peptide F. Origin: N-terminus (ECL1) of human C—C chemokine receptor type 3 (CCR3; Eosinophil Eotaxin receptor). The biotinylated peptide (N-terminus) was synthesized by BiomerTechnology, USA and dissolved in DMSO (0.05% in $H_2O$).

SEQ ID NO. 2: WVFGHGMCK, referred to herein as "Peptide 2". Origin: Extra Cellular Loop (ECL)-2 of human C—C chemokine receptor type 3 (CCR3; Eosinophil Eotaxin receptor). The biotinylated peptide (N-terminus) was synthesized by Sigma, Israel and dissolved in $H_2O$.

SEQ ID NO. 3: LFGNDCE, referred to herein as "Peptide 5". Origin: ECL-4 of human C—C chemokine receptor type 3 (CCR3; Eosinophil Eotaxin receptor). The biotinylated peptide (N-terminus) was synthesized by Sigma, Israel and dissolved in $H_2O$.

SEQ ID NO. 4: WVFGTFLCK, referred to herein as "Peptide 7". Origin: Consensus sequence (maximum of 3 variable amino acids) founding ECL-2 of all human chemokine receptors. The biotinylated peptide (N-terminus) was synthesized by BiomerTechnology, USA and dissolved in DMSO (0.1% in $H_2O$).

SEQ ID NO. 5: WVFGNAMCK, referred to herein as "Phage Presented (Ph) Peptide (p) 8". Origin: ECL-2 of human C—C chemokine receptor type 2 (CCR2; Monocyte Chemoatrractant Protein 1 receptor). The recombinant peptide was cloned in and expressed by the M13 cloning vector. The peptide was synthesized by BiomerTechnology, USA and dissolved in DMSO (0.05% in $H_2O$).

SEQ ID NO. 6: GNAMCK, referred to herein as "Ph-p 8.1". Origin: ECL-2 of human C—C chemokine receptor type 2 (CCR2; Monocyte Chemoatrractant Protein 1 receptor). The recombinant peptide was cloned in and expressed by the M13 cloning vector.

SEQ ID NO. 7: WVFG, referred to herein as "Ph-p 8.4". Origin: ECL-2 of human C—C chemokine receptor type 2 (CCR2; Monocyte Chemoatrractant Protein 1 receptor). The recombinant peptide was cloned in and expressed by the M13 cloning vector.

SEQ ID NO. 8: WVFGAAACK, referred to herein as "Ph-p 8.6". Origin: ECL-2 of human C—C chemokine receptor type 2 (CCR2; Monocyte Chemoatrractant Protein 1 receptor). The recombinant peptide was cloned in and expressed by the M13 cloning vector.

SEQ ID NO. 9: WVFGNAACK, referred to herein as "Ph-p 8.7". Origin: ECL-2 of human C—C chemokine receptor type 2 (CCR2; Monocyte Chemoatrractant Protein 1 receptor). The recombinant peptide was cloned in and expressed by the M13 cloning vector.

SEQ ID NO. 10: WVFGVHFCK, referred to herein as "Ph-p 8.77". ECL-2 of human C—C chemokine receptor type 7 (CCR7; EBV-inducible G-protein coupled receptor. 1). The peptide was synthesized by BiomerTechnology, USA and dissolved in DMSO (0.05% in $H_2O$).

SEQ ID NO. 11: WVFGAAMCK, referred to herein as "Ph-p 8.8". Origin: ECL-2 of human C—C chemokine receptor type 2 (CCR2; Monocyte Chemoatrractant Protein 1 receptor). The recombinant peptide was cloned in and expressed by the M13 cloning vector.

SEQ ID NO. 12: NAMCK, referred to herein as "Ph-p 8.11". Origin: ECL-2 of human C—C chemokine receptor type 2 (CCR2; Monocyte Chemoatrractant Protein 1 receptor). The recombinant peptide was cloned in and expressed by the M13 cloning vector.

SEQ ID NO. 13: FFGLNNC, referred to herein as "Peptide 10". Origin: ECL-4 of human C—C chemokine receptor type 5 (CCRS; HIV-1 Fusion Co-receptor). The biotinylated peptide (N-terminus) was synthesized by BiomerTechnology, USA and dissolved in DMSO (0.1% in $H_2O$).

SEQ ID NO. 14: TTFFDYDYG, referred to herein as "Ph-p 11". Origin: N-terminus (ECL-1) of human C—C chemokine receptor type 2 (CCR2; Monocyte Chemoatrractant Protein 1 receptor). The recombinant peptide was cloned in and expressed by the M13 cloning vector.

SEQ ID NO. 15: EDSVY, referred to herein as "Ph-p 13". Origin: ECL-3 of human C—C chemokine receptor type 2 (CCR2; Monocyte Chemoatrractant Protein 1 receptor). The recombinant peptide was cloned in and expressed by the M13 cloning vector.

SEQ ID NO. 16: WVFGSGLCK, referred to herein as "Ph-p 15". Origin: ECL-2 of human C—X—C chemokine receptor type 3 (CXCR3; Interferon-inducible protein 10 receptor). The recombinant peptide was cloned in and expressed by the M13 cloning vector. The peptide was synthesized by BiomerTechnology, USA and dissolved in DMSO (0.05% in $H_2O$).

SEQ ID NO. 17: HHTCSLHFP, referred to herein as "Ph-p 16". Origin: ECL-3 of human C—C chemokine receptor type 1 (CCR1; Macrophage inflammatory protein 1-alpha receptor). The recombinant peptide was cloned in and expressed by the M13 cloning vector.

SEQ ID NO. 18: HYTCSSHFP, referred to herein as "Ph-p 17". Origin: ECL-3 of human C—C chemokine receptor type 5 (CCRS; HIV-1 Fusion Co-receptor). The recombinant peptide was cloned in and expressed by the M13 cloning vector.

SEQ ID NO. 19: DRYLNIVHAT, referred to herein as "Ph-p 18". Origin: ECL-3 of human C—X—C chemokine receptor type 3 (CXCR; Interferon-inducible protein 10 receptor). The recombinant peptide was cloned in and expressed by the M13 cloning vector.

SEQ ID NO. 20: TKCOKE, referred to herein as "Ph-p 20". Origin: ECL-3 of human C—C chemokine receptor type 2 (CCR2; Monocyte Chemoatrractant Protein 1 receptor). The recombinant peptide was cloned in and expressed by the M13 cloning vector.

Tri-peptide DYD, referred to herein as "Ph-p 33". N-terminus consensus sequence of all human C—C type chemokine receptors (CCR1-10). The recombinant peptide was cloned in and expressed by the M13 cloning vector.

SEQ ID NO. 27: WVFGNMICK, referred to herein as "Ph-p 8 Rat". ECL-2 of rat C—C chemokine receptor type 2 (CCR2; Monocyte Chemoatrractant Protein 1 receptor). The recombinant peptide was cloned in and expressed by the M13 cloning vector. The peptide was synthesized by BiomerTechnology, USA and dissolved in DMSO (0.05% in $H_2O$).

TABLE 1-1

Table 1-1 CXCR2 (and other)-CKR Derived Peptides

| CBP* | SEQ ID NO: | CKR | Related Peptide** | CKR | SEQ ID NO: |
|---|---|---|---|---|---|
| WVFGNAMCK | 3 | CCR2 | WVFGSGLCK | CXCR3 | 16 |
| GNAMCK | 4 | CCR2 | HNAMCK | CX3CR1 | 155 |
| WVFG | 5 | CCR2 | WYFG | CXCR4 | 156 |
| WVFGAAACK | 6 | CCR2 | WSLGSATCR | CCR10 | 157 |
| WVFGNAACK | 7 | CCR2 | WVFSNATCK | CCR6 | 158 |
| WVFGAAMCK | 8 | CCR2 | WKFQTFMCK | CCR9 | 159 |
| TTFFDYDYG | 11 | CCR2 | TTFFYYDLQ | XCR1 | 162 |
| WVFGSGLCK | 13 | CXCR3 | WIEGTFLCK | CXCR2 | 161 |
| HHTCSLHFP | 14 | CCR1 | HYTCSSHFP | CCR5 | 18 |
| WVFGHGMCK | 19 | CCR3 | WVFGQVMCK | CXCR6 | 160 |

*CBP Chemokine Binding Peptide (micro-array data)
**Related Peptide Shared consensus sequence with coffesponding CBP. Potential CBP. No micro-array data for related peptide.

SEQ ID NO. 21: NTTEDYDT, referred to herein as "Ph-p 21". N-terminus (ECL-1) of human C—C chemokine receptor type 1 (CCR1; Macrophage inflammatory protein 1-alpha receptor). The recombinant peptide was cloned in and expressed by the M13 cloning vector.

SEQ ID NO. 22: WVFGHGMCK, referred to herein as "Ph-p 25". ECL-2 of human C—C chemokine receptor type 3 (CCR3; Eosinophil Eotaxin receptor). The recombinant peptide was cloned in and expressed by the M13 cloning vector.

SEQ ID NO. 23: SYYDDVGL, referred to herein as "Ph-p 27". N-terminus (ECL-1) of human C—C chemokine receptor type 3 (CCR3; Eosinophil Eotaxin receptor). The recombinant peptide was cloned in and expressed by the M13 cloning vector.

SEQ ID NO. 24: DYDYGAPC, referred to herein as "Ph-p 30". N-terminus (ECL-1) consensus sequence (maximum of 3 amino acid variables) of all human C—C and C—X—C type chemokine receptors. The recombinant peptide was cloned in and expressed by the M13 cloning vector.

SEQ ID NO. 25: DYDYG, referred to herein as "Ph-p 31". N-terminus consensus sequence of all human C—C type chemokine receptors (CCR1-10). The recombinant peptide was cloned in and expressed by the M13 cloning vector.

SEQ ID NO. 26: DYDY, referred to herein as "Ph-p 32". N-terminus consensus sequence of all human C—C type chemokine receptors (CCR1-10). The recombinant peptide was cloned in and expressed by the M13 cloning vector.

Example 2

Micro-Array Analysis of Phage Presented Chemokine Binding Peptides

The following is a description of the protocol used for the micro-array analysis of phage presented chemokine binding peptides.

(1) Printing: Chemokine (CK) solution (in water) was serially diluted with Print Reagent (GenTel BioSurfaces USA) to final concentrations of 50 μg and 25 μg/ml. BSA/BSA-Biotin control solutions (in water) were diluted with Print Reagent to 100 μg/ml. Amplified stock of M13 phage control (M13KEgIII Cloning Vector, New England Biolabs, Cat.No.E8101S) was stored in Tris Buffered Saline (TBS; pH7.5, 4° C.) and diluted with Print Reagent to the working titre (108 pfu/μl). An automated spotting robot (16 pin print tool, 0.4 mm head; BioRobotics, UK) was used to print the CK/BSA control/M13 control, 5 repeats per sample (CK 25 μg/ml and 50 μg/ml; BSA 100 μg/ml; M13 20 μl), on PATH Protein Microarray Slides (GenTel, Prod.No. 2-1005/-1025) at 200-300 C, and 50-70% relative humidity. Printed microarray slides were stored at Room Temperature (RT) or 4° C. for at least 24 h before use.

(2) Blocking: Block Buffer (500 μl/partition; PATHblock, GenTel, Prod.No. 2-1014) was applied to the slide for 1 hour at room temp (RT). After removal of Block Buffer, the slide was air dried for 25 minutes;

(3) Phage Presented Peptide Binding: Amplified recombinant phage stock was stored in TBS and diluted with Wash Buffer to working titer (10⁷ pfu/µl). Recombinant phage suspension (300 µl) was applied per partition and incubated at RT for 1 hour with gentle agitation.

(4) First Washing: The slides were washed twice with Wash Buffer 300 µl/partition).

(5) Primary Antibody (Ab) Labeling: The slides were incubated with the Primary Ab (1 mg/ml diluted ×2500 (Wash Reagent), 300 µl; Mouse Anti-M13 monoclonal Ab; Amersham Biosciences, UK; Product Code 27-9420-01) for 45 minutes at RT.

(6) Second Washing: The slides were washed twice with Wash Buffer (300 µl/partition).

(7) Secondary Ab Labeling: The slides were incubated with Secondary Ab (1.5 mg/ml diluted ×5000 (Wash Reagent), 300 µl; Cy3-conjugated AffiniPure Goat Anti-Mouse IgG; Jackson ImmunoReserch Labs, USA; Product Code 115-165-062).

(8) Third Washing: The slides were washed twice with Wash Buffer (300 µl/partition).

(9) Rinse: the slides were rinsed twice with Rinse Buffer (PATHrinse, GenTel, Prod.No. 2-1018) then dried well.

(10) Scanning: The peptide-bound, labeled slide was scanned (Laser Intensity 80%, Gain 80%, Resolution 10 µm) with a ScanArray Life Scanner (Packard BioChip Technologies, USA).

(11) Analysis: Quantitative analysis of micro-array was performed by the SpotReader program of Niles Scientific (USA) and presented as Relative Fluorescence (RF) as a function of CK concentration. Micro-array readout (Cy3 fluorescence) was quantified to determine the relative binding affinities of a CBP for the CKs and by inference, the specificity of the CBP for binding to a CK.

Surface Plasmon Resonance (SPR): SPR was performed to make a quantitative determination of CK-peptide affinity. SPR measures the apparent equilibrium dissociation constant ($K_D$) of the CK-binding peptide in the CK-peptide complex. $K_D$ is the ratio of the rate constants, $K_d$ (1/s) and $K_a$ (1/Ms), $K_d/K_a$. SPR was done with the ProteOn XPR36-Protein Interaction Array System (BioRad, Israel) with the Sensor Chip, GLM (sensor range 12-15 K response units).

Figure 25B:
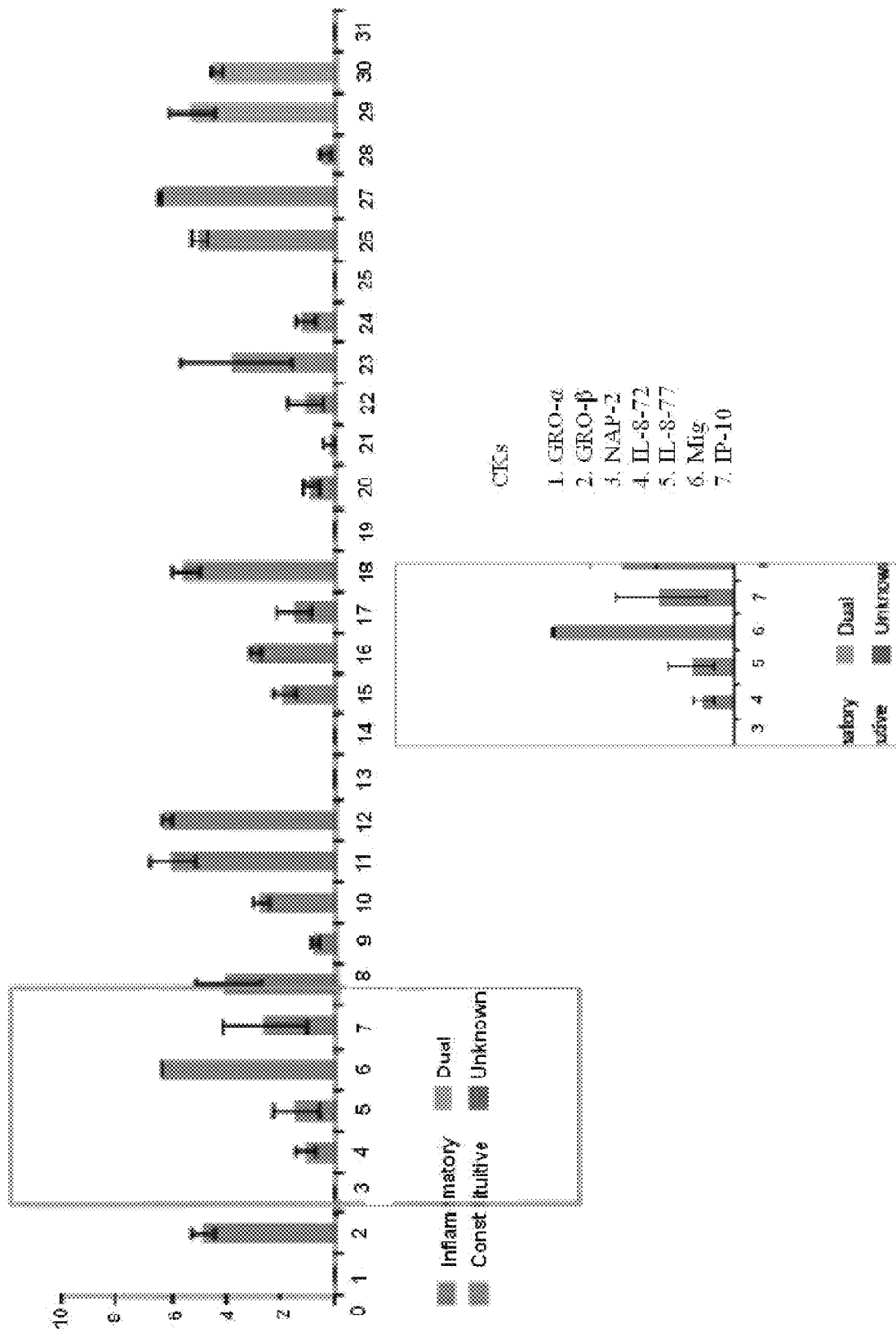

Summary of Results: Affinity of Chemokine—Peptide Inteaction. FIG. 1 shows the chemokine (CK) key to chemokine usage for FIGS. 2-24. The micro-array data proved that CK receptor-derived peptides bound specifically and differentially by non-covalently interaction to CKs. The affinity with which peptides interact with CKs is relevant for low affinity reagents that are intended to engage multiple disease-related target proteins. SPR analysis was employed to determine the apparent equilibrium dissociation constants (KD) of CK-peptide complexes. CBP6 (VTTFFDYD-YGAPC, from the N-terminal of CCR2; SEQ ID NO: 28) was found to have $K_D$ values of $1.06^{e-3}$ and $2.82^{e-5}$ for the CKs, IL-8 and Mig, respectively (FIG. 25a). Peptide binding in the micro-milli molar range is low affinity interaction. SPR analysis also corroborated differential binding measurements made by the micro-array analysis (FIG. 25b).

Example 3

Micro-Array Analysis of Chemokine Binding Peptide 5 (CBP5) Binding to Inflammatory, Constitutively Expressed and Dual Function CKs FIG. 2 shows the binding affinity of CBP5 to several chemokines. CBP5 bound with relatively high affinity (>2,500 Relative Fluorescence Units (RFU), responses in the upper 75% range of 0-10,000 RFUs) to the inflammatory CKs Eotaxin, Eotaxin 3, MCP-4 and RANTES, cognate CK ligands of receptor CCR3 from which CBP5 is derived. The same peptide bound with relatively high affinity to IL-8, Mig, I-309 and MCP-1 unrelated CK ligands of CCR3. CBP5 also bound the constitutively expressed CKs, SDF1-α/β, MIP3-α, Exodus-2 and TECK and the dual function CK, Fractalkine, none of which is a cognate ligand of CCR3.

Example 4

Micro-Array Analysis of Phage-Presented Peptide 8 (Ph-p28) Binding to Inflammatory, Constitutively Expressed and Dual Function CKs FIG. 3 shows that Ph-p28 bound with relatively high affinity (>25,000 RFU, responses in the upper 75% range of 0-100,000 RFU) to the inflammatory CKs MCP-2 and -4, cognate CK ligands of CCR2 from which CBP8 was derived. The same phage-displayed peptide bound with relatively high affinity to the inflammatory CKs IL-8, I-TAC, I-309 and Eotaxin 3 and to the constitutively expressed CKs, SDF1-β, BCA-1 and TECK, and the dual function CK, Fractalkine, all of which are unrelated CK ligands of the CCR2.

Example 5

Micro-Array Analysis of Phage-Presented Peptide 8.1 (Ph-p8.1) Binding to Inflammatory, Constitutively Expressed and Dual Function CKs FIG. 4 shows that Ph-p8.1 bound with relatively high affinity (>15,000 RFU, responses in the upper 75% range of 0-60,000 RFU) to the inflammatory CK Eotaxin 3, the constitutively expressed CKs BCA-1 and TECK and the dual function CK, Lymphotactin, none of which is a related ligand of CCR2 from which the peptide is derived.

Example 6

Micro-Array Analysis of Phage-Presented Peptide 8.4 (Ph-p8.4) Binding to Inflammatory, Constitutively Expressed and Dual Function CKs FIG. 5 shows that Ph-p8.4 bound with relatively high affinity (>15,000 RFU, responses in the upper 75% range of 0-60,000 RFU) to the inflammatory CKs MCP-2 and MCP-4, cognitive ligands of CCR2 from which the peptide is derived. The same phage-displayed peptide bound with relatively high affinity to the inflammatory CKs IL-8, Mig, IP-10, I-TAC, I-309, Eotaxin and Eotaxin 3, that are non-related ligands of CCR2. PH-p8.4 also bound the constitutively expressed CKs SDF-1, BCA-1 and TECK and the dual function CKs Fractalkine and Lymphotactin.

Example 7

Micro-Array Analysis of Phage-Presented Peptide 8.6 (Ph-p8.6) Binding to Inflammatory, Constitutively Expressed and Dual Function CKs FIG. 6 shows that Ph-p8.6 bound with relatively high affinity (>15,000 RFU, responses in the upper 75% range of 0-60,000RFU) to the inflammatory CKs MCP-1,2 and 4, cognate ligands of CCR2 from which the peptide is derived. The same phage-displayed peptide bound to the inflammatory CKs Mig, IP-10, I-TAC, I-309, Eotaxin, Eotaxin 2 and 3. Ph-p8.6 also bound the constitutively expressed CKs SDF1α and β, BCA-1, Exodus 2 and TECK and the dual function CK Lymphotactin.

Example 8

Micro-Array Analysis of Phage-Presented Peptide 8.7 (Ph p8.7) Binding to Inflammatory, Constitutively Expressed and Dual Function CKs FIG. 7 shows that Ph-p8.7 bound with relatively high affinity (>15,000 RFU, responses in the upper 75% range of 0-60,000RFU) to the inflammatory CKs MCP-2 and 4, cognate ligands of CCR2 from which the peptide is derived. The same phage-displayed peptide bound to the inflammatory CKsMIG, Mig, IP-10, I-TAC, I-309, Eotaxin and Eotaxin 3. Ph-p8.7 also bound the constitutively expressed CKs SDF1β, BCA-1 and TECK and the dual function CK Lymphotactin.

Example 9

Micro-Array Analysis of Phage-Presented Peptide 8.8 (Ph-p8.8) Binding to Inflammatory, Constitutively Expressed and Dual Function CKs FIG. 8 shows that Ph-p8.8 bound with relatively high affinity (>15,000 RFU, responses in the upper 75% range of 0-60,000RFU) to the inflammatory CKs MCP-1,2 and 4, cognate ligands of CCR2 from which the peptide is derived. The same phage-displayed peptide bound to the inflammatory CKs IL-8, Mig, IP-10, I-TAC, I-309, Eotaxin, Eotaxin 2/3 and MDC 69. Ph-p8.8 also bound the constitutively expressed CKs SDF1α and β, BCA-1, Mip 3α, Exodus 2, TECK and C-TAC and the dual function CKs Fractalkine and Lymphotactin.

Example 10

Micro-Array Analysis of Phage-Presented Peptide 8.11 (Ph-p8.11) Binding to Inflammatory, Constitutively expressed and Dual Function CKs FIG. 9 shows that Ph-p8.11 bound with relatively high affinity (>10,000 RFU, responses in the upper 75% range of 0-40,000RFU) to the inflammatory CKs IP-10, I-TAC and Eotaxin 3. Ph-p8.11 also bound the constitutively expressed CKs SDF1α and β, BCA-1, Exodus 2 and TECK and C-TAC.

Example 11

Micro-Array Analysis of Chemokine Binding Peptide 10 (CBP10) Binding to Inflammatory, Constitutively Expressed and Dual Functions CKs FIG. 10 shows that CBP10 bound with relatively high affinity (>600 RFU, responses in the upper 75% range of 0-2400 RFU) to the inflammatory CK, MCP1, cognate ligand of CCR2 from which CBP10 is derived. The same peptide bound with relatively high affinity to the inflammatory CKs, GRO-β, I-TAC, I-309, Eotaxin, Eotaxin 2/3 and to the constitutively expressed CKs, SDF1-α,/β BCA-1 and TECK, and the dual function CKs, Fractalkine and Lymphotactin, all of which are unrelated ligands of the CCR2.

Example 12

Micro-Array Analysis of Phage-Presented Peptide 11 (Ph-p11) Binding to Inflammatory, Constitutively Expressed and Dual Functions CKs FIG. 11 shows that Ph-p11 bound with relatively high affinity (>600 RFU, responses in the upper 75% range of 0-2400 RFU) to the inflammatory CKs MCP-1, -2 and -4, cognate ligand of CCR2 from which Ph-p11 was derived. The same peptide bound with relatively high affinity to the inflammatory CKs, GRO-β, Mig, RANTES, Eotaxin, Eotaxin 3 and to the constitutively expressed CK TECK, and the dual function CK Lymphotactin, all of which are unrelated ligands of the CCR2.

Example 13

Micro-Array Analysis of Phage-Presented Peptide 15 (Ph-p15) Binding to Inflammatory, Constitutively Expressed and Dual Function CKs FIG. 12 shows that Ph-p15 bound with relatively high affinity (>15,000 RFU, responses in the upper 75% range of 0-60,000RFU) to the inflammatory CKs Mig, IP-10 and I-TACK, cognate ligands of CXCR3 from which the peptide is derived. The same phage-displayed peptide bound to the inflammatory CKs GRO-β, IL-8, MCP-1, -2, -4, RANTES, Eotaxin, Eotaxin 2 and Eotaxin 3. Ph-p15 also bound the constitutively expressed CKs BCA-1, Exodus 2 and TECK and the dual function CKs Fractalkine and Lymphotactin.

Example 14

Micro-Array Analysis of Phage-Presented Peptide 16 (Ph-p16) Binding to Inflammatory, Constitutively Expressed and Dual Function CKs FIG. 13 shows that Ph-p16 bound with relatively high affinity (>15,000 RFU, responses in the upper 75% range of 0-60,000RFU) to the inflammatory CKs MCP-4 and RANTES, cognate ligands of CCR'1 from which the peptide is derived. The same phage-displayed peptide bound to the inflammatory CKs GRO-β, IL-8, Mig, I-TAC, I-309, MCP-1/2, Eotaxin, Eotaxin 2/3 and MDC 69. Ph-p16 also bound the constitutively expressed CKs BCA-1, TECK and the dual function CKs Fractalkine and Lymphotactin.

Example 15

Micro-Array Analysis of Phage-Presented Peptide 17 (Ph-p17) Binding to Inflammatory, Constitutively Expressed and Dual Function CKs FIG. 14 shows that Ph-p17 bound with relatively high affinity (>600 RFU, responses in the upper 75% range of 0-2,400 RFU) to the inflammatory CKs RANTES and MCP-2, cognate ligands of CCR 5 from which the peptide is derived. The same phage-displayed peptide bound to the inflammatory CKs GRO-β, IL-8, Mig, I-TAC, MCP-1/4, Eotaxin and Eotaxin 3. Ph-p17 also bound the constitutively expressed CK TECK and the dual function CK Lymphotactin.

Example 16

Micro-Array Analysis of Phage-Presented Peptide 18 (Ph-p18) Binding to Inflammatory, Constitutively expressed and Dual Function CKs

FIG. 15 shows that Ph-p18 bound with relatively high affinity (>9,000 RFU, responses in the upper 75% range of 0-36,000 RFU) to the inflammatory CKs Mig and I-TAC, cognate ligands of CXCR3 from which the peptide is derived. The same phage-displayed peptide bound to the inflammatory CKs GRO-β, IL-8, MCP-1/2/4, RANTES, Eotaxin, Eotaxin 2 and 3. Ph-p18 also bound the constitutively expressed CKs BCA-1 and TECK and the dual function CK Lymphotactin.

Example 17

Micro-Array Analysis of Phage-Presented Peptide 20 (Ph-p20) Binding to Inflammatory, Constitutively Expressed and Dual Function CKs

FIG. 16 shows that Ph-p20 bound with relatively high affinity (>15,000 RFU, responses in the upper 75% range of 0-60,000 RFU) to the inflammatory CKs MCP-1, -2 and -4, cognate ligands of CCR2 from which the peptide is derived. The same phage-displayed peptide bound to the inflammatory CKs GRO-β, IL-8, Mig, IP-10, RANTES, Eotaxin and Eotaxin 3. Ph-p20 also bound the constitutively expressed CKs BCA-1, Exodus 2 and TECK and the dual function CKs Fractalkine and Lymphotactin.

Example 18

Micro-Array Analysis of Phage-Presented Peptide 25 (Ph-p25) Binding to Inflammatory, Constitutively Expressed and Dual Function CKs

FIG. 17 shows that Ph-p25 bound with relatively high affinity (>15,000 RFU, responses in the upper 75% range of 0-60,000 RFU) to the inflammatory CKs GRO-β, IL-8, Mig, IP-10, MCP-1, -2 and -4, cognate ligands of CCR2 from which the peptide is derived. The same phage-displayed peptide bound to the inflammatory CKs RANTES, Eotaxin and Eotaxin 3. Ph-p25 also bound the constitutively expressed CKs BCA-1, Exodus 2 and TECK and the dual function CKs Fractalkine and Lymphotactin.

Example 19

Micro-Array Analysis of Phage-Presented Peptide 27 (Ph-p27) Binding to Inflammatory, Constitutively Expressed and Dual Function CKs

FIG. 18 shows that Ph-p27 bound with relatively high affinity (>15,000 RFU, responses in the upper 75% range of 0-60,000 RFU) to the inflammatory CKs Mig and I-TAC, cognate ligands of CXCR3 from which the peptide is derived. The same phage-displayed peptide bound to the inflammatory CKs GRO-β, IL-8, MCP-1, -2, -4, RANTES, Eotaxin, Eotaxin 2 and Eotaxin 3. Ph-p27 also bound the constitutively expressed CKs BCA-1, Exodus 2 and TECK and the dual function CKs Fractalkine and Lymphotactin.

Example 20

Micro-Array Analysis of Phage-Presented Peptide 30 (Ph-p30) Binding to Inflammatory, Constitutively Expressed and Dual Function CKs

FIG. 19 shows that Ph-p30 bound with relatively high affinity (>15,000 RFU, responses in the upper 75% range of 0-60,000 RFU) to the inflammatory CKs IL-8, Mig, I-TAC, I-309, MCP-1, -2, -4, RANTES, Eotaxin, Eotaxin 2 and Eotaxin 3. Ph-p30 also bound the constitutively expressed CKs MDC-69, SDFα/β, BCA-1, Exodus 2, TECK and C-TAC and the dual function CKs Fractalkine and Lymphotactin.

Example 21

Micro-Array Analysis of Phage-Presented Peptide 31 (Ph-p31) Binding to Inflammatory, Constitutively Expressed and Dual Function CKs

FIG. 20 shows that Ph-p31 bound with relatively high affinity (>15,000 RFU, responses in the upper 75% range of 0-60,000 RFU) to the inflammatory CKs IL-8, Mig, I-TAC, I-309, MCP-1, -2, -4, RANTES, Eotaxin, Eotaxin 2 and Eotaxin 3. Ph-p31 also bound the constitutively expressed CKs SDF1α/β, BCA-1, Exodus 2 and TECK and the dual function CKs Fractalkine and Lymphotactin.

Example 22

Micro-Array Analysis of Phage-Presented Peptide 32 (Ph-p32) Binding to Inflammatory, Constitutively expressed and Dual Function CKs

FIG. 21 shows that Ph-p32 bound with relatively high affinity (>10,000 RFU, responses in the upper 75% range of 0-40,000 RFU) to the inflammatory CKs GRO-βIL-8, Mig, I-TAC, I-309, MCP-2, -4, RANTES, Eotaxin, Eotaxin 2 and Eotaxin 3. Ph-p32 also bound the constitutively expressed CKs SDF1α/β, BCA-1, Exodus 2 and TECK and the dual function CKs Fractalkine and Lymphotactin.

Example 23

Micro-Array Analysis of Phage-Presented Peptide 33 (Ph-p33) Binding to Inflammatory, Constitutively expressed and Dual Function CKs

FIG. 22 shows that Ph-p33 bound with relatively high affinity (>15,000 RFU, responses in the upper 75% range of 0-60,000 RFU) to the inflammatory CKs IL-8, Mig, IP-10, MCP-2, -4, RANTES and Eotaxin 3. Ph-p33 also bound the constitutively expressed CKs SDF1β, BCA-1, Exodus 2 and TECK and the dual function CKs Fractalkine and Lymphotactin.

Example 24

Micro-Array Analysis of Phage-Presented Peptide 8.77 (Ph-p8.77) Binding to Inflammatory, Constitutively Expressed and Dual Function CKs

FIG. 23 shows that Ph-p8.77 bound with relatively high affinity (>15,000 RFU, responses in the upper 75% range of 0-60,000 RFU) to the inflammatory CKs, IL-8, Mig, I-TAC, I-309, MCP-2, -4 and Eotaxin 3. Ph-p8.77 also bound the constitutively expressed CKs, SDF1β,1 BCA-1 and TECK and the dual function CK, Fractalkine.

Example 25

Micro-Array Analysis of M13 Phage Binding to Inflammatory, Constitutively Expressed and Dual Function CKs FIG. 24 shows the result of screening M13 phage against CKs in micro-array. M13 phage served as negative control in the screen of phage-presented peptides against CKs in micro-array.

Example 26

The Animal Model of Disease-Adjuvant Induced Arthritis

Laboratory research and clinical observation indicated that the expression of specific chemo-attractant cytokines, Chemokines (CKs) and their cognate receptors correlated with specific autoimmune diseases. CKs and CK receptors are critical mediators of immune responses. Anomalous expression of these immunological proteins was interpreted as evidence for a pathological role in inflammatory and autoimmune diseases. The use of CK receptor antagonists and studies of receptor knock-out mice validated CK receptors as drug targets. The CK receptors, CXCR1/2, CCR2, CX3CR1, CXCR3, CCRS and CXCR4 and their respective cognate ligands are expressed at elevated levels in Rheumatoid Arthritis. These specific receptors and their CK ligands, therefore, are prime drug targets for treatment of the disease.

Rheumatoid Arthritis is chronic inflammation characterized by T lymphocyte and macrophage infiltration into the synovial membrane and pannus formation. The pannus is rich in activated macrophages secreting proteases and other inflammatory mediators that destroy the underlying cartilage and bone. In comparison with normal synovial fluid, which is essentially acellular, arthritic synovial fluid is abundant in neutrophils, macrophages, T lymphocytes and dendritic cells.

Adjuvant-Induced Arthritis (AIA) is a well established disease model and use of this model has gone a long way in aiding the understanding of the pathology in clinical Rheumatoid Arthritis. The model closely mimics the pathology of the human disease, including histopathological changes, cell infiltration, hypersensitivity and swelling of the affected joint.

Peptides were tested in a rat model of AIA for their anti-inflammatory effects.

Disease Induction: AIA was induced in female Lewis rats aged 7-8 weeks by injection of heat-killed *Mycobacerioum tuberculosis* (Mt strain H37Ra, Difco Laboratories, USA) dispersed in incomplete Freund's adjuvant to a final concentration of 10 mg/ml (100 µl) at the base of the tail on day 0.

Measurement: Clinical Score (CS, 0-4) for each limb based on (a) joint inflammation, (b) redness, (c) deformity.

Efficacy Protocol 1 (5 rats per group). Peptide/control compound was injected intra-peritoneally (IP, 200 µl) on days 7-11 and 14-18.

Rats were sacrificed (CO2 inhalation) on day 43.

Efficacy Protocol 2 (8 rats per group). Group 1: peptide/ PBS was injected intra-peritoneally (IP, 200 µl) on days 7-18; Group 2: PBS was injected IP on days 7-18; Group 3: Dexamethasone (Dexa) was injected IP on days 11 (Clinical Score (CS)1) and 13. Rats were sacrificed on day 43.

Combination Efficacy Protocol 1 (8 rats per group). Group 1: peptide injected IP on days 7-18; Group 2: PBS injected IP on days 7-18; Group 3: Dexa injected IP on day 11 (CS 1) and day 13; Group 4: Dexa injected IP on days 11 and 13 then peptide injected on days 14-22; Group 5: Dexa injected IP on days 11 and 13 then PBS injected on days 14-22.

Combination Efficacy Protocol 2 (8 rats per group). Group 1: peptide injected IP on days 7-18; Group 2: PBS injected IP on days 7-18; Group 3: Dexa injected IP on day 11 (CS 1) and day 13 then PBS on days 14-22; Group 4: PBS injected IP on days 7-10,12,14; Dexa injected on days 11, 13. Peptide injected on days 15-19.

Combination Efficacy Protocol 3 (8 rats per group). Group 1: peptide injected IP on days 7-18; Group 2: PBS injected IP on days 7-18; Group 3: Dexa injected IP on day 11 (CS 1) and day 13 then PBS on days 14-22; Group 4: peptide injected IP on days 7-10,12,14; Dexa injected on days 11, 13. Peptide injected on days 15-19.

Control Reagents for Adjuvant Induced Arthritis: Anti-Inflammatory Control: Dexamethasone Sodium Phosphate (Dexacort Forte, Teva) was dissolved in Phosphate Buffer Saline (PBS, GIBCO) to a final concentration of 1 mg/ml and injected in 200 µl (200 µg).

Negative Control: Phosphate Buffer Saline (PBS).

Example 27

Efficacy of Peptide 5 (P5) in the Animal Model of Disease, Adjuvant Induced Arthritis (AIA)

The inflammatory CK, RANTES, the constitutively expressed CK, SDF1 and the dual function CK, Fractalkine and their cognate receptors are expressed at elevated levels in Rheumatoid Arthritis (RA) These immunological regulatory proteins are thought to have a pathological role in this autoimmune disease. P5, screened against a range of inflammatory, constitutive and dual function CKs bound specifically and differentially to RANTES, SDF1 and Fractalkine (FIG. 2).

Figure 26:
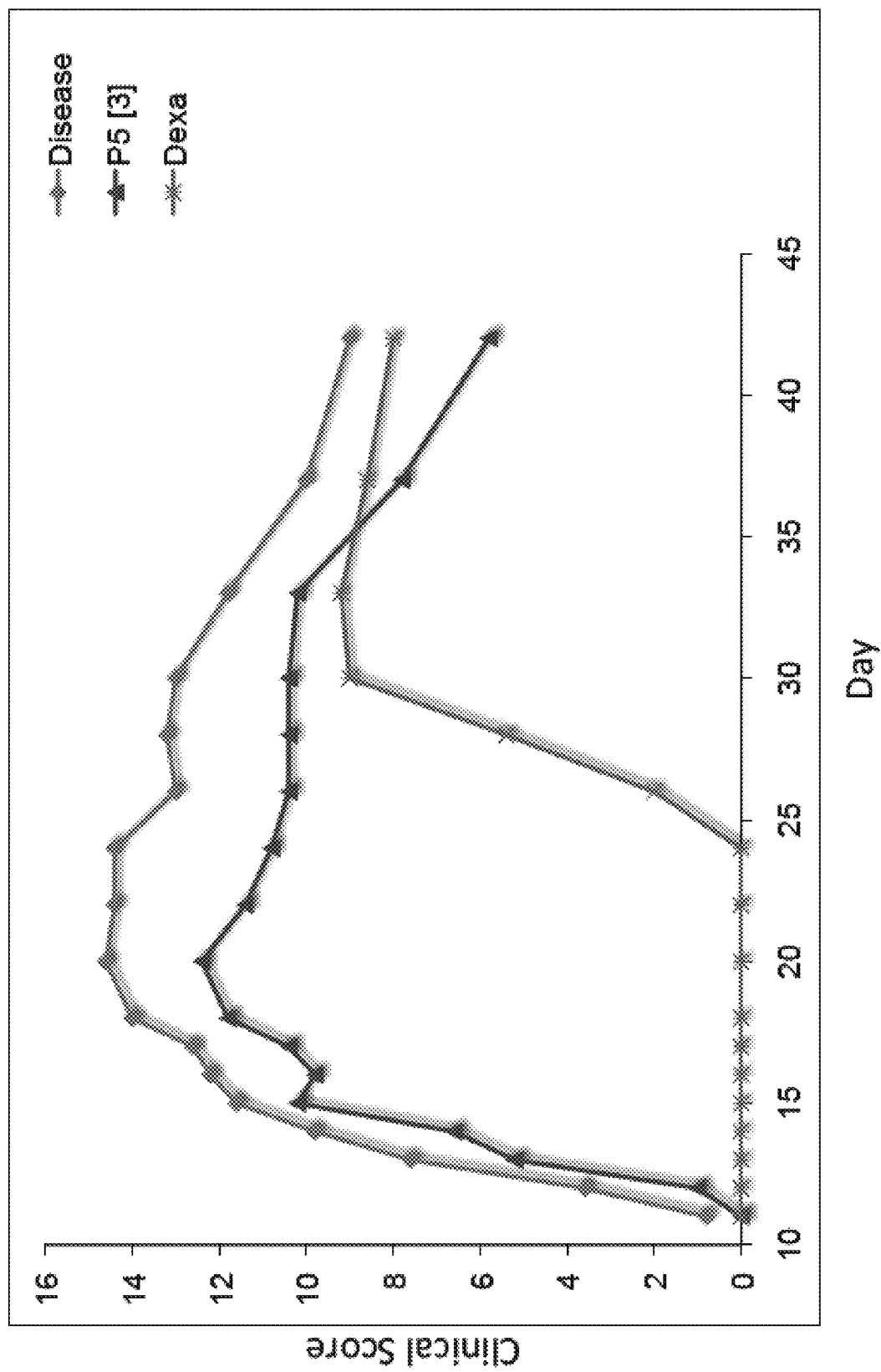
FIG. 26 shows the effect of peptide 5 administered to Adjuvant Induced Arthritic (AIA)rats.

P5 that is derived from the CK receptor CCR3 and bound to RA-related CKs, was tested for anti-inflammatory activity in a rat model of AIA (FIG. 26). The peptide was injected intraperitoneally (IP, 3.6 µg/injection) on days 7-11 and 14-18 following disease induction on day 0. The peptide had an anti-inflammatory effect from about day13 that was maintained for the duration of the experiment. At the end of the experiment inflammation in the P5-treated group was about 60% of the disease, untreated group. Inflammation in the untreated, disease group was self-resolving from a maximal clinical score (CS) of 14 on day 19. Inflammation in the dexamethasone (Dexa)-treated group was at the base line until day 24, 6 days after the last injection, when it increased until it was almost equal that of the untreated, disease group.

Example 28

Efficacy of Peptide 15 (P15) in the Animal Model of Disease, Adjuvant Induced Arthritis (AIA)

The inflammatory CKs, RANTES, IL-8, MCP-1, IP-10 and the dual function CK, Fractalkine and their cognate receptors are expressed at elevated levels in Rheumatoid Arthritis (RA). These immunological regulatory proteins are thought to have a pathological role in this autoimmune disease. P15, screened against a range of inflammatory, constitutive and dual function CKs bound specifically and differentially to RANTES, IL-8, MCP-1, IP-10 and Fractalkine (FIG. 2).

Figure 27:
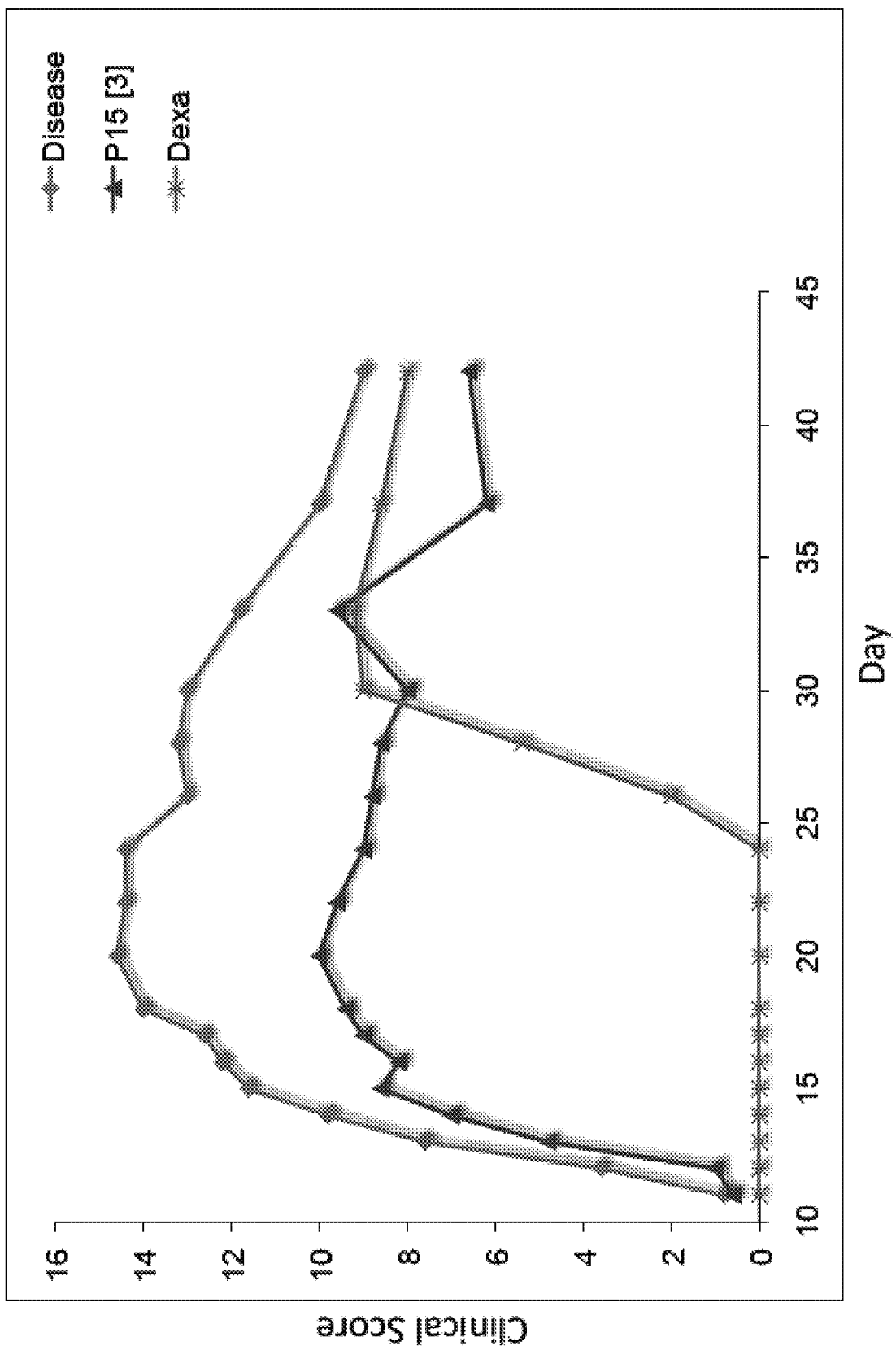
FIG. 27 shows the effect of peptide 15 administered to AIA rats.

P15 that is derived from the CK receptor CXCR3 and bound to RA-related CKs, was tested for anti-inflammatory activity in a rat model of AIA (FIG. 27). The peptide was injected IP (3.2 µg/injection) on days 7-11 and 14-18 following disease induction on day 0. The peptide had an anti-inflammatory effect from about day13 that was maximal (40%) on day 20. At the end of the experiment inflammation in the P5 treated group was about 70% of the disease, untreated group. Inflammation in the untreated, disease group was self-resolving from a maximal clinical score (CS) of 14 on day 19 Inflammation in the Dexa-treated group was at the base line until day 24, 6 days after the last injection, when it increased until it was almost equal that of the untreated, disease group.

Example 29

Efficacy of Peptide 8 (P8) in the Animal Model of Disease, Adjuvant Induced Arthritis (AIA)

The inflammatory CKs, RANTES, IL-8, the constitutively expressed CK, SDF 1 and the dual function CK, Fractalkine and their cognate receptors are expressed at elevated levels in Rheumatoid Arthritis (RA). These immunological regulatory proteins are thought to have a pathological role in this autoimmune disease. P8, screened against a range of inflammatory, constitutive and dual function CKs bound specifically and differentially to RANTES, IL-8, SDF 1and Fractalkine (FIG. 3).

Figure 28:
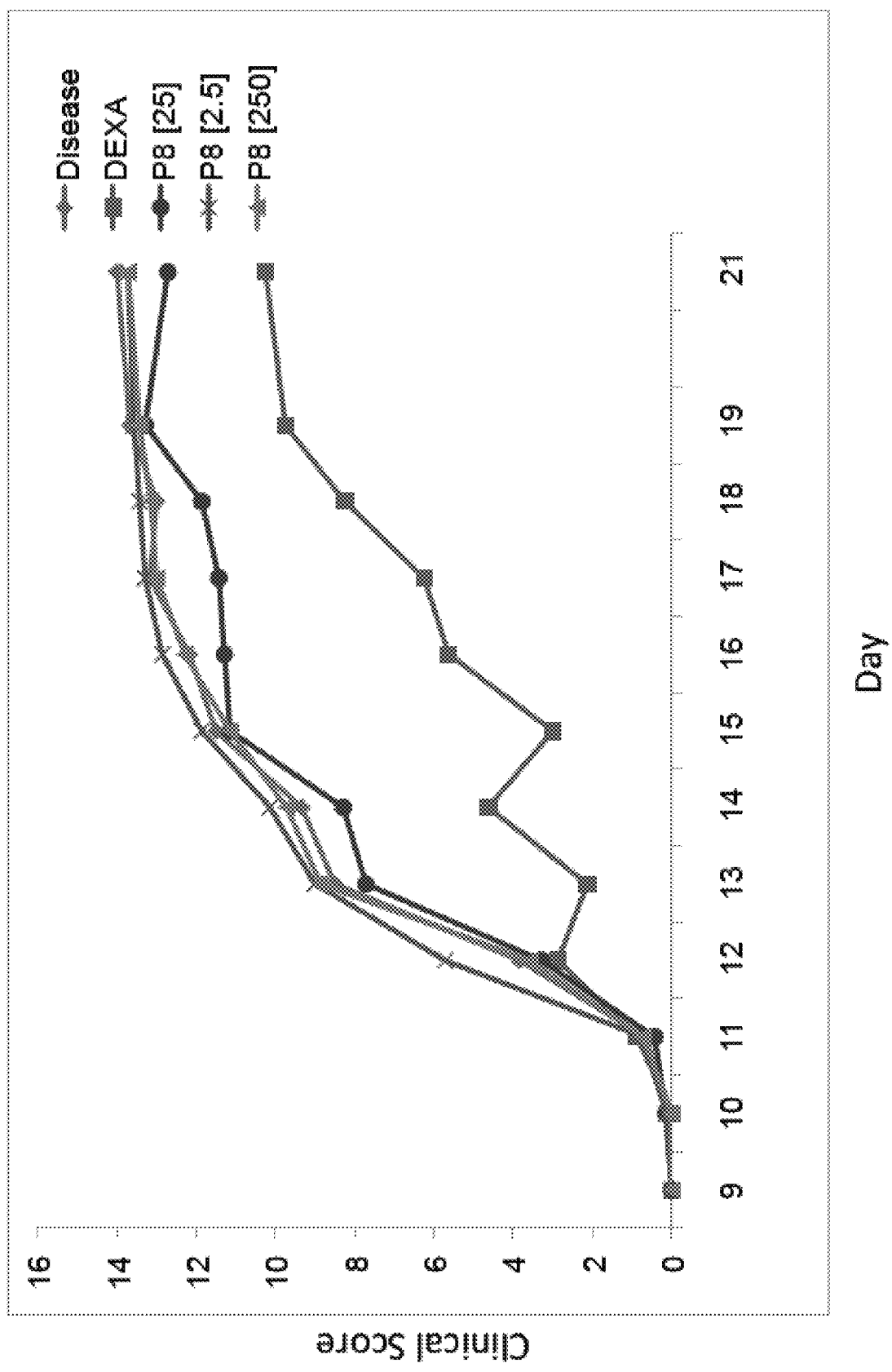
FIG. 28 shows the effect of multiple doses of peptide 8 administered to AIA rats.

P8 that is derived from the CK receptor CCR2 and bound to RA-related CKs, was tested for anti-inflammatory activity in a rat model of AIA (FIG. 28). The peptide was injected IP at three different doses, 2.5 µg, 25 µg and 250 µg on days 7-18 following disease induction on day 0. P8 had an anti-inflammatory effect from about day12 that was maximal (17%) about day 17 (25 µg). Inflammation in the Dexa-treated increased from day 15, 2 days after the second injection, approaching inflammation in the disease, untreated group by day 21. Of the three doses, the 25 µg dose proved to be the most efficacious.

Example 30

Efficacy of Peptide 15 (P15) at Three Different Doses in the Animal Model of Disease, Adjuvant Induced Arthritis (AIA)

The inflammatory CKs, RANTES, IL-8, MCP-1, IP-10 and the dual function CK, Fractalkine and their cognate receptors are expressed at elevated levels in Rheumatoid Arthritis (RA). These immunological regulatory proteins are thought to have a pathological role in this autoimmune disease. P15, screened against a range of inflammatory, constitutive and dual function CKs bound specifically and differentially to RANTES, IL-8, MCP-1, IP-10 and Fractalkine (FIG. 2).

Figure 29:
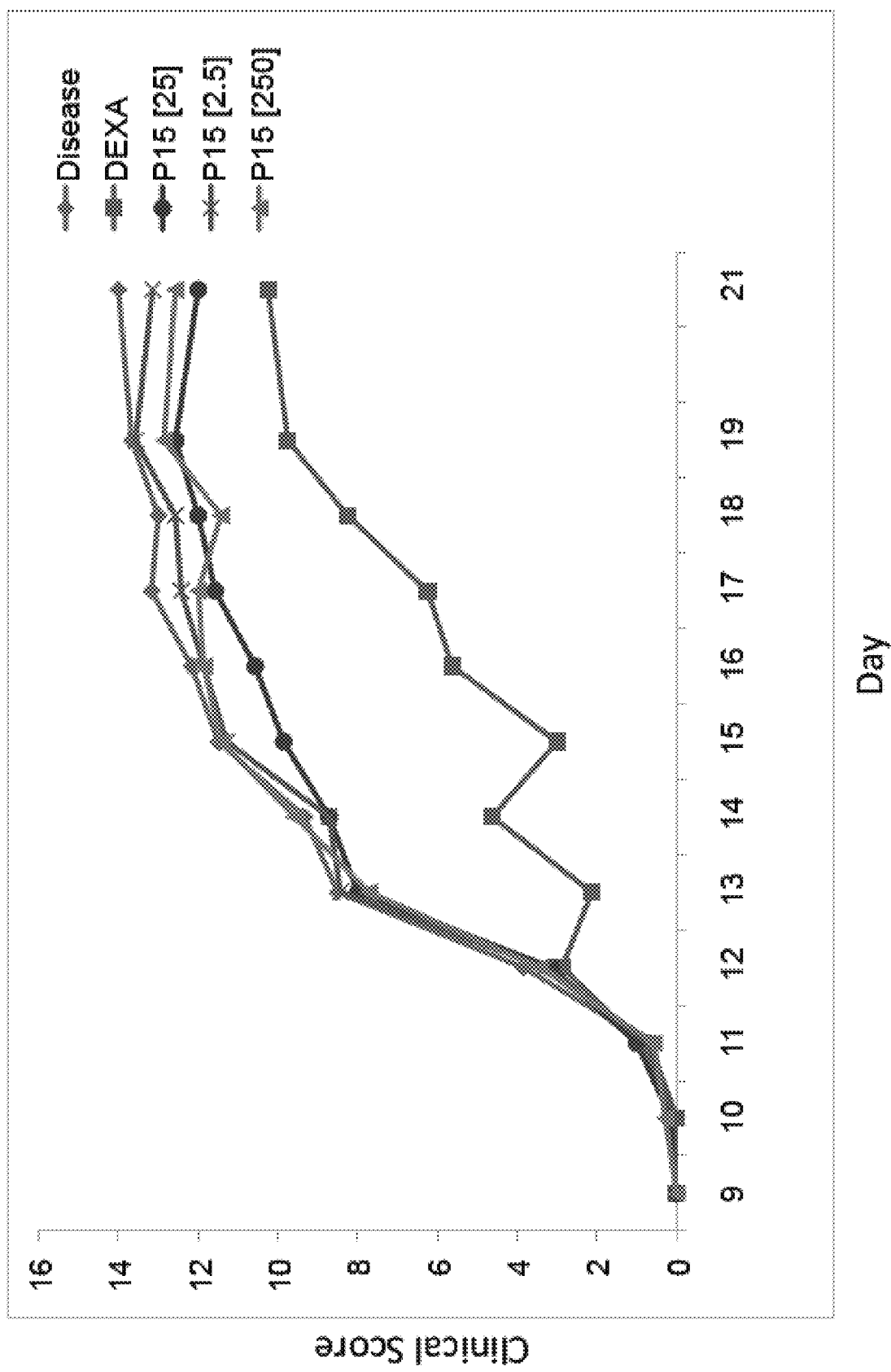
FIG. 29 shows the effect of multiple doses of peptide 15 administered to AIA rats.

P15 was tested for anti-inflammatory activity in a rat model of AIA (FIG. 29). The peptide was injected IP at three different doses, 2.5 µg, 25 µg and 250 µg on days 7-18 following disease induction on day 0. P15 had an anti-inflammatory effect from about day 13 that was maximal (14%) on day 21 (25 µg). Inflammation in the Dexa-treated increased from day 15, 2 days after the second injection, approaching inflammation in the disease, untreated group by day 21. Of the three doses, the 25 µg dose proved to be the most efficacious.

Example 31

Effect of Peptide 15 (P15) on Healthy, Non-Disease-Induced Rats

P15, screened against a range of inflammatory, constitutive and dual function CKs bound specifically and differentially to the RA-related CKs, RANTES, IL-8, MCP-1, IP-10 and Fractalkine (FIG. 12). P15 was injected IP (30 ug/injection) on 12 consecutive days to determine if this anti-inflammatory peptide had any effect at a therapeutic dose on healthy, non-disease-induced rats. The peptide had no obvious physiological or behavioral effect on healthy rats.

Example 32

Efficacy of Peptide 8.8 (P 8.8) at Three Different Doses in the Animal Model of disease, Adjuvant Induced Arthritis (AIA)

The inflammatory CKs, IL-8, MCP-1, IP-10, the constitutively expressed CK, SDF 1 and the dual function CK, Fractalkine and their cognate receptors are expressed at elevated levels in Rheumatoid Arthritis (RA). These immunological regulatory proteins are thought to have a pathological role in this autoimmune disease. P8.8, screened against a range of inflammatory, constitutive and dual function CKs bound specifically and differentially to IL-8, MCP-1, IP-10, SDF 1 and Fractalkine (FIG. 8).

Figure 30:
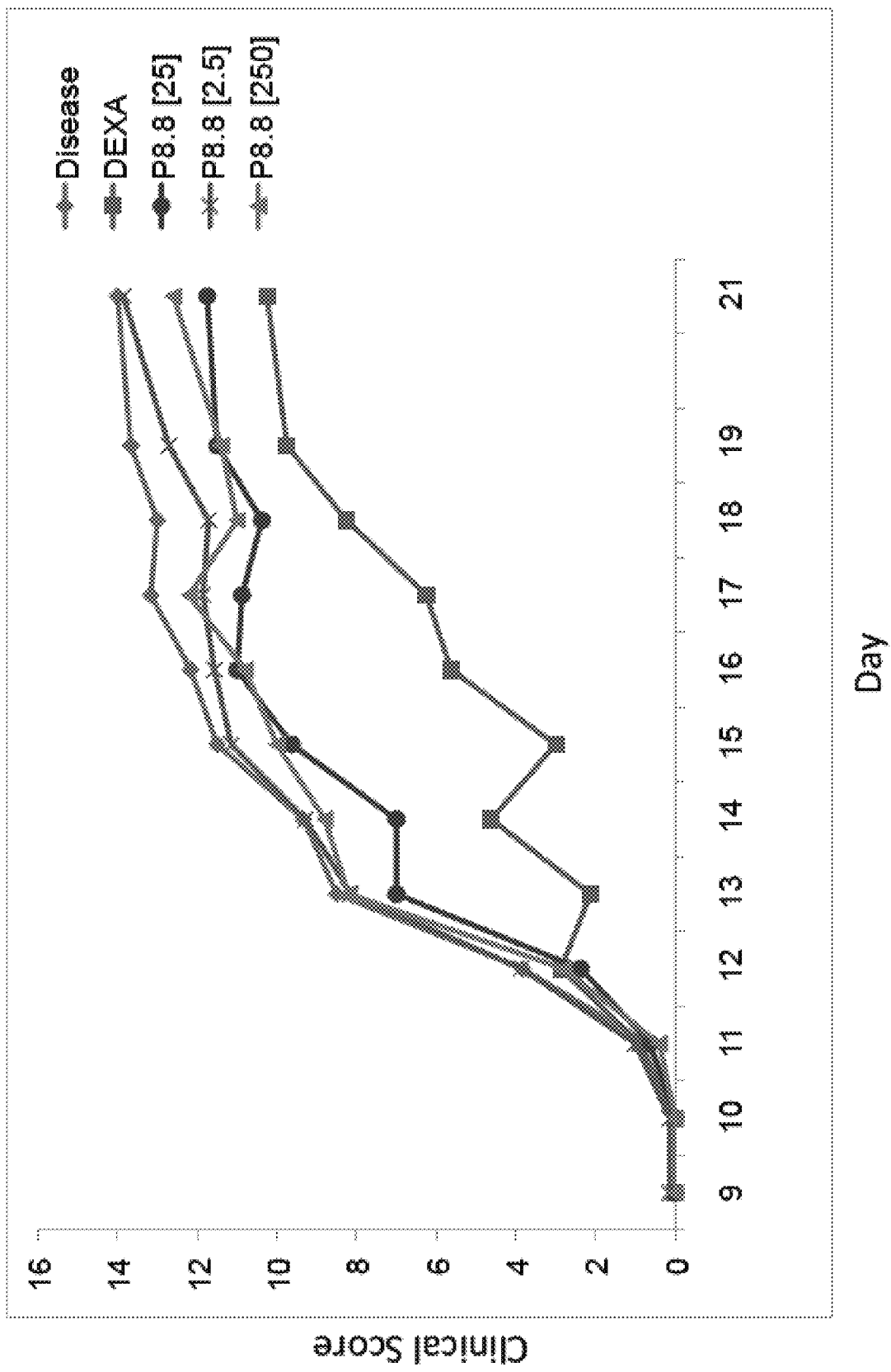
FIG. 30 shows the effect of multiple doses of peptide 8.8 administered to AIA rats.

P8.8 (WVFGAAMCK; SEQ ID NO: 11) is a point mutation derivative of P8 (WVFGNAMCK; SEQ ID NO: 5) with a distinct CK-binding profile. P8.8 was tested for anti-inflammatory activity in a rat model of AIA (FIG. 30). The peptide was injected IP at three different doses, 2.5 µg, 25 µg and 250 µg on days 7-18 following disease induction on day 0. P8.8 had an anti-inflammatory effect from about day12 that was maximal (20%) on day 18 (25 µg). Inflammation in the Dexa-treated group increased from day 15, 2 days after the second injection, approaching inflammation in the disease, untreated group by day 21. Of the three doses, the 25 µg dose proved to be the most efficacious.

Example 33

Comparative Study of Native Peptide 8 Homologue Efficacy in the Animal Model of Disease, Adjuvant Induced Arthritis (AIA)

Peptides (P) 8.77 (WVFGVHFCK; SEQ ID NO: 10), P15 (WVFGSGLCK; SEQ ID NO: 16), P8 Rat (WVFGNMICK; SEQ ID NO: 27) and P8 (WVFGNAMCK; SEQ ID NO: 5) are native homologues. P8.77 is found in the ECL2 of the human CK receptor CCR7. P15 is found in the ECL-1 of the human CK receptor, CXCR3. P8 Rat is found in ECL-2 of the rat CK receptor, CCR2. P8 is found in ECL-2 of the human CK receptor, CCR2. Each of the peptides has a discrete CK-binding profile (P8.77/P8 Rat) and each binds specifically and differentially to RA-associated and RA-unrelated CKs. The peptides were tested for efficacy in the rat AIA model of disease. Each peptide was injected separately (25 µg) on days 7-18 following disease induction on day 0 (FIG. 31). Each of the peptides had an anti-inflammatory effect from day 11-12 that was maximal for P8 Rat (40%) and P8.77 (23%) on day 13-14. The significantly greater anti-inflammatory activity of P8 Rat may be attributed to a species-specific effect: the rat-specific peptide is optimal for altering the course of the disease in the context of the rat. The implication is that the human-derived peptides employed in this study (P8, P8.77, P15) are suboptimal for the rat model of AIA and that in the human patient human peptide therapeutic activity will be enhanced. Inflammation in the Dexa-treated group increased from day 14, 1 day after the second injection, approaching inflammation in the disease, untreated group by day 21.

Example 34

Efficacy Study of Peptide+Dexamethasone Combination Treatment in the Animal Model of Disease, Adjuvant Induced Arthritis (AIA)

Dexamethasone (Dexa) is an anti-inflammatory steroid that suppresses the immune system and is the first line of treatment for acute inflammatory conditions. The chemokine binding peptides described here are immune modulators that are intended for the long-term treatment of chronic inflammatory diseases. The sequential administration of Dexa and peptides was tested on AIA rats in combination treatment protocols. Employing Combination Efficacy Protocol 1 (EXAMPLES, Materials and Methods) the treatments, Dexa/Dexa followed by PBS, delayed the onset of inflammation until day15 that by day 28 inflammation was comparable with the disease, untreated group (FIG. 32). Treatment of Dexa followed by peptide 15 (P15, 3 ug/injection) delayed the inflammatory response significantly so that on day 28 the Clinical Score (CS) of the combination-treated group was 8 compared to 14 of the disease, untreated group.

FIG. 33 shows the results of a study employing Combinations Efficacy Protocols 2 and 3. Peptide 15 (P15) alone (25 ug/injection) reduced inflammation from day 11 with a maximal effect (30%) on day 17. The combination treatment of Dexa followed by P15 was more efficacious that Dexa followed by PBS in reducing and delaying the increase in inflammation. The combination of Dexa preceded and followed by P15 injections was the most efficacious treatment in reducing and delaying the increase in inflammation to the greatest extent.

It is understood that modifications that do not substantially affect the activity of the various embodiments of this invention are also provided within the definition of the invention provided herein. Accordingly, the above examples are intended to illustrate but not limit the present invention. While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the claims.

REFERENCES

Barabasi A L and Oltvai Z N 2004 "Network biology: understanding the cell's functional organization" Nat Rev Genet 5, 101.

Billingham M E 1995 "Mechanisms and Models of Rheumatoid Arthritis. Ed. Pettipher ER London, Academic Press, 389.

Donaldson L F et al 1993 "A discrete adjuvant-induced monoarthritis in the rat: effects of adjuvant dose" J Neuroscience Methods 49, 5.

Estrada E 2006 "Virtual identification of essential proteins within the protein interaction network of yeast" Proteomics 6, 35-40.

Fabian M A 2005 "A small molecule-kinase interaction map for clinical kinase inhibitors" Nat Biotechnol 23, 329.

Franz S 2005 "Drug discovery: playing dirty" Nature 437, 942.

Gerard C and Rollins B J 2001 "Chemokines and disease" Nat Immunol 2, 108.

Gribbon P and Sewing A 2005 "High-throughput drug discovery: what can we expect from HTS?" Drug Discovery Today 10, 17.

Hampton T 2004 "Promiscuous anticancer drugs that hit multiple targets may thwart resistace" Jama 292, 419.

Hopkins A L 2007 "Network biology illuminates our understanding of drug action" Nat Biotechnology 25, 1110.

Horuk R and Ng H P 2000 "Chemokine receptor antagonists" Med Res Rev 20, 155.

Katchar K et al 2007 "MIP-3alpha neutralizing monoclonal antibody protects against TNBS-induced colonic injury and inflammation in mice" Am J Physiol Gastrointest Liver Physiol 292, G1263.

Kobayashi T et al 2007 "Exclusive increase of CX3CR1+ CD28−CD4+ T cells in inflammatory bowel disease and their recruitment as intraepithelial lymphocytes" Inflamm Bowel Dis 3, 837.

Murphy G et al 2008 "Fractalkine in rheumatoid arthritis: a review to date" Rheumatology 47, 1446.

Nanki T et al 2001 "Chemokines Regulate IL-6 and IL-8 Production by Fibroblast-Like Synoviocytes from Patients with Rheumatoid Arthritis" J Immunol 167, 5381.

Ohlson S et al 1997 "Detection and characterization of weak affinity antibody antigen recognition with biomolecular interaction analysis" J Mol Recognit 10, 135.

Ohlson S 2008 "Designing transient binding drugs: a new concept for drug discovery" Drug Discov Today 13, 433.

Parrish R J et al 2006 "Yeast two-hybrid contributions to interactome mapping" Curr Opin Biotechnol 17, 387.

Pelegri C et al 1995 "Immunohistochemical changes in synovial tissue during the course of adjuvant arthritis" J Rheumatol. 22, 124.

Power C A 203 "Knock out models to dissect chemokine receptor function in vivo" J Immunol Methods 273, 73.

Roth B L et al 2004 "Magic shotguns versus magic bullets: selectively non-selective drugs for mood disorders and schizophrenia" Nat Rev Drug Discov 3, 353.

Ruffner H et al 2007 "Human protein-protein interaction networks and the value for drug discovery" Drug Discovery Toda 12,709.

Shahrara S 2005 "Amelioration of Rat Adjuvatn-Induced Arthritis by Met-RANTES" Arthritis and Rheumatism 52, 1907.

Singh U P et al 2007 "CXCR3 axis: role in inflammatory bowel disease and its therapeutic implication" Endocr Metab Immune Disord Drug Targets 7, 111.

Schwarz M K and Wells T N 2002 "New therapeutics that modulate chemokine networks" Nat Rev Drug Discov 1, 347.

Vasilescu J and Figeys D 2006 "Mapping protein-protein interactions by mass spectrometry" Curr Opin Biotechnol 17, 394.

Wong D T and Bymaster F P 2002 "Dual serotonin and noradrenaline uptake inhibitor class of antidepressants potential for greater efficacy or just hype?" Prog Drug Res 58, 169.

What is claimed is:

1. A CKRD peptide selected from the group consisting of: (a) a peptide consisting of the amino acid sequence of SEQ ID NO: 16, and (b) a peptide consisting of the amino acid sequence of SEQ ID NO: 16; wherein amino acid positions 5, 6, and 7 of SEQ ID NO. 16 have been replaced with His-Gly-Met or Asn-Ala-Met; and wherein the peptide of (a) or (b) binds to cytokines MIG, I-309, Eotaxin, Eotaxin 2, Eotaxin 3, SDF1-α, SDF1-β, and MIP3-α, and has an anti-inflammatory effect.

2. The CKRD peptide according to claim 1 wherein the CKRD peptide consists of the amino acid sequence of WVFGSGLCK (SEQ ID NO: 16).

3. The CKRD peptide of claim 1 wherein the CKRD peptide consists of the amino acid sequence of WVFGHGMCK (SEQ ID NO: 2).

4. The CKRD peptide according to claim 1 wherein said peptide further binds with a dissociation constant less than 1 mM to one or more constitutive chemokines selected from the group consisting of Fractalkine and Lymphotactin.

5. The CKRD peptide according to claim 1 wherein said peptide further binds with a dissociation constant less than 1 mM to one or more dual function chemokines selected from the group consisting of: SDF1-α; SDF1-β; BCA-1; MIP3-α; MIP3-β; Exodus-2; TECK; and C-TAC.

6. A pharmaceutical composition comprising the CKRD peptide according to claim 1 and a pharmaceutically acceptable carrier.

7. A method for treating rheumatoid arthritis comprising administrating to a subject in need thereof the CKRD peptide of claim 1.

* * * * *

SEQUENCE LISTING

<160> NUMBER OF SEQ ID NOS: 162

<210> SEQ ID NO 1
<211> LENGTH: 8
<212> TYPE: PRT
<213> ORGANISM: Homo sapiens

<400> SEQUENCE: 1

Ser Tyr Tyr Asp Asp Val Gly Leu
1               5

<210> SEQ ID NO 2
<211> LENGTH: 9
<212> TYPE: PRT
<213> ORGANISM: Homo sapiens

<400> SEQUENCE: 2

Trp Val Phe Gly His Gly Met Cys Lys
1               5

<210> SEQ ID NO 3
<211> LENGTH: 7
<212> TYPE: PRT
<213> ORGANISM: Homo sapiens

<400> SEQUENCE: 3

Leu Phe Gly Asn Asp Cys Glu
1               5

<210> SEQ ID NO 4
<211> LENGTH: 9
<212> TYPE: PRT
<213> ORGANISM: Homo sapiens

<400> SEQUENCE: 4

Trp Val Phe Gly Thr Phe Leu Cys Lys
1               5

<210> SEQ ID NO 5
<211> LENGTH: 9
<212> TYPE: PRT
<213> ORGANISM: Homo sapiens

<400> SEQUENCE: 5

Trp Val Phe Gly Asn Ala Met Cys Lys
1               5

<210> SEQ ID NO 6
<211> LENGTH: 6
<212> TYPE: PRT
<213> ORGANISM: Homo sapiens

<400> SEQUENCE: 6

Gly Asn Ala Met Cys Lys
1               5

<210> SEQ ID NO 7
<211> LENGTH: 4
<212> TYPE: PRT
<213> ORGANISM: Homo sapiens

<400> SEQUENCE: 7

Trp Val Phe Gly
1

<210> SEQ ID NO 8
<211> LENGTH: 9
<212> TYPE: PRT
<213> ORGANISM: Homo sapiens

<400> SEQUENCE: 8

Trp Val Phe Gly Ala Ala Ala Cys Lys
1               5

<210> SEQ ID NO 9
<211> LENGTH: 9
<212> TYPE: PRT
<213> ORGANISM: Homo sapiens

<400> SEQUENCE: 9

Trp Val Phe Gly Asn Ala Ala Cys Lys
1               5

<210> SEQ ID NO 10
<211> LENGTH: 9
<212> TYPE: PRT
<213> ORGANISM: Homo sapiens

<400> SEQUENCE: 10

Trp Val Phe Gly Val His Phe Cys Lys
1               5

<210> SEQ ID NO 11
<211> LENGTH: 9
<212> TYPE: PRT
<213> ORGANISM: Homo sapiens

<400> SEQUENCE: 11

Trp Val Phe Gly Ala Ala Met Cys Lys
1               5

<210> SEQ ID NO 12
<211> LENGTH: 5
<212> TYPE: PRT
<213> ORGANISM: Homo sapiens

<400> SEQUENCE: 12

Asn Ala Met Cys Lys
1               5

<210> SEQ ID NO 13
<211> LENGTH: 7
<212> TYPE: PRT
<213> ORGANISM: Homo sapiens

<400> SEQUENCE: 13

Phe Phe Gly Leu Asn Asn Cys
1               5

<210> SEQ ID NO 14
<211> LENGTH: 9
<212> TYPE: PRT
<213> ORGANISM: Homo sapiens

<400> SEQUENCE: 14

Thr Thr Phe Phe Asp Tyr Asp Tyr Gly
1               5

<210> SEQ ID NO 15

-continued

```
<211> LENGTH: 5
<212> TYPE: PRT
<213> ORGANISM: Homo sapiens

<400> SEQUENCE: 15

Glu Asp Ser Val Tyr
1               5

<210> SEQ ID NO 16
<211> LENGTH: 9
<212> TYPE: PRT
<213> ORGANISM: Homo sapiens

<400> SEQUENCE: 16

Trp Val Phe Gly Ser Gly Leu Cys Lys
1               5

<210> SEQ ID NO 17
<211> LENGTH: 9
<212> TYPE: PRT
<213> ORGANISM: Homo sapiens

<400> SEQUENCE: 17

His His Thr Cys Ser Leu His Phe Pro
1               5

<210> SEQ ID NO 18
<211> LENGTH: 9
<212> TYPE: PRT
<213> ORGANISM: Homo sapiens

<400> SEQUENCE: 18

His Tyr Thr Cys Ser Ser His Phe Pro
1               5

<210> SEQ ID NO 19
<211> LENGTH: 10
<212> TYPE: PRT
<213> ORGANISM: Homo sapiens

<400> SEQUENCE: 19

Asp Arg Tyr Leu Asn Ile Val His Ala Thr
1               5                   10

<210> SEQ ID NO 20
<211> LENGTH: 6
<212> TYPE: PRT
<213> ORGANISM: Homo sapiens

<400> SEQUENCE: 20

Thr Lys Cys Gln Lys Glu
1               5

<210> SEQ ID NO 21
<211> LENGTH: 8
<212> TYPE: PRT
<213> ORGANISM: Homo sapiens

<400> SEQUENCE: 21

Asn Thr Thr Glu Asp Tyr Asp Thr
1               5

<210> SEQ ID NO 22
<211> LENGTH: 9
<212> TYPE: PRT
```

<213> ORGANISM: Homo sapiens

<400> SEQUENCE: 22

Trp Val Phe Gly His Gly Met Cys Lys
1               5

<210> SEQ ID NO 23
<211> LENGTH: 8
<212> TYPE: PRT
<213> ORGANISM: Homo sapiens

<400> SEQUENCE: 23

Ser Tyr Tyr Asp Asp Val Gly Leu
1               5

<210> SEQ ID NO 24
<211> LENGTH: 8
<212> TYPE: PRT
<213> ORGANISM: Homo sapiens

<400> SEQUENCE: 24

Asp Tyr Asp Tyr Gly Ala Pro Cys
1               5

<210> SEQ ID NO 25
<211> LENGTH: 5
<212> TYPE: PRT
<213> ORGANISM: Homo sapiens

<400> SEQUENCE: 25

Asp Tyr Asp Tyr Gly
1               5

<210> SEQ ID NO 26
<211> LENGTH: 4
<212> TYPE: PRT
<213> ORGANISM: Homo sapiens

<400> SEQUENCE: 26

Asp Tyr Asp Tyr
1

<210> SEQ ID NO 27
<211> LENGTH: 9
<212> TYPE: PRT
<213> ORGANISM: Homo sapiens

<400> SEQUENCE: 27

Trp Val Phe Gly Asn Met Ile Cys Lys
1               5

<210> SEQ ID NO 28
<211> LENGTH: 13
<212> TYPE: PRT
<213> ORGANISM: Homo sapiens

<400> SEQUENCE: 28

Val Thr Thr Phe Phe Asp Tyr Asp Tyr Gly Ala Pro Cys
1               5                   10

<210> SEQ ID NO 29
<211> LENGTH: 9
<212> TYPE: PRT
<213> ORGANISM: Homo sapiens

```
<400> SEQUENCE: 29

Trp Val Phe Gly Asp Ala Met Cys Lys
1               5

<210> SEQ ID NO 30
<211> LENGTH: 9
<212> TYPE: PRT
<213> ORGANISM: Homo sapiens

<400> SEQUENCE: 30

Trp Val Phe Gly Asn Thr Met Cys Lys
1               5

<210> SEQ ID NO 31
<211> LENGTH: 9
<212> TYPE: PRT
<213> ORGANISM: Homo sapiens

<400> SEQUENCE: 31

Trp Val Phe Gly Ser Ala Met Cys Lys
1               5

<210> SEQ ID NO 32
<211> LENGTH: 9
<212> TYPE: PRT
<213> ORGANISM: Homo sapiens

<400> SEQUENCE: 32

Trp Val Phe Gly Asn Gly Met Cys Lys
1               5

<210> SEQ ID NO 33
<211> LENGTH: 9
<212> TYPE: PRT
<213> ORGANISM: Homo sapiens

<400> SEQUENCE: 33

Trp Val Phe Gly Asn Glu Met Cys Lys
1               5

<210> SEQ ID NO 34
<211> LENGTH: 9
<212> TYPE: PRT
<213> ORGANISM: Homo sapiens

<400> SEQUENCE: 34

Trp Val Phe Ser Asn Ala Met Cys Lys
1               5

<210> SEQ ID NO 35
<211> LENGTH: 9
<212> TYPE: PRT
<213> ORGANISM: Homo sapiens

<400> SEQUENCE: 35

Trp Val Phe Gly Asn Val Met Cys Lys
1               5

<210> SEQ ID NO 36
<211> LENGTH: 9
<212> TYPE: PRT
<213> ORGANISM: Homo sapiens

<400> SEQUENCE: 36
```

Trp Val Phe Gly Lys Ala Met Cys Lys
1               5

<210> SEQ ID NO 37
<211> LENGTH: 9
<212> TYPE: PRT
<213> ORGANISM: Homo sapiens

<400> SEQUENCE: 37

Trp Val Phe Gly Thr Ala Met Cys Lys
1               5

<210> SEQ ID NO 38
<211> LENGTH: 9
<212> TYPE: PRT
<213> ORGANISM: Homo sapiens

<400> SEQUENCE: 38

Trp Thr Phe Gly Asn Ala Met Cys Lys
1               5

<210> SEQ ID NO 39
<211> LENGTH: 9
<212> TYPE: PRT
<213> ORGANISM: Homo sapiens

<400> SEQUENCE: 39

Trp Val Phe Gly Asn Ala Leu Cys Lys
1               5

<210> SEQ ID NO 40
<211> LENGTH: 9
<212> TYPE: PRT
<213> ORGANISM: Homo sapiens

<400> SEQUENCE: 40

Trp Val Phe Gly Gly Ala Met Cys Lys
1               5

<210> SEQ ID NO 41
<211> LENGTH: 9
<212> TYPE: PRT
<213> ORGANISM: Homo sapiens

<400> SEQUENCE: 41

Trp Ile Phe Gly Asp Ala Met Cys Lys
1               5

<210> SEQ ID NO 42
<211> LENGTH: 9
<212> TYPE: PRT
<213> ORGANISM: Homo sapiens

<400> SEQUENCE: 42

Trp Val Phe Gly Asn Ile Met Cys Lys
1               5

<210> SEQ ID NO 43
<211> LENGTH: 9
<212> TYPE: PRT
<213> ORGANISM: Homo sapiens

<400> SEQUENCE: 43

Trp Ile Phe Gly Asp Ala Met Cys Lys
1               5

```
<210> SEQ ID NO 44
<211> LENGTH: 9
<212> TYPE: PRT
<213> ORGANISM: Homo sapiens

<400> SEQUENCE: 44

Trp Val Phe Gly Asn Ala Ala Cys Lys
1               5

<210> SEQ ID NO 45
<211> LENGTH: 4
<212> TYPE: PRT
<213> ORGANISM: Homo sapiens

<400> SEQUENCE: 45

Trp Val Phe Ser
1

<210> SEQ ID NO 46
<211> LENGTH: 9
<212> TYPE: PRT
<213> ORGANISM: Homo sapiens

<400> SEQUENCE: 46

His Arg Thr Cys Ser Leu His Phe Pro
1               5

<210> SEQ ID NO 47
<211> LENGTH: 9
<212> TYPE: PRT
<213> ORGANISM: Homo sapiens

<400> SEQUENCE: 47

His Tyr Thr Cys Ser Leu His Phe Pro
1               5

<210> SEQ ID NO 48
<211> LENGTH: 9
<212> TYPE: PRT
<213> ORGANISM: Homo sapiens

<400> SEQUENCE: 48

His His Thr Cys Ser Pro His Phe Pro
1               5

<210> SEQ ID NO 49
<211> LENGTH: 9
<212> TYPE: PRT
<213> ORGANISM: Homo sapiens

<400> SEQUENCE: 49

His Phe Thr Cys Ser Leu His Phe Pro
1               5

<210> SEQ ID NO 50
<211> LENGTH: 9
<212> TYPE: PRT
<213> ORGANISM: Homo sapiens

<400> SEQUENCE: 50

His Thr Thr Cys Ser Leu His Phe Pro
1               5
```

<210> SEQ ID NO 51
<211> LENGTH: 7
<212> TYPE: PRT
<213> ORGANISM: Homo sapiens

<400> SEQUENCE: 51

Thr Cys Ser Leu His Phe Pro
1               5

<210> SEQ ID NO 52
<211> LENGTH: 9
<212> TYPE: PRT
<213> ORGANISM: Homo sapiens

<400> SEQUENCE: 52

His His Ala Ser Ser Leu His Phe Pro
1               5

<210> SEQ ID NO 53
<211> LENGTH: 8
<212> TYPE: PRT
<213> ORGANISM: Homo sapiens

<400> SEQUENCE: 53

His His Glu Cys Ser Leu His Phe
1               5

<210> SEQ ID NO 54
<211> LENGTH: 9
<212> TYPE: PRT
<213> ORGANISM: Homo sapiens

<400> SEQUENCE: 54

Gln His Thr Cys Ser Pro His Phe Pro
1               5

<210> SEQ ID NO 55
<211> LENGTH: 8
<212> TYPE: PRT
<213> ORGANISM: Homo sapiens

<400> SEQUENCE: 55

His Ser Cys Asn Leu His Phe Pro
1               5

<210> SEQ ID NO 56
<211> LENGTH: 8
<212> TYPE: PRT
<213> ORGANISM: Homo sapiens

<400> SEQUENCE: 56

His Thr Cys Ser Pro His Phe Pro
1               5

<210> SEQ ID NO 57
<211> LENGTH: 8
<212> TYPE: PRT
<213> ORGANISM: Homo sapiens

<400> SEQUENCE: 57

His Ser Cys Ser Leu His Tyr Pro
1               5

<210> SEQ ID NO 58
<211> LENGTH: 7

<212> TYPE: PRT
<213> ORGANISM: Homo sapiens

<400> SEQUENCE: 58

His Thr Cys Asn Leu His Phe
1               5

<210> SEQ ID NO 59
<211> LENGTH: 7
<212> TYPE: PRT
<213> ORGANISM: Homo sapiens

<400> SEQUENCE: 59

Thr Cys Thr Leu His Phe Pro
1               5

<210> SEQ ID NO 60
<211> LENGTH: 7
<212> TYPE: PRT
<213> ORGANISM: Homo sapiens

<400> SEQUENCE: 60

His Ser Cys Ser Leu His Phe
1               5

<210> SEQ ID NO 61
<211> LENGTH: 9
<212> TYPE: PRT
<213> ORGANISM: Homo sapiens

<400> SEQUENCE: 61

His Asn Thr Cys Ser Ser His Phe Pro
1               5

<210> SEQ ID NO 62
<211> LENGTH: 7
<212> TYPE: PRT
<213> ORGANISM: Homo sapiens

<400> SEQUENCE: 62

His His Ser Cys Ser Leu His
1               5

<210> SEQ ID NO 63
<211> LENGTH: 6
<212> TYPE: PRT
<213> ORGANISM: Homo sapiens

<400> SEQUENCE: 63

Cys Ser Leu His Phe Pro
1               5

<210> SEQ ID NO 64
<211> LENGTH: 7
<212> TYPE: PRT
<213> ORGANISM: Homo sapiens

<400> SEQUENCE: 64

His Thr Cys Ser Leu Gln Phe
1               5

<210> SEQ ID NO 65
<211> LENGTH: 9
<212> TYPE: PRT
<213> ORGANISM: Homo sapiens

```
<400> SEQUENCE: 65

His Arg Thr Cys Ser Pro His Phe Pro
1               5

<210> SEQ ID NO 66
<211> LENGTH: 9
<212> TYPE: PRT
<213> ORGANISM: Homo sapiens

<400> SEQUENCE: 66

His Tyr Thr Cys Ser Pro His Phe Pro
1               5

<210> SEQ ID NO 67
<211> LENGTH: 6
<212> TYPE: PRT
<213> ORGANISM: Homo sapiens

<400> SEQUENCE: 67

His His Thr Cys Ser Leu
1               5

<210> SEQ ID NO 68
<211> LENGTH: 6
<212> TYPE: PRT
<213> ORGANISM: Homo sapiens

<400> SEQUENCE: 68

Gly Asn Ser Met Cys Lys
1               5

<210> SEQ ID NO 69
<211> LENGTH: 6
<212> TYPE: PRT
<213> ORGANISM: Homo sapiens

<400> SEQUENCE: 69

Gly Asp Ala Met Cys Lys
1               5

<210> SEQ ID NO 70
<211> LENGTH: 7
<212> TYPE: PRT
<213> ORGANISM: Homo sapiens

<400> SEQUENCE: 70

Leu Phe Gly Asn Glu Cys Glu
1               5

<210> SEQ ID NO 71
<211> LENGTH: 6
<212> TYPE: PRT
<213> ORGANISM: Homo sapiens

<400> SEQUENCE: 71

Phe Gly Asn Asp Cys Glu
1               5

<210> SEQ ID NO 72
<211> LENGTH: 7
<212> TYPE: PRT
<213> ORGANISM: Homo sapiens

<400> SEQUENCE: 72
```

```
Leu Tyr Gly Asn Asp Cys Glu
1               5
```

<210> SEQ ID NO 73
<211> LENGTH: 7
<212> TYPE: PRT
<213> ORGANISM: Homo sapiens

<400> SEQUENCE: 73

```
Leu Phe Gly Ser Asp Cys Glu
1               5
```

<210> SEQ ID NO 74
<211> LENGTH: 6
<212> TYPE: PRT
<213> ORGANISM: Homo sapiens

<400> SEQUENCE: 74

```
Leu Phe Gly Asn Asp Cys
1               5
```

<210> SEQ ID NO 75
<211> LENGTH: 7
<212> TYPE: PRT
<213> ORGANISM: Homo sapiens

<400> SEQUENCE: 75

```
Leu Phe Asn Asn Asp Cys Glu
1               5
```

<210> SEQ ID NO 76
<211> LENGTH: 7
<212> TYPE: PRT
<213> ORGANISM: Homo sapiens

<400> SEQUENCE: 76

```
Leu Phe Asp Asn Asp Cys Glu
1               5
```

<210> SEQ ID NO 77
<211> LENGTH: 7
<212> TYPE: PRT
<213> ORGANISM: Homo sapiens

<400> SEQUENCE: 77

```
Leu Phe Gly Thr Asp Cys Glu
1               5
```

<210> SEQ ID NO 78
<211> LENGTH: 7
<212> TYPE: PRT
<213> ORGANISM: Homo sapiens

<400> SEQUENCE: 78

```
Leu Phe Gly Asn Gly Cys Glu
1               5
```

<210> SEQ ID NO 79
<211> LENGTH: 9
<212> TYPE: PRT
<213> ORGANISM: Homo sapiens

<400> SEQUENCE: 79

```
Leu Phe Gly Asn Asp Ala Ala Cys Glu
```

```
1               5
```

<210> SEQ ID NO 80
<211> LENGTH: 8
<212> TYPE: PRT
<213> ORGANISM: Homo sapiens

<400> SEQUENCE: 80

```
Leu Phe Gly Asn Asp Ala Cys Glu
1               5
```

<210> SEQ ID NO 81
<211> LENGTH: 7
<212> TYPE: PRT
<213> ORGANISM: Homo sapiens

<400> SEQUENCE: 81

```
Leu Phe Gly Asn Ala Cys Glu
1               5
```

<210> SEQ ID NO 82
<211> LENGTH: 9
<212> TYPE: PRT
<213> ORGANISM: Homo sapiens

<400> SEQUENCE: 82

```
Leu Phe Gly Asn Ile Asn Asp Cys Glu
1               5
```

<210> SEQ ID NO 83
<211> LENGTH: 9
<212> TYPE: PRT
<213> ORGANISM: Homo sapiens

<400> SEQUENCE: 83

```
Leu Phe Phe Val Gly Asn Asp Cys Glu
1               5
```

<210> SEQ ID NO 84
<211> LENGTH: 7
<212> TYPE: PRT
<213> ORGANISM: Homo sapiens

<400> SEQUENCE: 84

```
Leu Phe Gly Tyr Asp Cys Glu
1               5
```

<210> SEQ ID NO 85
<211> LENGTH: 7
<212> TYPE: PRT
<213> ORGANISM: Homo sapiens

<400> SEQUENCE: 85

```
Leu Phe Gly Asp Glu Cys Glu
1               5
```

<210> SEQ ID NO 86
<211> LENGTH: 7
<212> TYPE: PRT
<213> ORGANISM: Homo sapiens

<400> SEQUENCE: 86

```
Met Phe Gly Asn Glu Cys Glu
1               5
```

```
<210> SEQ ID NO 87
<211> LENGTH: 6
<212> TYPE: PRT
<213> ORGANISM: Homo sapiens

<400> SEQUENCE: 87

Phe Gly Asn Glu Cys Glu
1               5

<210> SEQ ID NO 88
<211> LENGTH: 7
<212> TYPE: PRT
<213> ORGANISM: Homo sapiens

<400> SEQUENCE: 88

Leu Tyr Gly Asn Asp Cys Asp
1               5

<210> SEQ ID NO 89
<211> LENGTH: 6
<212> TYPE: PRT
<213> ORGANISM: Homo sapiens

<400> SEQUENCE: 89

Phe Gly Asn Asn Cys Glu
1               5

<210> SEQ ID NO 90
<211> LENGTH: 6
<212> TYPE: PRT
<213> ORGANISM: Homo sapiens

<400> SEQUENCE: 90

Phe Gly Asp Asp Cys Glu
1               5

<210> SEQ ID NO 91
<211> LENGTH: 7
<212> TYPE: PRT
<213> ORGANISM: Homo sapiens

<400> SEQUENCE: 91

Leu Phe Gly Asn Asp Ser Glu
1               5

<210> SEQ ID NO 92
<211> LENGTH: 10
<212> TYPE: PRT
<213> ORGANISM: Homo sapiens

<400> SEQUENCE: 92

Thr Lys Cys Gln Lys Glu Asp Ser Val Tyr
1               5                   10

<210> SEQ ID NO 93
<211> LENGTH: 7
<212> TYPE: PRT
<213> ORGANISM: Homo sapiens

<400> SEQUENCE: 93

Thr Lys Cys Gln Lys Glu Asn
1               5

<210> SEQ ID NO 94
```

```
<211> LENGTH: 7
<212> TYPE: PRT
<213> ORGANISM: Homo sapiens

<400> SEQUENCE: 94

Thr Lys Cys Glu Lys Glu Asp
1               5

<210> SEQ ID NO 95
<211> LENGTH: 9
<212> TYPE: PRT
<213> ORGANISM: Homo sapiens

<400> SEQUENCE: 95

Lys Cys Gln Asn Glu Ile Ser Val Tyr
1               5

<210> SEQ ID NO 96
<211> LENGTH: 10
<212> TYPE: PRT
<213> ORGANISM: Homo sapiens

<400> SEQUENCE: 96

Lys Cys Gln Val Pro Glu Asp Ser Val Tyr
1               5                   10

<210> SEQ ID NO 97
<211> LENGTH: 10
<212> TYPE: PRT
<213> ORGANISM: Homo sapiens

<400> SEQUENCE: 97

Lys Cys Gln Lys Glu Glu Ser Ile Val Tyr
1               5                   10

<210> SEQ ID NO 98
<211> LENGTH: 8
<212> TYPE: PRT
<213> ORGANISM: Homo sapiens

<400> SEQUENCE: 98

Lys Cys Gln Lys Gly Asp Ser Val
1               5

<210> SEQ ID NO 99
<211> LENGTH: 9
<212> TYPE: PRT
<213> ORGANISM: Homo sapiens

<400> SEQUENCE: 99

Lys Cys Gln Lys Gly Asp Thr Val Tyr
1               5

<210> SEQ ID NO 100
<211> LENGTH: 9
<212> TYPE: PRT
<213> ORGANISM: Homo sapiens

<400> SEQUENCE: 100

Lys Cys Leu Lys Glu Asp Ser Ile Tyr
1               5

<210> SEQ ID NO 101
<211> LENGTH: 9
<212> TYPE: PRT
```

```
<213> ORGANISM: Homo sapiens

<400> SEQUENCE: 101

Lys Cys Gln Lys Glu Asn Leu Val Tyr
1               5

<210> SEQ ID NO 102
<211> LENGTH: 7
<212> TYPE: PRT
<213> ORGANISM: Homo sapiens

<400> SEQUENCE: 102

Gln Lys Glu Asp Ser Val Tyr
1               5

<210> SEQ ID NO 103
<211> LENGTH: 7
<212> TYPE: PRT
<213> ORGANISM: Homo sapiens

<400> SEQUENCE: 103

Gln Lys Asp Asp Ser Val Tyr
1               5

<210> SEQ ID NO 104
<211> LENGTH: 8
<212> TYPE: PRT
<213> ORGANISM: Homo sapiens

<400> SEQUENCE: 104

Cys Gln Lys Ala Asp Ala Val Tyr
1               5

<210> SEQ ID NO 105
<211> LENGTH: 7
<212> TYPE: PRT
<213> ORGANISM: Homo sapiens

<400> SEQUENCE: 105

Cys Gln Lys Glu Asp Ser Val
1               5

<210> SEQ ID NO 106
<211> LENGTH: 7
<212> TYPE: PRT
<213> ORGANISM: Homo sapiens

<400> SEQUENCE: 106

Lys Cys Gln Lys Glu Asp Ser
1               5

<210> SEQ ID NO 107
<211> LENGTH: 7
<212> TYPE: PRT
<213> ORGANISM: Homo sapiens

<400> SEQUENCE: 107

Gln Lys Glu Asp Ser Val Tyr
1               5

<210> SEQ ID NO 108
<211> LENGTH: 8
<212> TYPE: PRT
<213> ORGANISM: Homo sapiens
```

<400> SEQUENCE: 108

Cys Gln Lys Glu Asp Gln Val Tyr
1               5

<210> SEQ ID NO 109
<211> LENGTH: 8
<212> TYPE: PRT
<213> ORGANISM: Homo sapiens

<400> SEQUENCE: 109

Cys Glu Lys Glu Asp Ser Ile Tyr
1               5

<210> SEQ ID NO 110
<211> LENGTH: 8
<212> TYPE: PRT
<213> ORGANISM: Homo sapiens

<400> SEQUENCE: 110

Cys Gln Lys Gly Asp Ser Val Tyr
1               5

<210> SEQ ID NO 111
<211> LENGTH: 11
<212> TYPE: PRT
<213> ORGANISM: Homo sapiens

<400> SEQUENCE: 111

Lys Cys Gln Lys Glu Phe Asp Ile Ser Val Tyr
1               5                   10

<210> SEQ ID NO 112
<211> LENGTH: 17
<212> TYPE: PRT
<213> ORGANISM: Homo sapiens

<400> SEQUENCE: 112

Thr Lys Ser Gln Lys Glu Asp Phe Leu Glu Ser Glu Lys Glu Ser Val
1               5                   10                  15

Tyr

<210> SEQ ID NO 113
<211> LENGTH: 9
<212> TYPE: PRT
<213> ORGANISM: Homo sapiens

<400> SEQUENCE: 113

Asp Arg Tyr Leu Asn Ile Val His Ala
1               5

<210> SEQ ID NO 114
<211> LENGTH: 10
<212> TYPE: PRT
<213> ORGANISM: Homo sapiens

<400> SEQUENCE: 114

Asp Arg Tyr Leu Ser Ile Val His Ala Thr
1               5                   10

<210> SEQ ID NO 115
<211> LENGTH: 10
<212> TYPE: PRT
<213> ORGANISM: Homo sapiens

```
<400> SEQUENCE: 115

Asp Arg Tyr Leu Ala Ile Val His Ala Thr
1               5                   10

<210> SEQ ID NO 116
<211> LENGTH: 7
<212> TYPE: PRT
<213> ORGANISM: Homo sapiens

<400> SEQUENCE: 116

Asn Thr Thr Glu Asp Tyr Asp
1               5

<210> SEQ ID NO 117
<211> LENGTH: 7
<212> TYPE: PRT
<213> ORGANISM: Homo sapiens

<400> SEQUENCE: 117

Thr Thr Glu Asp Tyr Asp Thr
1               5

<210> SEQ ID NO 118
<211> LENGTH: 8
<212> TYPE: PRT
<213> ORGANISM: Homo sapiens

<400> SEQUENCE: 118

Asn Thr Thr Asn Asp Tyr Asp Thr
1               5

<210> SEQ ID NO 119
<211> LENGTH: 8
<212> TYPE: PRT
<213> ORGANISM: Homo sapiens

<400> SEQUENCE: 119

Asp Thr Thr Glu Asp Tyr Glu Thr
1               5

<210> SEQ ID NO 120
<211> LENGTH: 8
<212> TYPE: PRT
<213> ORGANISM: Homo sapiens

<400> SEQUENCE: 120

Asn Thr Ser Glu Asn Tyr Asp Thr
1               5

<210> SEQ ID NO 121
<211> LENGTH: 7
<212> TYPE: PRT
<213> ORGANISM: Homo sapiens

<400> SEQUENCE: 121

Asn Ser Thr Glu Asp Tyr Asp
1               5

<210> SEQ ID NO 122
<211> LENGTH: 7
<212> TYPE: PRT
<213> ORGANISM: Homo sapiens

<400> SEQUENCE: 122
```

```
Thr Thr Glu Asp Tyr Glu Thr
1               5
```

<210> SEQ ID NO 123
<211> LENGTH: 8
<212> TYPE: PRT
<213> ORGANISM: Homo sapiens

<400> SEQUENCE: 123

```
Asp Tyr Asp Tyr Ser Ala Pro Cys
1               5
```

<210> SEQ ID NO 124
<211> LENGTH: 8
<212> TYPE: PRT
<213> ORGANISM: Homo sapiens

<400> SEQUENCE: 124

```
Asp Tyr Asp Tyr Ala Ala Pro Cys
1               5
```

<210> SEQ ID NO 125
<211> LENGTH: 11
<212> TYPE: PRT
<213> ORGANISM: Homo sapiens

<400> SEQUENCE: 125

```
Asp Tyr Val Leu Gly Asp Tyr Gly Ala Pro Cys
1               5                   10
```

<210> SEQ ID NO 126
<211> LENGTH: 8
<212> TYPE: PRT
<213> ORGANISM: Homo sapiens

<400> SEQUENCE: 126

```
Asp Tyr Glu Tyr Ala Ala Pro Cys
1               5
```

<210> SEQ ID NO 127
<211> LENGTH: 7
<212> TYPE: PRT
<213> ORGANISM: Homo sapiens

<400> SEQUENCE: 127

```
Asp Tyr Glu Tyr Gly Ala Pro
1               5
```

<210> SEQ ID NO 128
<211> LENGTH: 7
<212> TYPE: PRT
<213> ORGANISM: Homo sapiens

<400> SEQUENCE: 128

```
Asn Tyr Asp Tyr Gly Ala Pro
1               5
```

<210> SEQ ID NO 129
<211> LENGTH: 8
<212> TYPE: PRT
<213> ORGANISM: Homo sapiens

<400> SEQUENCE: 129

```
Asp Tyr Asp Tyr Ser Glu Pro Cys
1               5
```

```
<210> SEQ ID NO 130
<211> LENGTH: 7
<212> TYPE: PRT
<213> ORGANISM: Homo sapiens

<400> SEQUENCE: 130

Asp Tyr Asp Tyr Gly Thr Pro
1               5

<210> SEQ ID NO 131
<211> LENGTH: 7
<212> TYPE: PRT
<213> ORGANISM: Homo sapiens

<400> SEQUENCE: 131

Asp Tyr Asp Tyr Gly Gly Pro
1               5

<210> SEQ ID NO 132
<211> LENGTH: 7
<212> TYPE: PRT
<213> ORGANISM: Homo sapiens

<400> SEQUENCE: 132

Asp Tyr Asp Phe Gly Ala Pro
1               5

<210> SEQ ID NO 133
<211> LENGTH: 7
<212> TYPE: PRT
<213> ORGANISM: Homo sapiens

<400> SEQUENCE: 133

Thr Thr Phe Phe Asp Tyr Asp
1               5

<210> SEQ ID NO 134
<211> LENGTH: 13
<212> TYPE: PRT
<213> ORGANISM: Homo sapiens

<400> SEQUENCE: 134

Val Thr Thr Ile Phe Asp Tyr Asp Tyr Gly Ala Pro Cys
1               5                   10

<210> SEQ ID NO 135
<211> LENGTH: 12
<212> TYPE: PRT
<213> ORGANISM: Homo sapiens

<400> SEQUENCE: 135

Thr Thr Ile Tyr Asp Tyr Asp Tyr Ser Ala Pro Cys
1               5                   10

<210> SEQ ID NO 136
<211> LENGTH: 12
<212> TYPE: PRT
<213> ORGANISM: Homo sapiens

<400> SEQUENCE: 136

Thr Thr Asn Tyr Asp Tyr Asp Tyr Ser Ala Pro Cys
1               5                   10
```

```
<210> SEQ ID NO 137
<211> LENGTH: 10
<212> TYPE: PRT
<213> ORGANISM: Homo sapiens

<400> SEQUENCE: 137

Thr Phe Phe Asp Tyr Asp Tyr Ile Gly Ala
1               5                   10

<210> SEQ ID NO 138
<211> LENGTH: 12
<212> TYPE: PRT
<213> ORGANISM: Homo sapiens

<400> SEQUENCE: 138

Thr Thr Ser Tyr Asp Tyr Asp Tyr Ser Glu Pro Cys
1               5                   10

<210> SEQ ID NO 139
<211> LENGTH: 12
<212> TYPE: PRT
<213> ORGANISM: Homo sapiens

<400> SEQUENCE: 139

Thr Thr Phe Tyr Asp Tyr Glu Phe Ala Gln Pro Cys
1               5                   10

<210> SEQ ID NO 140
<211> LENGTH: 10
<212> TYPE: PRT
<213> ORGANISM: Homo sapiens

<400> SEQUENCE: 140

Val Thr Thr Phe Tyr Ile Asp Tyr Asp Tyr
1               5                   10

<210> SEQ ID NO 141
<211> LENGTH: 7
<212> TYPE: PRT
<213> ORGANISM: Homo sapiens

<400> SEQUENCE: 141

Tyr Tyr Asp Asp Val Gly Leu
1               5

<210> SEQ ID NO 142
<211> LENGTH: 7
<212> TYPE: PRT
<213> ORGANISM: Homo sapiens

<400> SEQUENCE: 142

Ser Tyr Tyr Asp Asp Val Gly
1               5

<210> SEQ ID NO 143
<211> LENGTH: 8
<212> TYPE: PRT
<213> ORGANISM: Homo sapiens

<400> SEQUENCE: 143

Ser Tyr Tyr Asp Asp Val Ala Leu
1               5

<210> SEQ ID NO 144
<211> LENGTH: 8
```

```
<212> TYPE: PRT
<213> ORGANISM: Homo sapiens

<400> SEQUENCE: 144

Ser Tyr Tyr Asp Asp Val Asp Leu
1               5

<210> SEQ ID NO 145
<211> LENGTH: 8
<212> TYPE: PRT
<213> ORGANISM: Homo sapiens

<400> SEQUENCE: 145

Ser Tyr Tyr Asp Asp Leu Gly Leu
1               5

<210> SEQ ID NO 146
<211> LENGTH: 8
<212> TYPE: PRT
<213> ORGANISM: Homo sapiens

<400> SEQUENCE: 146

Ser Tyr Tyr Asp Asp Val Glu Leu
1               5

<210> SEQ ID NO 147
<211> LENGTH: 7
<212> TYPE: PRT
<213> ORGANISM: Homo sapiens

<400> SEQUENCE: 147

Tyr Tyr Asp Asp Ile Gly Leu
1               5

<210> SEQ ID NO 148
<211> LENGTH: 7
<212> TYPE: PRT
<213> ORGANISM: Homo sapiens

<400> SEQUENCE: 148

Ser Tyr Tyr Asp Asp Ile Gly
1               5

<210> SEQ ID NO 149
<211> LENGTH: 8
<212> TYPE: PRT
<213> ORGANISM: Homo sapiens

<400> SEQUENCE: 149

Ser Tyr Tyr Asp Ser Val Gly Leu
1               5

<210> SEQ ID NO 150
<211> LENGTH: 9
<212> TYPE: PRT
<213> ORGANISM: Homo sapiens
<220> FEATURE:
<221> NAME/KEY: misc_feature
<222> LOCATION: (5)..(7)
<223> OTHER INFORMATION: Xaa can be any naturally occurring amino acid

<400> SEQUENCE: 150

Trp Val Phe Gly Xaa Xaa Xaa Cys Lys
1               5
```

```
<210> SEQ ID NO 151
<211> LENGTH: 9
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 151

His Xaa Thr Cys Ser Xaa His Phe Pro
1               5

<210> SEQ ID NO 152
<211> LENGTH: 8
<212> TYPE: PRT
<213> ORGANISM: Homo sapiens
<220> FEATURE:
<221> NAME/KEY: misc_feature
<222> LOCATION: (4)..(6)
<223> OTHER INFORMATION: Xaa can be any naturally occurring amino acid

<400> SEQUENCE: 152

Leu Phe Gly Xaa Xaa Xaa Cys Glu
1               5

<210> SEQ ID NO 153
<211> LENGTH: 9
<212> TYPE: PRT
<213> ORGANISM: Homo sapiens
<220> FEATURE:
<221> NAME/KEY: misc_feature
<222> LOCATION: (4)..(6)
<223> OTHER INFORMATION: Xaa can be any naturally occurring amino acid

<400> SEQUENCE: 153

Lys Cys Gln Xaa Xaa Xaa Ser Val Tyr
1               5

<210> SEQ ID NO 154
<211> LENGTH: 10
<212> TYPE: PRT
<213> ORGANISM: Homo sapiens
<220> FEATURE:
<221> NAME/KEY: misc_feature
<222> LOCATION: (5)..(6)
<223> OTHER INFORMATION: Xaa can be any naturally occurring amino acid

<400> SEQUENCE: 154

Asp Arg Tyr Leu Xaa Xaa Val His Ala Thr
1               5                   10

<210> SEQ ID NO 155
<211> LENGTH: 6
<212> TYPE: PRT
<213> ORGANISM: Homo sapiens

<400> SEQUENCE: 155

His Asn Ala Met Cys Lys
1               5

<210> SEQ ID NO 156
<211> LENGTH: 4
<212> TYPE: PRT
<213> ORGANISM: Homo sapiens
```

```
<400> SEQUENCE: 156

Trp Tyr Phe Gly
1

<210> SEQ ID NO 157
<211> LENGTH: 9
<212> TYPE: PRT
<213> ORGANISM: Homo sapiens

<400> SEQUENCE: 157

Trp Ser Leu Gly Ser Ala Thr Cys Arg
1               5

<210> SEQ ID NO 158
<211> LENGTH: 9
<212> TYPE: PRT
<213> ORGANISM: Homo sapiens

<400> SEQUENCE: 158

Trp Val Phe Ser Asn Ala Thr Cys Lys
1               5

<210> SEQ ID NO 159
<211> LENGTH: 9
<212> TYPE: PRT
<213> ORGANISM: Homo sapiens

<400> SEQUENCE: 159

Trp Lys Phe Gln Thr Phe Met Cys Lys
1               5

<210> SEQ ID NO 160
<211> LENGTH: 9
<212> TYPE: PRT
<213> ORGANISM: Homo sapiens

<400> SEQUENCE: 160

Trp Val Phe Gly Gln Val Met Cys Lys
1               5

<210> SEQ ID NO 161
<211> LENGTH: 9
<212> TYPE: PRT
<213> ORGANISM: Homo sapiens

<400> SEQUENCE: 161

Trp Ile Phe Gly Thr Phe Leu Cys Lys
1               5

<210> SEQ ID NO 162
<211> LENGTH: 9
<212> TYPE: PRT
<213> ORGANISM: Homo sapiens

<400> SEQUENCE: 162

Thr Thr Phe Phe Tyr Tyr Asp Leu Gln
1               5
```